US008288559B2

(12) United States Patent  
Corona et al.

(10) Patent No.: US 8,288,559 B2  
(45) Date of Patent: Oct. 16, 2012

(54) LUMINOGENIC COMPOUNDS AND METHODS TO DETECT CYTOCHROME P450 3A ENZYMES

(75) Inventors: Cesear Corona, Paso robles, CA (US); Poncho Meisenheimer, San Luis Obispo, CA (US); Harry Tetsuo Uyeda, Los Osos, CA (US)

(73) Assignee: Promega Corporation, Milwaukee, WI (US)

( * ) Notice: Subject to any disclaimer, the term of this patent is extended or adjusted under 35 U.S.C. 154(b) by 425 days.

(21) Appl. No.: 12/543,376

(22) Filed: Aug. 18, 2009

(65) Prior Publication Data

US 2010/0062470 A1    Mar. 11, 2010

Related U.S. Application Data

(60) Provisional application No. 61/089,818, filed on Aug. 18, 2008.

(51) Int. Cl.  
*C07D 417/04* (2006.01)
(52) U.S. Cl. ............... 548/178; 435/8; 435/25; 435/7.4
(58) Field of Classification Search .................. 548/178  
See application file for complete search history.

(56) References Cited

U.S. PATENT DOCUMENTS

| | | | |
|---|---|---|---|
| 4,655,022 A | 4/1987 | Natori |
| 4,665,022 A | 5/1987 | Schaeffer et al. |
| 4,826,989 A | 5/1989 | Batz et al. |
| 4,992,531 A | 2/1991 | Patroni et al. |
| 5,035,999 A | 7/1991 | Geiger et al. |
| 5,098,828 A | 3/1992 | Geiger et al. |
| 5,114,704 A | 5/1992 | Spanier et al. |
| 5,283,179 A | 2/1994 | Wood |
| 5,283,180 A | 2/1994 | Zomer et al. |
| 5,290,684 A | 3/1994 | Kelly |
| 5,374,534 A | 12/1994 | Zomer et al. |
| 5,498,523 A | 3/1996 | Tabor et al. |
| 5,641,641 A | 6/1997 | Wood |
| 5,650,135 A | 7/1997 | Contag et al. |
| 5,650,289 A | 7/1997 | Wood |
| 5,726,041 A | 3/1998 | Chrespi et al. |
| 5,744,320 A | 4/1998 | Sherf et al. |
| 5,756,303 A | 5/1998 | Sato et al. |
| 5,780,287 A | 7/1998 | Kraus et al. |
| 5,814,471 A | 9/1998 | Wood |
| 5,876,946 A | 3/1999 | Burbaum et al. |
| 5,976,825 A | 11/1999 | Hochman |
| 6,143,492 A | 11/2000 | Makings et al. |
| 6,217,847 B1 | 4/2001 | Contag et al. |
| 6,291,164 B1 | 9/2001 | Blakesley |
| 6,299,858 B1 | 10/2001 | Serbedzija et al. |
| 6,376,208 B1 | 4/2002 | Kajiyama |
| 6,420,130 B1 | 7/2002 | Makings et al. |
| 6,514,687 B1 | 2/2003 | Makings et al. |
| 6,638,713 B2 | 10/2003 | Makings et al. |
| 7,118,878 B1 | 10/2006 | Hawkins et al. |
| 7,524,876 B2 | 4/2009 | Takakura et al. |
| 2002/0076777 A1 | 6/2002 | Merkulov et al. |
| 2003/0211560 A1 | 11/2003 | O'Brien et al. |
| 2003/0237103 A1 | 12/2003 | Jacob et al. |
| 2004/0146959 A1 | 7/2004 | Graham et al. |
| 2004/0171099 A1 | 9/2004 | Cali et al. |
| 2004/0248225 A1 | 12/2004 | Heindl et al. |
| 2005/0009098 A1 | 1/2005 | Reymonds et al. |
| 2005/0026171 A1 | 2/2005 | Hawkins et al. |
| 2005/0118257 A1 | 6/2005 | Bova |
| 2005/0153306 A1 | 7/2005 | Harris |
| 2007/0015790 A1 | 1/2007 | Cali et al. |
| 2007/0155806 A1 | 7/2007 | Takakura et al. |
| 2008/0194522 A1 | 8/2008 | Chen et al. |
| 2008/0299593 A1 | 12/2008 | Cali et al. |
| 2009/0023173 A1 | 1/2009 | Cali et al. |
| 2011/0003316 A1 | 1/2011 | Cali et al. |

FOREIGN PATENT DOCUMENTS

| | | |
|---|---|---|
| EP | 0411912 | 2/1991 |
| JP | 63-501571 | 6/1988 |
| JP | 01-502431 | 8/1989 |
| JP | 08-059686 | 3/1996 |
| JP | 2000-505-086 | 4/2000 |
| JP | 2000-270894 | 10/2000 |
| JP | 2002080476 | 3/2002 |
| RU | 2242471 | 12/2004 |
| WO | 87/02667 | 5/1987 |
| WO | 88/05434 | 7/1988 |
| WO | WO 96/31206 | 10/1996 |
| WO | 97/36885 | 10/1997 |
| WO | WO 99/60096 | 11/1999 |
| WO | WO 00/34506 | 6/2000 |
| WO | WO-00/35900 A1 | 6/2000 |
| WO | WO 01/20002 | 3/2001 |
| WO | WO 03/040100 | 5/2003 |
| WO | WO 03/066611 | 8/2003 |

(Continued)

OTHER PUBLICATIONS

Masuda-Nishimura, I., et al., "Development of a rapid positive/absent test for coliforms using sensitive bioluminescence assay", Lett. Appl. Microbiol.; 30, (2000), 130-135.

Miska, W., et al., "Synthesis and characterization of luciferin derivatives for use in bioluminescence enhanced enzyme immunoassays", Journal of Clinical Chemistry and Clinical Biochemistry, vol. 25, (1987), 23-30.

"5' Labeling—fluorescein and cyanine dyes, biotin," Glen Report, http://www.glenres.com/GlenReports/GR8-2.pdf (Published online by Glen Research, Sterling, VA), (Dec. 1995) 8(2):8 pages.

"Amplex Red monoamine oxidase assay kit (A12214)," Molcular Probes (Oct. 1, 2004) 4 pages, retrieved from the Internet: http://probes.invitrogen.com/media/pis/mp12214.pdf.

Abyshev, A.Z. et al., "Preparation and antiviral effect of benzopyran-2-one derivatives," Khimiko-Farmatsevticheskii Zhurnal (1996) 30(7):17-19; Database CA Accession No. 125:237748.

Allen, T. et al., "Cloning and expression fo the adenine phophoribosyltransferase gene from *Leishmania donovani*," Mol. Biochem. Parasitology (1995) 74:99-103.

Amess, R. et al., "Synthesis of luciferin glycosides as substrates for novel ultrasensitive enzyme assays," Carbohydrate Research (1990) 205:225-233.

(Continued)

Primary Examiner — Laura L. Stockton  
(74) Attorney, Agent, or Firm — Michael Best & Friedrich LLP

(57) ABSTRACT

Described herein are antibacterial compounds, methods for making the compounds, pharmaceutical compositions containing the compounds and methods of treating bacterial infections utilizing the compounds and pharmaceutical compositions.

20 Claims, 19 Drawing Sheets

FOREIGN PATENT DOCUMENTS

| | | | |
|---|---|---|---|
| WO | WO 2004/027378 | * | 4/2004 |
| WO | WO-2006/130551 A2 | | 12/2006 |
| WO | WO 2010/021686 | | 2/2010 |

OTHER PUBLICATIONS

Aparna, M.V.L. et al., "Synthesis and 5-HT2A antagonist activity of some 7-(3-aminopropoxy)-4-methyl-chromen-2-ones," Indian J. Pharm. Sci. (2005) 67(4):467-472; Database CA Accession No. 145:62752.

Beilstein Registry No. 1007132, Database Crossfire Beilstein, White, E.H. et al., J. Org. Chem. (1966) 31:1484-1488 (2 pages).

Beilstein Registry No. 1034055, Database Crossfire Beilstein, (McCapra, F. et al., Chem. Commun., 1968) 22-23, 1 page).

Beilstein Registry No. 1041968, Database Crossfire Beilstein, White et al., Bioorg. Chem. (1971) 1:92-116 (2 pages).

Beilstein Registry No. 1119094, Database Crossfire Beilstein, Benkoe, et al., Montsh. Chem. (1975) 106:1027-1032 (3 pages).

Beilstein Registry No. 1119095, Database Crossfire Beilstein, Benkoe, A. et al., Monatsh. Chem. (1975) 106:1027-1032 (2 pages).

Beilstein Registry No. 1126922, Datbsase Crossfire Beilstein, Benkoe et al., Monatsh. Chem. (1975) 106:1027-1032 (3 pages).

Beilstein Registry No. 1129927, Database Crossfire Beilstein, Benkoe et al., Monatsh. Chem. (1975) 106:1027-1032 ( 2 pages).

Beilstein Registry No. 30484, Database Crossfire Beilstein, White et al., J. Am. Chem. Soc. (1963) 85:337-343 (12 pages).

Beilstein Registry No. 3984932, Database Crossfire Beilstein, White et al., J. Org. Chem. (1965) 30:2344-2348 (2 pages).

Beilstein Registry No. 4240164, Database Crossfire Beilstein, Arness, R. et al., Carbohydr. Res. (1990) 1(1):225-233 (2 pages).

Beilstein Registry No. 926292, Database Crossfire Beilstein, White et al., J. Org. Chem. (1965) 30:2344-2348 (2 pages).

Ben-Shlomo, Y. et al., "Using monoamine oxidase Type B inhibitors in Parkinson's disease," BMJ (2004) 329:581-582.

Benet, L.Z. et al., "Pharmacokinetics The Dynamics of drug absorption, distribution and elimination," Introduction and Chapter 1 of The Pharmacological Basis of Therapeutics, 9th Edition, McGraw Hill (1996) 1-27 (was previously listed as: Hardman, J.g. et al., eds. The Pharmacological Basis of Therapeutics, 9th Edition, mcGraw-Hill (1996) 1-27).

Binda, C. et al., "Structure-function relationships in flavoenzyme-dependent amine oxidations—a comparison of polyamine oxidase and monoamine oxidase," J. Biol. Chem. (2002) 277(27):23973-23976.

Black, S.D. et al., "P-450 cytochromes: structure and function," Adv. Enzymol. Relat. Areas Mol. Biol. (1987) 60:35-87.

Bowie, L.J. et al., "Synthesis of a new substrate analog of firefly luciferin," Biochemistry (1973) 12(10):1845-1852.

Branchini, B.R., "Naphtyl- and quinolylluciferin: green and red light emitting firefly luciferin analogues," Photochem. Photobiol. (1989) 49(5):689-695.

Carlile, D.J. et al., "In vivo clearrance of ethoxycoumarin and its prediction from in vitro systems," Drug Metabolism and Disposition (1998) 26(3):216-221.

Charng, Y. et al., "Molecular cloning and expression of the gene encoding ADP-glucose phrophosphorylase from the Cyanobacterium anabaena sp. strain PCC 7120," Plant Mol. Biol. (1992) 20:37-47.

Chemistry 2131: organic Chemistry for the Life Sciences (3), http://www.mta.ca/~acockshu/c2131elimination.html (Mount Allison University), observed Dec. 17, 2004 (3 pages).

Chen, K. et al., "R1, a novel repressor of the human monoamine oxidase A," J. Biol. Chem. (2005) 280(12):11552-11559.

Craig, F.F. et al., "Membrane-permeable luciferin esters for assay of firefly luciferase in live intact cells," Biochem. J. (1991) 276(3):637-641.

Database Accession No. 4240164, Database Crossfire Beilstein, Beilstein Institute zur Foerderung der chemischen Wissenschafter, Frankfurt am Main, Germany (1991) 2 pages).

Demir, B. et al., "Platelet monoamine oxidase activity in alcoholism subtypes: relationship to personality traits and executive functions," Alcohol & Alcoholism (2002) 37(6):597-602.

Dukhovich, A. et al., "Time course of luciferyl adenylate synthesis in the firefly luciferase reaction," FEBS Lett. (1996) 395(2-3):188-190.

Eriksson, J. et al., "Method for real time detectino of inorganic pyrophosphatase activity," Anal. Biochem. (2001) 293(1):67-70.

Farace, C. et al., "Synthesis and characterization of a new substrate of photinus pyralis luciferase: 4-methyl-D-luciferin," J. Clin. Chem. Clin. Biochem. (1990) 28(7):471-474.

Feldmann, R. et al., "Decreased metabolism and viability of mycoplasma hominis induced by monoclonal antibody-mediated agglutination," Infection and Immunity (1992) 60(1):166-174.

Flickinger, B., "Using metabolism data in early development," Drug. Disc. Dev. (2001) 4(( ):53-56.

Gabelova, A. et al., "Mutagenicity of 7H-dibenzo[c,g]carbazole and its tissue specific derivatives in genetically engineered chinese hamster V79 cell lines stably expressing cytochrome P450," Mutation Research (2002) 517:135-145.

Gandelman, O. et al., "Cytoplasmic factors that affect the intensity and stability of bioluminescence from firefly luciferase in living mammalian cells," J. Biolum. Chemilumin. (1994) 9(6):363-371.

Garrido-Hernandez, H. et al., "Design and synthesis of phosphotyrosine peptidomimetic prodrugs," J. Med. Chem. (2006) 49:3368-3376.

Gomez-Lechon, M. et al., "Expression and induction of a large set of drug-metabolizing enzymes by the highly differentiated human hepatoma cell line BC2," Eur. J. Biochem. (2001) 268:1448-1459.

Graham-Lorence, S. et al., "P450s: structural similarities and functional differences," FASEB J. (1996) 10:206-214.

Guengerich, F.P., "Common and uncommon cytochrome P-450 reactions related to metabolism and chemical toxocity," Chem. Res. Tox. (2001) 14(6):611-650.

Gutierrez, M.C. et al., "The first fluorogenic assay for detecting a baeyer-villigerase activity in microbial cells," Org. Biomol. Chem. (2003) 1:3500-3506.

Hawkins, E.M. et al., "Coelenterazine derivatives for improved sollution stability," Luminescene, Proceedings of the International Symposium on Bioluminescence and Chemiluminescence, (2002) 17:91-92 (Abstract only).

Holt, A., "Imidazoline binding sites on receptors and enzymes: emerging targets for novel antidepressant drugs?" J. Psychiatry Neurosci. (2003) 28(6):409-414.

Hynson, R.M.G. et al., "Conformational changes in monoamine oxidase A in response to ligand binding or reduction," Biochimica et Biophysica Acta (2004) 1672:60-66.

Inouye, S. et al., "The use of renilla luciferase, oplophorus luciferase, and apoaequorin as bioluminscent reporter rpotein in the presence of coelenterazine analogues as substrate," Biochem. Biophys. Res. Comm. (1997) 233:349-353.

Jagadeeswaran, P. et al., "Nucleotide sequence and analysis of deletion mutants of the Escherichia coli gpt gene in plasmid pSV2 gpt," Gene (1996) 31:309-313.

Jiang, Y. et al., "Crithidia fasciculata: isolation, sequencing and expression of the hypoxanthine-guanine phosphoribosyltransferase gene," Exp. Parasitology (1996) 82:73-75.

Kalmar, G. et al., "cloning and expression of rat liver CTP-:phosphocholine cytidylyltransferase: a ampipathetic protein that controls phophatidylcholine synthesis," Proc. Natl. Acad. Sci. USA (1990) 87:6029-6033.

Katz, I.R. et al., "Monoamine oxidase, an intracellular probe of oxygen pressure in isolated cardiac myocytes," J. Biol. Chem. (1984) 259(12):7504-7509.

Kelly, J.H. et al., "A fluorescent cell-based assay for cytochrome P-450 isozyme 1A2 induction and inhibition," J. Biomol. Screening (2000) 5(4):249-253.

Kim, D. et al., "Molecular cloning of cucumber phosphoenolpyruvate carboxykinase and development regulation of gene expression," Plant Mol. Biol. (1994) 26:423-434.

Kim, J.J. et al., "Selective enhancement of emotional, but not motor, learning in monoamine oxidase A-deficient mice," Proc. Natl. Acad. Sci. USA (1997) 94:5929-5933.

Ladror, U. et al., "Cloning, sequencing and expressino of pyrophosphate-dependent phosphofructokinase from Propionibacterium freudenreichii," J. Biol. Chem. (1991) 266(25):16550-16555.

Leemann, T. et al., "Cytochrome P450TB (CYP2C): a major monooxygenase catalyzing diclofenac 4'-hydroxylation in human liver," Life Sci. (1993) 52(1):29-34.
Lembert, N., "Firefly luciferase can use L-luciferin to produce light," Biochem. J. (1996) 317(Pt. 1):273-277.
Leyh, T. et al., "The sulfate activation locus of *Escherichia coli* K12: cloning, genetic, and enzymatic characterization," J. Biol. Chem. (1988) 263(5):2409-2416.
Li, A.P., "Evaluation of luciferin-isopropyl acetal as a CYP3A4 substrate for human hepatocytes: effects of organic solvents, cytochrome P450 (P450) inhibitors, and P450 inducers," Drug Metabolism and Disposition (2009) 37(8):1598-1603.
Ludin, K. et al., "The Ade4 gene of *Schizosaccharomyces pombe*: cloning, sequence and regulation," Curr. Genet. (1994) 25:465-468.
Mancy, A. et al., "Diclofenac and its derivatives as tools for studying human cytochromes P450 active sites: particular efficiency and regioselectivity of P450 2Cs," Biochem. (1999) 38:14264-14270.
Markaglou, N. et al., "Immobilized enzyme reactors based upon the flavoenzymes monamine oxidase A and B," J. Chromatog. B (2004) 804:295-302.
Marolda, C. et al., "Identification, expression and DNA sequence of the GDP-mannose biosynthesis genes encoded by the 07 rfb gene cluster of strain VW 187 (*Escherichia coli* 07:k1)," J. Bacteriol. (1993) 175(1):148-158.
Masuda-Nishimura, I. et al., "Development of a rapid postive/abstent test for coliforms using sensitive bioluminescence assay," Lett. Appl. Microbiol. (2000) 30(2):130-135.
Miller, V.P. et al., "Fluorometric high-throughput screenign for inbitors of cytochrome P450," Ann. NY Acad. Sci. (2000) 919:26-32.
Miska, w. et al., "A new type of ultrasensitive bioluminogenic eynzyme substrates, I. Enzyme substrates with D-luciferin as leaving group," Biol. Chem. Hoppe-Seyler (1998) 369(5):407-411.
Miska, W. et al., "Evaluation of the bioluminescence-enhanced zona binding assay," Biolum. Chemilum.: Mol. Reporting with Protons, Proceedings fo the International Symposium on Bioluminescence and Chemiluminescence, Oct. 4-8, 1996, pp. 315-318.
Mitani, M. et al., "Chemiluminescent assay of beta-D-galactosidase using cypridina luciferin analogue: 3-(Beta-D-galactopyranosyloxy)-6-(4-methoxyphenyl)-2-methyl-imidazol[1,2-alpha]pyrazine," Anal. Sci. (1994) 10(50:813-814.
Monsees, T. et al., "A novel bioluminogenic assay for alpha-chymotrypsin," J. Biolumin. Chemilumin. (1995) 10(4):213-218.
Monsees, T. et al., "Synthesis and characterization of a bioluminogenic substrate for alpha-chymotrypsin," Anal. Biochem. (1994) 221(2):329-334.
Muller-Rober, B. et al., "Isolation and expression analysis of cDNA clones encoding a small and a large subunit of ADP-glucose pyrophosphorylase from sugar beet," Plant Mol. Biol. (1995) 27:191-197.
Nakagawa, S. et al., "Nucleotide sequence of the FAD synthetase gene from *Corynebacterium ammoniagenes* and its expression in *Escherichia coli*," Biosci. Biotech. Biochem. (1995) 59(4):694-702.
Nelson, D.R. et al., "P450 superfamily: update on new sequences, gene mappin, accession numbers and nomenclature," Pharmacogenetics (1996) 6:1-42.
Nicolaus, B.J., "Symbiotic approach to drug design," Decision making in Drug Research (1983) 173-186.
O'Brien, M.A. et al., "Homogeneous, bioluminescent protein assays: caspase-3 as a model," J. Biomol. Screen. (2005) 10(2):137-148.
Phillips, I.R. et al., "Preface: Cytochrome P450 protocols," Methods in Mol. Biol. (1998) 107:v-vi.
Pla, J. et al., "Cloning of the *Candida albicans* H1S1 gene by direct complementation of a *C. albicans* histidine auxotroph using an improved double-ARS shuttle vector," Gene (1995) 165:115-120.
Promega Corporation, "P450-Glo™ Assays," Technical Bulletin No. 325, Madison, Wisconsin (Jun. 2003) 19 pages.
Rahman, A. et al., "Selective biotransformation of taxol to 6 alpha-hydroxytaxol by human cytochrome P450 2C8," Cancer Res. (1994) 54(21):5543-5546.
Renwick, A.B. et al., "Evaluation of 7-benzyloxy-4-trifluoromethyl-coumarin, some other 7-hydroxy-4-trifluoro-methylcoumarin derivatives and 7-benzyloxyquinoline as fluorescent substrates for rat hepatic cytochrome P450 enzymes," Xenobiotica (2001) 31(12):861-878.
Rose, A. et al., "A phosphoribosylanthranilate transferase gene is defective in blue fluorescent *Arabidopsis thaliana* tryptophan mutants," Plant Physiol. (1992) 100:582-592.
Sai Y. et al., "Assessment of specificity of eight chemical inhibitors using cDNA-expressed cytochrome P450," Xenobiotica (2000) 30(4):327-343.
Salles, C. et al., "Biochemical characteristics of liver and brain monoamine oxidase from pacu," J. Fish Biol. (2001) 58:1301-1310.
Shanmugam, K. et al., "Purification and characterization of a tRNA nucleotidyltransferase from *Lipinus albus* and fucntional complementation of a yeast mutation by the corresponding cDNA," Plant Mol. Biol. (1996) 30:281-295.
Shimomura, O. et al., "Semi-synthetic aequorins with improved sensitivity to Ca2+ ions," Biochem. J. (1989) 261:913-920.
Shinde, N.D. et al., "Synthesis of some sulfonamido and amino alkanes and their antifungal activity," Asian J. Chem. (1996) 8(1):85-90, Database CA Accession No. 124:232194.
Shou, M. et al., "A kinetic model for the metabolic interaction of two substrates at the active site of cytochrome P450 3A4," J. Biol. Chem. (2001) 276(3):2256-2262.
Stresser, D.M. et al., "Cytochrome P450 flourometric substrates: identification of isoform-selective probes for rat CYP2D2 and human CYP3A4," Drug and Disposition (2002) 30(7):845-852.
Sussman, H.E. et al., "Choosing the best reporter assay," The Scientist (Jul. 23, 2001) 25-27 (retrieved from the Internet, http:www.the-scientist.com/article/display/12529/profile2_010723.html.
Takahashi, S. et al., "Benzimidazole N-oxide. VIII. The reactivity of ethyl 1-methyl-2-benzimidazolecarboxylate 3-oxide and related compounds," Chem. Pharm. Bull. (1968) 16(3):527-538.
Tassaneeyakul, W. et al., "Specificity of substrate and inhibitor probes for human cytochromes P450 1A1 and 1A2," J. Pharmacol. Exp. Ther. (1993) 265(1):401-407.
Teranishi, K. et al., "Coelenterazine analogs as chemiluminescent probe for superoxide anion," Anal. Biochem. (1997) 249:37-43.
Toya, Y. et al., "Improved synthetic methods of firefly luciferin derivatives for use in bioluminescent analysis of hydrolytic enzymes: carboxylyic esterase and alkaline phosphatase," Bulletin of the Chemical Society of Japan (1992) 65(10):2604-2610.
Ubeaud, G. et al., "Estimation of flavin-containing monooxygenase activity in intact hapatoxyte monolayers or rat, hamster, rabbit, dog and human by using N-oxidation of benzydamine," Eur. J. Pharm. Sci. (1999) 8:255-260.
Van Vleet, T. et al., "Metabolism and cytotoxicity of aflatoxin B1 in cytochrome P-450-expressing human lung cells," J. Toxicolog. Environ. Health (2002) 65:853-867.
Vinitsky, A. et al., "Cloning and nucleic acid sequence of the *Salmonella typhimurium* pncB gene and structur of nicotinate phosphoribosyitransferase," J. Bacteriol. (1991) 173(2):536-540.
Vonstein, V. et al., "Molecular cloning of the pyrE gene from the extreme thermophile *Thermus flavus*," J. Bacteriol. (1995) 177(8):4540-4543.
Wahler, d. et al., "Enzyme fingerprints of activity, and stereo- and anantionselectivity from fluorogenic and chromogenic substrate arrays," Chem. A European Journal. (2002) 8(14):3211-3228.
White, E.H. et al, "Analogues of firefly luciferin, III," J. Org. Chem. (1966) 31:1484-1488.
White, E.H. et al., "Analogs of firefly luciferin," J. Org. Chem. (1965) 30:2344-2348.
Wood, K.A., "Engineering luciferase enzymes and substrates for novel assay capabilities," Proceedings of SPIE—Microarrays and Combinatorial Techniques: Design, Fabrication and Analysis II (Jun. 2004) 5328:69-77.
Wrighton, S.A. et al., "The human hepatic cytochromes P450 involved in drug metabolism," Crit. Rev. Toxicol. (1992) 22(1):1-21.
Yang, J. et al., "An easily synthesized photolyzable luciferase for in vivo luciferase activity measurement," Biotechniques (1993) 15(5):848-850.
Yang, X. et al., "Homogeneous enzyme immunoassay modified for application to luminescence-based biosensors," Anal. Biochem. (2005) 336:102-107.

Yoshitomi, S. et al., "Establishment of the transformants expressing human cytochrome P450 subtypes in HepG2, and their applications on drug metabolism and toxicology," Toxicology in Vitro (2001) 15:245-256.

Youdin, M.B. et al., "Novel substrates and products of amine oxidase-catalysed reactions," Biochem. Soc. Trans. (1990) 19:224-228.

Yun, B-S et al., "Coumarins with monamine oxidase inhibitory activity and antioxidative coumarino-lignans from *Hibiscus syriacus*," J. Natl. Prod. (2001) 64(9):1238-1240.

Yun, C-H. et al., "Rate-determining steps in phenacetin oxidations by human cytochrome P450 1A2 and selected mutants," Biochem. (2000) 39:11319-11329.

Zapata, G. et al., "Sequence of the cloned *Escherichia coli* K1 CMP-N-acetylneuraminic acid synthetase gene," J. Biol. Chem. (1989) 264(25):14769-14774.

Zhou, G. et al., "Platelet monoamine oxidase B and plasma beta-phenylethylamine in Parkinson's disease," J. Neurol. Neurosurg. Psychiatry (2001) 70:229-231.

Zhou, M. et al., "A one-step fluorometric method for the continuous measurement of monoamine oxidase activity," Anal. Biochem. (1997) 253:169-174.

Zhou, M. et al., "A stable nonfluorescent derivative of resorufin for the fluorometric determination of trace hydrogen peroxide: applications in detecting the activity of phagocyte NADPH oxidase and other oxidases," Anal. Biochem. (1997) 253:162-168.

Zhou, W. et al., "New bioluminogenic substrates for monoamine oxidase assays," J. Am. Chem. Soc. (2006) 128(10):3122-3123.

International Preliminary Examination Report for Application No. PCT/US03/29078 dated Oct. 19, 2006 (6 pages).

International Preliminary Report on Patentability for Application No. PCT/US06/020731 dated Sep. 12, 2007 (8 pages).

International Search Report for Application No. PCT/US03/29078 dated Oct. 8, 2004 (4 pages).

International Search Report for Application No. PCT/US2006/020731 dated Mar. 13, 2007 (17 pages).

Partial International Search Report for Application No. PCT/US2006/020731 dated Oct. 2, 2006 (6 pages).

International Search Report and Written Opinion for Application No. PCT/US2009/004696 dated Nov. 19, 2009 (13 pages).

United States Patent Office Action for U.S. Appl. No. 10/665,314 dated Jan. 15, 2009 (6 pages).

United States Patent Office Action for U.S. Appl. No. 10/665,314 dated Jul. 18, 2008 (14 pages).

United States Patent Office Action for U.S. Appl. No. 10/665,314 dated Mar. 19, 2008 (5 pages).

United States Patent Office Action for U.S. Appl. No. 10/665,314 dated May 15, 2009 (6 pages).

United States Patent Office Action for U.S. Appl. No. 10/665,314 dated Oct. 11, 2007 (16 pages).

United States Patent Office Action for U.S. Appl. No. 10/665,314 Advisory Action mailed Jun. 6, 2008 (3 pages).

United States Patent Office Action for U.S. Appl. No. 11/444,145 dated Apr. 28, 2009 (15 pages).

United States Patent Office Action for U.S. Appl. No. 11/444,145 dated Mar. 24, 2008 (16 pages).

United States Patent Office Action for U.S. Appl. No. 11/444,145 dated Oct. 15, 2008 (16 pages).

United States Patent Office Action for U.S. Appl. No. 11/444,145 dated Dec. 3, 2009 (27 pages).

United States Patent Office Action for U.S. Appl. No. 11/444,145 dated Jul. 20, 2010 (14 pages).

United States Patent Office Notice of Allowance for U.S. Appl. No. 11/444,145 dated Jan. 24, 2011 (19 pages).

United States Patent Office Action for U.S. Appl. No. 12/217,494 dated Dec. 16, 2009 (18 pages).

United States Patent Office Action for U.S. Appl. No. 12/217,494 dated Jun. 28, 2010 (10 pages).

United States Patent Office Action for U.S. Appl. No. 12/217,374 dated Jul. 28, 2010 (8 pages).

United States Patent Office Action for U.S. Appl. No. 12/217,374 dated Dec. 17, 2010 (9 pages).

United States Patent Office Action for U.S. Appl. No. 12/217,374 dated May 24, 2011 (8 pages).

United States Patent Office Action for U.S. Appl. No. 12/754,164 dated May 13, 2011 (5 pages).

United States Patent Office Notice of Allowance for U.S. Appl. No. 12/754,164 dated Sep. 21, 2011 (5 pages).

Geiger, R. et al., "A new ultrasensitive bioluminogenic enzyme substrate for beta-galactosidase," Biol. Chem. Hoppe-Seyler (1992) 373:1187-1191.

White, E.H. et al., "Amino analogs of firefly luciferin and biological activity thereof," J. Amer. Chem.. Soc. (1966) 88(9):2015-2018.

United States Patent Office Action for U.S. Appl. No. 12/217,494 dated Jan. 26, 2012 (14 pages).

* cited by examiner

LUMINOGENIC COMPOUNDS AND METHODS TO DETECT CYTOCHROME P450 3A ENZYMES

This application claims priority to U.S. Provisional Application No. 61/089,818 filed on Aug. 18, 2008, which is hereby incorporated by reference.

BACKGROUND

Luminescence is produced in certain organisms as a result of a luciferase-mediated oxidation reaction. Luciferase genes from a wide variety of vastly different species, particularly the luciferase genes of *Photinus pyralis* and *Photuris pennsylvanica* (fireflies of North America), *Pyrophorus plagiophthalamus* (the Jamaican click beetle), *Renilla reniformis* (the sea pansy), and several bacteria (e.g., *Xenorhabdus luminescens* and *Vibrio* spp), are extremely popular luminescence reporter genes. Firefly luciferase is also a popular reporter for determining ATP concentrations, and, in that role, is widely used to detect biomass. Luminescence is also produced by other enzymes when those enzymes are mixed with certain synthetic substrates, for instance, alkaline phosphatase and adamantyl dioxetane phosphate, or horseradish peroxidase and luminol.

Luciferase genes are widely used as genetic reporters due to the non-radioactive nature, sensitivity, and extreme linear range of luminescence assays. For instance, as few as 10-20 moles of firefly luciferase can be detected. Consequently, luciferase assays of gene activity are used in virtually every experimental biological system, including both prokaryotic and eukaryotic cell cultures, transgenic plants and animals, and cell-free expression systems. Similarly, luciferase assays used to determine ATP concentration are highly sensitive, enabling detection to below 10-16 moles.

Luciferases can generate light via the oxidation of enzyme-specific substrates, e.g., luciferins. For firefly luciferase and all other beetle luciferases, light generation occurs in the presence of luciferin, magnesium ions, oxygen, and ATP. For anthozoan luciferases, including *Renilla* luciferase, only oxygen is required along with the substrate coelenterazine. Generally, in luminescence assays to determine genetic activity, reaction substrates and other luminescence activating reagents are introduced into a biological system suspected of expressing a reporter enzyme. Resultant luminescence, if any, is then measured using a luminometer or any suitable radiant energy-measuring device. The assay is very rapid and sensitive, and provides gene expression data quickly and easily, without the need for radioactive reagents.

Because most enzymatic reactions do not generate outputs that are as ideal as luciferase, the availability of a luciferase mediated assay for enzymatic reactions useful in cellular analysis and high-throughput screening applications would be desirable to those working in this field. The development of such a luciferase mediated reaction as the basis for such enzymatic or biological assays has, however, been limited. Luciferase mediated reactions have been employed to detect numerous other molecules, e.g., ATP or lactate dehydrogenase. For some of those reactions, a derivative of the naturally occurring substrate is employed. Native firefly luciferin, a polyheterocyclic organic acid, D-(-)-2-(6'hydroxy-2'-benzothiazolyl)-Δ2-thiazolin-4-carbozylic acid, is shown in FIG. 1. For instance, methods for using luciferin derivatives with a recognition site for an enzyme such as a protease as a prosubstrate were described by Miska et al. (Journal of Clinical Chemistry and Clinical Biochemistry, 25:23 (1987)). The heterogeneous assays were conducted by incubating the luciferin derivative with the appropriate enzyme, e.g., a protease, for a specified period of time, then transferring an aliquot of the mixture to a solution containing luciferase. Masuda-Nishimura et al. (Letters in Applied Microbio., 30:130 (2000)) reported the use of a single tube (homogenous) assay which employed a galactosidase substrate-modified luciferin. In these luciferin derivatives, the portion of the derivative functioning as the reactive group for the nonluciferase enzyme activity was coupled to the D-luciferin or aminoluciferin backbone such that upon the action of the nonluciferase enzyme, a D-luciferin or aminoluciferin molecule was produced as the direct product of the reaction to serve as the substrate for luciferase. A primary obstacle to broadly applying luciferase mediated reactions for other enzymatic assays has been the belief that to modify the luciferin molecule to function as a substrate for a nonluciferase enzyme, the activity of the nonluciferase enzyme must directly yield a D-luciferin or aminoluciferin molecule to retain its function as a substrate for luciferase.

SUMMARY

The present invention provides acetal derivatives of luciferin and methods for using such derivatives in enzyme activity assays where the luciferin derivative serves as a substrate for a desired enzyme and is a prosubstrate for luciferase (a proluciferin). Thus, by providing luciferin derivatives having a particular enzyme recognition site for a desired nonluciferase enzyme (a reactive chemical group in a molecule referred to as a substrate for the enzyme) coupled to the luciferin backbone (or other chemical moiety constituting a suitable substrate for luciferase), e.g., derivatives having modifications at the carboxyl group of D-luciferin or aminoluciferin as well as optionally other modifications, nonluciferase enzymes may be measured in a bioluminescent assay.

Modifications of luciferin within the scope of the derivatives of this invention include one or more substitutions of a ring atom, one or more substitutions of a substituent (atom or group) attached to a ring atom, and/or addition of one or more atoms to the ring, e.g., expansion or addition of rings, or a combination thereof. Numbering for some of the ring atoms in D-luciferin is shown in FIG. 1. Native firefly luciferin has three linked rings, a 6 membered ring having an OH group at position 6 ("ring A" or "A ring" hereinafter), a 5 membered thiazole ring linked to the 6 membered ring ("ring B" or "B ring" hereinafter), and a 5 membered thiazole ring that is modified with a carboxyl group at position 5 ("ring C" or "C ring" hereinafter). The luciferin derivatives of the invention include at least one modification that replaces the carboxyl group on the C ring with an acetal group. For instance, a luciferin derivative with an A ring modification may have a substitution of a C atom in the A ring with another atom, addition of a ring, a substitution of a substituent attached to a ring atom with a different atom or group, or any combination thereof. A luciferin derivative with a B ring modification may have an addition to or substitution of an atom in the five membered ring, e.g., insertion of one or more atoms, thereby expanding the ring, for instance, to a six membered ring, substitution of N or S in the ring with a different atom, e.g., a C or O, substitution of a substituent atom or group attached to a ring atom, or any combination thereof. A luciferin derivative with a C ring modification may have a substitution of an atom in the ring with another atom, a substitution of a substituent attached to a ring atom, with a different atom or group, or any combination thereof. A derivative of the invention may be modified at more than one position, for instance, the derivative may have two (or more) A ring modifications, two (or more) B ring modifications, two (or more) C ring modifications, or any combination thereof.

In one embodiment, in addition to an acetal group, luciferin derivatives include those in which the backbone of luciferin is modified in its ring structure, e.g., a quinolyl or naphthyl luciferin, or include a halogen in ring A. The use of derivatives with the acetal modification provide for or improve assays for certain nonluciferase enzymes or molecules, e.g., by increasing the signal, decreasing the background, increasing selectivity and/or decreasing the $K_m$. Thus, bioluminescent methods that employ a luciferin derivative of the invention may be used to detect one or more molecules, e.g., an enzyme, a cofactor for an enzymatic reaction, an enzyme substrate, an enzyme inhibitor, or an enzyme activator.

As described herein, a compound of the invention had increased signal and lower background, and provided for an assay that was more sensitive in detecting basal levels and had enhanced selectivity for CYP3A4 activity (when employed at 2 μM, the $K_m$) compared to other luminogenic CYP3A4 substrates. Moreover, the activity of CYP3A4 in a reaction with a compound of the invention was inhibited by testosterone, ketoconazole, nifedipine, and midazolam. Such a compound is a broad spectrum probe for inhibitors of CYP3A and is useful to detect agents that do not inhibit 3A activity with narrower spectrum probes. Further, the reaction proceeded more rapidly when a compound of the invention was employed in the methods, e.g., $k_{cat}$ of about 1.4/minute versus about 15/minute (see Cali et al. Luminogenic Cytochrome P450 Assays. *Exp. Op. Drug Metab. Toxicol.* (2006) 2(4): 629-645).

The luciferin derivatives of the invention having at least one modification that replaces the carboxyl group on the C ring with an acetal group may be a substrate for a cytochrome P450 enzyme, flavin monooxygenase (FMO), peroxidase or other enzyme or reactive oxygen species such as a compound that has an oxygen ion or radical. In addition, the luciferin derivative may also include modifications that yield a substrate for monoamine oxidase (MAO), or other cytochrome P450 enzymes, glutathione S transferase (GST), dealkylase, deacetylase, deformylase, phosphatase, e.g., alkaline phosphatase (AP), sulfatase, beta-lactamase, alcohol dehydrogenase, protease e.g., proteosome, cathepsin, calpain, beta secretase, thrombin, or granzyme, or is useful to detect reactive oxygen species (ROS), peroxidase, e.g., horseradish peroxidase (HRP), and redox conditions, see, e.g., U.S. published application No. 2007/0015790, the disclosure of which is incorporated by reference herein. These additional modifications are to the A ring or B ring, as described above.

In one embodiment, the invention provides a compound of formula I:

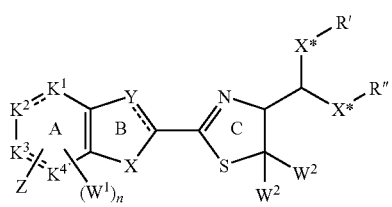

(I)

wherein
Y is N,N-oxide, N—$(C_1-C_6)$alkyl, or CH;
X is S, O, CH═CH, N═CH, or CH═N;
each X* is independently O or S;

R' and R" are independently $(C_1-C_{20})$alkyl, $(C_2-C_{20})$alkenyl, $(C_2-C_{20})$alkynyl, $(C_3-C_{20})$cycloalkyl, $(C_6-C_{30})$aryl, heteroaryl, heterocycle, and may be optionally substituted with hydroxyl, $(C_1-C_{12})$alkoxy, oxy, amino, halo, carboxyl, thio, $(C_6-C_{30})$aryl, heteroaryl, or heterocycle, or R' and R" together form a cyclic species;

Z is H, OR, OH, $NH_2$, NHR, or NRR;

$W^1$ is H, halo, $(C_1-C_6)$alkyl, $(C_2-C_{20})$alkenyl, hydroxyl, or $(C_1-C_6)$alkoxy; and n is 1, 2, or 3; or a $W^1$ and Z together form a keto group on ring A, and at least one of the dotted lines denoting optional bonds in ring A is absent;

each $W^2$ is independently H, halo, $(C_1-C_6)$alkyl, $(C_2-C_4)$ alkenyl, hydroxyl, or $(C_1-C_6)$alkoxy;

each of $K^1$, $K^2$, $K^3$, and $K^4$ is independently CH, N,N-oxide, or N—$(C_1-C_6)$alkyl, and the dotted lines between $K^1$ and $K^2$, and $K^3$ and $K^4$, denote optional bonds; and when the carbon of any CH is substituted, the H is absent;

the dotted line in ring B is an optional double bond;

each R is independently H, $(C_1-C_{20})$alkyl, $(C_2-C_{20})$alkenyl, $(C_2-C_{20})$alkynyl, $(C_3-C_{20})$cycloalkyl, $(C_1-C_{12})$alkoxy, $(C_6-C_{30})$aryl, aryl$(C_1-C_{20})$alkyl, heteroaryl, heterocycle, $(C_1-C_{20})$alkylsulfonyl, $(C_6-C_{30})$arylsulfonyl, heteroarylsulfonyl, $(C_1-C_{20})$alkylsulfinyl, $(C_6-C_{30})$arylsulfinyl, heteroarylsulfinyl, $(C_1-C_{20})$alkoxycarbonyl, amino, NH$(C_1-C_6)$alkyl, N$((C_1-C_6)$alkyl$)_2$, tri$(C_1-C_{20})$ammonium$(C_1-C_{20})$alkyl, heteroaryl$(C_1-C_{20})$alkyl, heteroaryl having quaternary nitrogen, heteroarylcarbonyl having quaternary nitrogen, $(C_6-C_{30})$ arylthio, $(C_1-C_{20})$alkylphosphate, $(C_1-C_{20})$alkylphosphonate, $(C_6-C_{30})$arylphosphate, $(C_6-C_{30})$arylphosphonate, phosphate, sulfate, or saccharide;

or when Z is NRR, RR together with the N to which they are attached optionally form a heteroaryl or heterocycle group;

wherein any alkyl, alkenyl, alkynyl, cycloalkyl, alkoxy, amino, aryl, heteroaryl, or heterocycle group is optionally substituted with 1, 2, 3, 4, or 5 substituents selected from $(C_1-C_{20})$alkyl, $(C_2-C_{20})$alkenyl, $(C_2-C_{20})$alkynyl, $(C_3-C_{20})$ cycloalkyl, $(C_1-C_{20})$alkoxyl, $(C_1-C_{20})$alkylcarbonyl, $(C_1-C_{20})$alkylcarboxyl, halo, hydroxyl, —COO$R^x$, —S(O)$R^x$, —SO$_2R^x$, —SO$_3R^x$, nitro, amino, phosphate, $(C_1-C_{20})$alkylphosphate, $(C_1-C_{20})$alkylphosphonate, NH$(C_1-C_6)$alkyl, NH$(C_1-C_6)$alkynyl, N$((C_1-C_6)$alkyl$)_2$, N$((C_1-C_6)$alkynyl$)_2$, mercapto, $(C_1-C_{20})$alkylthio, $(C_6-C_{14})$aryl, $(C_6-C_{14})$arylthio, trifluoromethyl, ═O, heteroaryl, or heterocycle, and each substituent is optionally substituted with one to three R groups; wherein $R^x$ is H, $(C_1-C_6)$alkyl, $(C_6-C_{14})$aryl, heterocycle, or heteroaryl;

or a salt thereof;

when Z comprises a nitrogen moiety, one or both of the hydrogens of the Z nitrogen moiety may be replaced by $(C_1-C_{20})$alkyl or the group L, wherein L is an amino acid radical, a peptide radical having up to 20 amino acid moieties, or any other small molecule that is a substrate for a nonluciferase;

when Z is a hydroxyl group or a nitrogen moiety, H of the hydroxyl or nitrogen moiety may be replaced by (HO)$_2$P (O)—OCH$_2$—, sulfo, —PO$_3H_2$, or by a cephalosporanic acid attached to the group Z via a carbon chain of one to about 12 carbon atoms;

when Z is a hydroxyl group or a nitrogen moiety, one H of the hydroxyl or nitrogen moiety may be replaced by the group L'-linker, wherein L' is a group removable by an enzyme to free the linker, and linker is a carbon chain that can self-cleave, optionally interrupted by one or more nitrogen atoms, oxygen atoms, carbonyl groups, optionally substituted aromatic rings, or peptide bonds;

linker is attached to L' via an oxygen atom or an NH group at one terminus of the linker and the other terminus of the linker forms an ether, ester, or amide linkage with a group Z; and when Z is OR, formula I is optionally a dimer connected at the two A rings via a linker comprising a ($C_1$-$C_{12}$)alkyl diradical that is optionally interrupted by one to four O atoms, N atoms, or an optionally substituted aryl, heteroaryl, or heterocycle group to form a bridge between the dimer of formula I, and the R group of each Z group connecting the dimer of formula I is replaced by the bridge.

The use of the luciferin derivatives described herein can result in an assay which produces a measurable change in optical properties upon interaction with a nonluciferase molecule, which interaction may alter the structure of the luciferin derivative. As described herein, the product of a reaction between a luciferin derivative and a nonluciferase enzyme or other molecule of interest need not be D-luciferin or aminoluciferin. For example, a luciferin derivative may include a substrate that includes a reactive chemical group for a nonluciferase enzyme linked to luciferin or aminoluciferin via a chemical linker. Transformation of the reactive chemical group of the derivative by the nonluciferase enzyme may yield a product that contains (retains) a portion of the substrate, a portion of the chemical linker, the chemical linker, or a portion of the substrate and the chemical linker, and that product is a substrate or prosubstrate for a luciferase.

In one embodiment, a bioluminescent assay method to detect one or more nonluciferase enzymes is provided. The method includes contacting a sample suspected of having one or more nonluciferase enzymes, a substrate or a co-factor for the reaction, with a corresponding reaction mixture that includes a derivative of luciferin or a derivative of aminoluciferin of the invention that is a substrate for the nonluciferase enzyme.

Furthermore, the inclusion of a thiol compound with a luciferin derivative in a luciferase-mediated assay may effectively stabilize the luminescence of the reaction, thereby providing for "glow" kinetics, i.e., luminescent intensity of the luciferase-mediated reaction is relatively constant over time after addition of the derivative. Such compounds may also be used in bioluminogenic assays monitoring the presence or activity of nonluciferase enzymes or a nonenzymatic biological reaction.

If the derivative is a prosubstrate for luciferase, i.e., the product of a reaction between the derivative and the nonluciferase enzyme is a substrate for luciferase, sequential or concurrent reactions for the nonluciferase enzyme and the luciferase may be conducted. For instance, an assay for a nonluciferase enzyme that includes a luciferin derivative that is a prosubstrate for luciferase may be conducted in a single reaction vessel and a beetle luciferase reaction mixture added to that vessel. In another embodiment, a reaction mixture for an assay for a nonluciferase enzyme that includes a luciferin derivative that is a prosubstrate for luciferin may be conducted in a single reaction vessel, and a portion of that reaction added to a different vessel having a beetle luciferase reaction mixture. Alternatively, the nonluciferase and luciferase reactions may be conducted simultaneously in the same vessel.

The invention thus provides in an embodiment a method to detect or determine the presence or amount of a molecule for a nonluciferase enzyme-mediated reaction in a sample. The method includes contacting a sample, a first reaction mixture for a nonluciferase enzyme-mediated reaction, and a derivative of luciferin which is a substrate for the nonluciferase enzyme, so as to yield a first mixture comprising a luminogenic product that is a substrate for a luciferase. In one embodiment, the derivative is a compound of formula I. At least a portion of the first mixture is contacted with a second reaction mixture for a luciferase-mediated reaction, so as to yield a second mixture. Then, luminescence in the second reaction is detected or determined, thereby detecting or determining the presence or amount of a molecule for the nonluciferase enzyme-mediated reaction in the sample, e.g., compared to a control. In some embodiments, a second nonluciferase enzyme may be used to further chemically transform the product of the first nonluciferase enzyme-mediated reaction to yield a substrate for a luciferase. For example, the sample, the nonluciferase reaction mixture or the luciferase reaction mixture may include an esterase, or the esterase may be added separately.

In an alternate embodiment, a method to detect or determine the presence or amount of a molecule for a first nonluciferase enzyme-mediated reaction in a sample is provided wherein the method includes contacting a sample, a reaction mixture for a nonluciferase-mediated enzyme reaction and a luciferase-mediated reaction, and a derivative of luciferin which is a substrate for the nonluciferase enzyme, yielding a mixture. A reaction between the nonluciferase enzyme and the derivative yields a luminogenic product that is a substrate for the luciferase. Luminescence in the mixture is detected or determined, thereby detecting or determining the presence or amount of a molecule for the nonluciferase-mediated reaction in the sample.

Also provided is a method to identify a modulator of a nonluciferase enzyme-mediated reaction. The method includes contacting one or more agents, a first reaction mixture for a nonluciferase enzyme-mediated reaction, and a derivative of luciferin which is a substrate for the nonluciferase enzyme, so as to yield a first mixture, or providing such a mixture. The first mixture in the absence of the one or more agents includes a luminogenic product that is a substrate for a beetle luciferase. At least a portion of the first mixture and a second reaction mixture for a beetle luciferase-mediated reaction are mixed, so as to yield a second mixture. Luminescence in the second mixture is compared with a control mixture, thereby identifying whether one or more of the agents modulates the nonluciferase enzyme-mediated reaction.

The invention provides compositions or kits having one or more luciferin derivatives of the invention. The kits may optionally contain other reagents, e.g., enzyme, reaction mixtures, and the like. The bioluminogenic reaction mixtures, compositions and kits of the invention may optionally include an agent that slows the reaction rate, e.g., amino methyl benzothiazole (AMBT) or aminophenyl methyl benzothiazole (APMBT), see U.S. published application 2004/0171099, yielding glow kinetics and/or an agent that stabilizes light production, e.g., a thiol or coenzyme A.

BRIEF DESCRIPTION OF THE FIGURES

The following drawings are included to further demonstrate certain embodiments and/or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

DETAILED DESCRIPTION

I. Definitions

Figure 1:
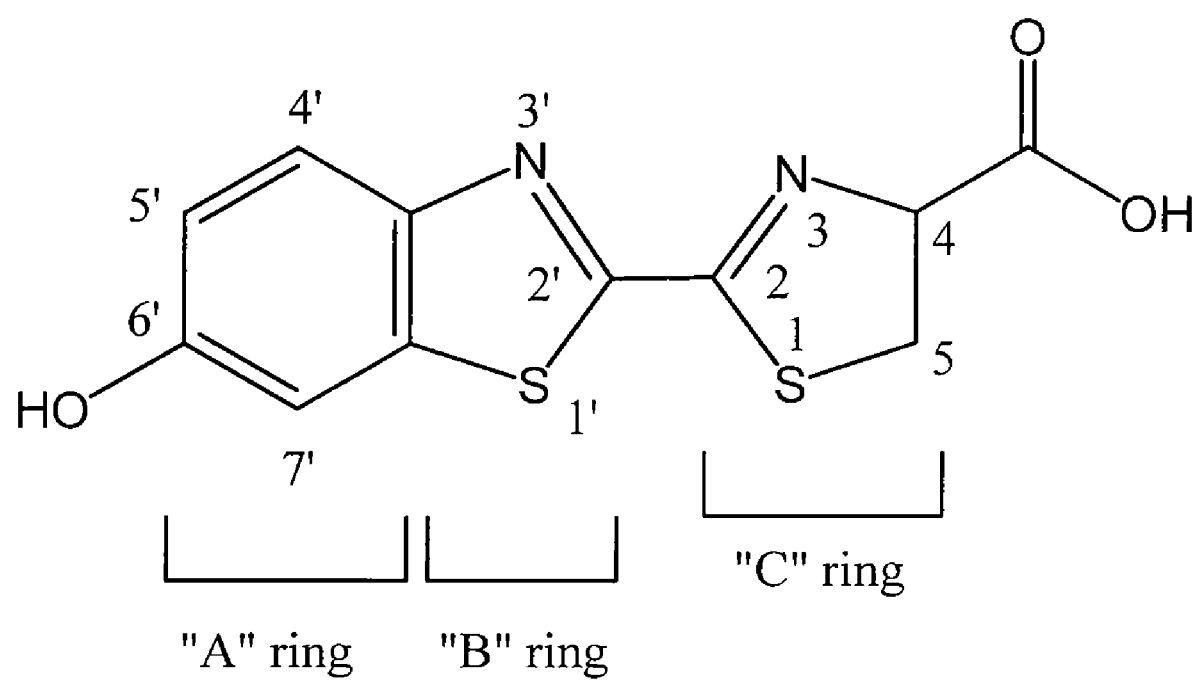
FIG. 1. Numbering of ring atoms in the six membered ring ("A ring" or "ring A"), five membered center ring ("B ring" or "ring B"), and thiazole five membered ring ("C ring" or "ring C") of beetle luciferin (D-luciferin).

As used herein, the following terms and expressions have the indicated meanings. It will be appreciated that the compounds of the present invention contain asymmetrically substituted carbon atoms and may be isolated in optically active or racemic forms. It is well known in the art how to prepare optically active forms, such as by resolution of racemic forms or by synthesis from optically active starting materials. All chiral, diastereomeric, racemic forms and all geometric isomeric forms of a structure are part of this invention.

Specific values listed below for radicals, substituents, and ranges are for illustration only; they do not exclude other defined values or other values within defined ranges for the radicals and substituents.

As used herein, the term "substituted" is intended to indicate that one or more (e.g., 1, 2, 3, 4, 5, or 6; in some embodiments 1, 2, or 3; and in other embodiments 1 or 2) hydrogens on the group indicated in the expression using "substituted" is replaced with a selection from the indicated group(s) or with a suitable group known to those of skill in the art, provided that the indicated atom's normal valency is not exceeded, and that the substitution results in a stable compound. Suitable substituents of a substituted group can include alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acetylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, hydroxyl (alkyl)amine, and cyano. Additionally, the suitable indicated groups can include, e.g., —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR—S(=O)$_2$O$^-$, —S(=O)$_2$OH, —S(=O)$_2$R, —OS(=O)$_2$OR, —S(=O)$_2$NR, —S(=O)R, —OP(=O)O$_2$RR, —P(=O) O$_2$RR, —P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, —C(NR) NRR, where each X is independently a halogen ("halo"): F, Cl, Br, or I; and each R is independently H, alkyl, aryl, heteroaryl, heterocycle, a protecting group or prodrug moiety. As would be readily understood by one skilled in the art, when a substituent is keto (=O) or thioxo (=S), or the like, then two hydrogen atoms on the substituted atom are replaced.

"Stable compound" and "stable structure" are meant to indicate a compound that is sufficiently robust to survive isolation to a useful degree of purity from a reaction mixture. Only stable compounds are contemplated by and claimed in the present invention however, certain unstable compounds, for example, those that cannot easily be isolated, can be employed in the methods described herein.

One diastereomer may display superior properties or activity compared with another. When required, separation of the racemic material can be achieved by HPLC using a chiral column or by a resolution using a resolving agent such as camphonic chloride as described by Tucker et al., *J. Med. Chem.*, 37:2437 (1994). A chiral compound may also be directly synthesized using a chiral catalyst or a chiral ligand, e.g., Huffman et al., *J. Org. Chem.*, 60:1590 (1995).

As used herein, the term "alkyl" refers to a branched, unbranched, or cyclic hydrocarbon having, for example, from 1 to 30 carbon atoms, and often 1 to 12, or 1 to about 6 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. For example, a substituted alkyl group can be a haloalkyl group, as described below. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylene). Additionally, the alkyl group can be optionally interrupted, as described below for the term 'interrupted'.

The term "alkenyl" refers to a monoradical branched or unbranched partially unsaturated hydrocarbon chain (i.e. a carbon-carbon, sp$^2$ double bond). In one embodiment, an alkenyl group can have from 2 to 10 carbon atoms, or 2 to 6 carbon atoms. In another embodiment, the alkenyl group has from 2 to 4 carbon atoms. Examples include, but are not limited to ethylene or vinyl, allyl, cyclopentenyl, 5-hexenyl, and the like. The alkenyl can be unsubstituted or substituted.

The term "alkynyl" refers to a monoradical branched or unbranched hydrocarbon chain, having a point of complete unsaturation (i.e. a carbon-carbon, sp triple bond). In one embodiment, the alkynyl group can have from 2 to 10 carbon atoms, or 2 to 6 carbon atoms. In another embodiment, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

The term "cycloalkyl" refers to cyclic alkyl groups of from 3 to 10 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted. The cycloalkyl group can be monovalent or divalent, and can be optionally substituted as described above for alkyl groups. The cycloalkyl group can optionally include one or more cites of unsaturation, for example, the cycloalkyl group can include one or more carbon-carbon double bonds, such as, for example, cyclohexene, 1,3-cyclohexadiene, 1,4-cyclohexadiene, and the like.

The term "alkoxy" refers to the group alkyl-O—, where alkyl is as defined herein. In one embodiment, alkoxy groups include, e.g., methoxy, ethoxy, n-propoxy, iso-propoxy, n-butoxy, tert-butoxy, sec-butoxy, n-pentoxy, n-hexyloxy, 1,2-dimethylbutoxy, and the like. The alkoxy can be unsubstituted or substituted.

As used herein, "aryl" refers to an aromatic hydrocarbon group derived from the removal of one hydrogen atom from a single carbon atom of a parent aromatic ring system. The radical can be at a saturated or unsaturated carbon atom of the parent ring system. The aryl group can have 6-30 carbon atoms, 6-20 carbon atoms, 6-14 carbon atoms, or 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups. For example, an aryl group can be substituted with one or more substituents (as described above) to provide various substituted aryls, such as pentafluorophenyl or para-trifluoromethylphenyl, and the like.

The term "halo" refers to fluoro, chloro, bromo, and iodo. Similarly, the term "halogen" refers to fluorine, chlorine, bromine, and iodine.

The term "haloalkyl" refers to alkyl as defined herein substituted by 1 or more halo groups as defined herein, which may be the same or different. In one embodiment, the haloalkyl can be substituted with 1, 2, 3, 4, or 5 halo groups. In another embodiment, the haloalkyl can by substituted with 1, 2, or 3 halo groups. The term haloalkyl also include perfluoro-alkyl groups. Representative haloalkyl groups include, by way of example, trifluoromethyl, 3-fluorododecyl, 12,12,12-trifluorododecyl, 2-bromooctyl, 3-bromo-6-chloroheptyl, 1H,1H-perfluorooctyl, and the like. The haloalkyl can be optionally substituted as described above for alkyl groups.

The term "heteroaryl" is defined herein as a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described above in the definition of "substituted". Typical heteroaryl groups contain 2-20 carbon atoms in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, □-carbolinyl, carbazolyl, chromenyl, cinnolinyl, dibenzo[b,d]furanyl, furazanyl, furyl, imidazolyl, imidazolyl, indazolyl, indolisinyl, indolyl, isobenzofuranyl, isoindolyl, isoquinolyl, isothiazolyl, isoxazolyl, naphthyridinyl, oxazolyl, pyrimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In another embodiment heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, and sulfur, and optionally substituted with one or more groups as defined herein under the term "substituted". A heterocycle can be a monocyclic, bicyclic, or tricyclic group containing one or more heteroatoms. A heterocycle group also can contain an oxo group (═O) or a thioxo (═S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The term "heterocycle" can include, by way of example and not limitation, a monoradical of the heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* 1960, 82, 5566. In one embodiment, "heterocycle" includes a "carbocycle" as defined herein, wherein one or more (e.g. 1, 2, 3, or 4) carbon atoms have been replaced with a heteroatom (e.g. O, N, or S).

Examples of heterocycles, by way of example and not limitation, include, dihydropyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one embodiment, nitrogen bonded heterocycles include 1-aziridyl, 1-azetedyl, 1-pyrrolyl, 1-imidazolyl, 1-pyrazolyl, and 1-piperidinyl.

The term "carbocycle" refers to a saturated, unsaturated or aromatic ring having 3 to 8 carbon atoms as a monocycle, 7 to 12 carbon atoms as a bicycle, and up to about 30 carbon atoms as a polycycle. Monocyclic carbocycles typically have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. The carbocycle can be optionally substituted as described above for alkyl groups.

The term "alkanoyl" or "alkylcarbonyl" refers to —C(═O)R, wherein R is an alkyl group as previously defined.

The term "acyloxy" or "alkylcarboxy" refers to —O—C(═O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to —C(=O)OR (or "COOR"), wherein R is an alkyl group as previously defined.

The term "amino" refers to —$NH_2$. The amino group can be optionally substituted as defined herein for the term "substituted". The term "alkylamino" refers to —$NR_2$, wherein at least one R is alkyl and the second R is alkyl or hydrogen. The term "acylamino" refers to —N(R)C(=O)R, wherein each R is independently hydrogen, alkyl, or aryl.

The term "amino acid," includes a residue of a natural amino acid (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an α-methylbenzyl amide). Other suitable amino and carboxy protecting groups are known to those skilled in the art (See for example, Greene, T. W.; Wutz, P. G. M. *Protecting Groups In Organic Synthesis,* $2^{nd}$ edition, John Wiley & Sons, Inc., New York (1991) and references cited therein).

The term "peptide" describes a sequence of 2 to 35 amino acids (e.g. as defined hereinabove) or peptidyl residues. The sequence may be linear or cyclic. For example, a cyclic peptide can be prepared or may result from the formation of disulfide bridges between two cysteine residues in a sequence. Preferably a peptide comprises 3 to 20, or 5 to 15 amino acids. Peptide derivatives can be prepared as disclosed in U.S. Pat. Nos. 4,612,302; 4,853,371; and 4,684,620, or as described in the Examples herein below. Peptide sequences specifically recited herein are written with the amino terminus on the left and the carboxy terminus on the right.

The term "saccharide" refers to a sugar or other carbohydrate, especially a simple sugar. The saccharide can be a $C_6$-polyhydroxy compound, typically $C_6$-pentahydroxy and often a cyclic glycal. The term includes the known simple sugars and their derivatives as well as polysaccharides with two or more monosaccharide residues. The saccharide can include protecting groups on the hydroxyl groups as described above in the definition of amino acids. The hydroxyl groups of the saccharide can be replaced with one or more halo or amino groups. Additionally, one or more of the carbon atoms can be oxidized, for example to keto or carboxyl groups.

The term "interrupted" indicates that another group is inserted between two adjacent carbon atoms (and the hydrogen atoms to which they are attached (e.g., methyl ($CH_3$), methylene ($CH_2$) or methine (CH))) of a particular carbon chain being referred to in the expression using the term "interrupted", provided that each of the indicated atoms' normal valency is not exceeded and the interruption results in a stable compound. Suitable groups that can interrupt a carbon chain include, e.g., with one or more non-peroxide oxy (—O—), thio (—S—), imino (—N(H)—), methylene dioxy (—$OCH_2O$—), carbonyl (—C(=O)—), carboxy (—C(=O)O—), carbonyldioxy (—OC(=O)O—), carboxylato (—OC(=O)—), imine (C=NH), sulfinyl (SO) and sulfonyl ($SO_2$).

Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached.

As to any of the above groups, which contain one or more substituents, it is understood, of course, that such groups do not contain any substitution or substitution patterns that are sterically impractical and/or synthetically non-feasible. In addition, the compounds of this invention include all stereochemical isomers arising from the substitution of these compounds.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in an claim of the invention, the total number will be determined as set forth above.

The term "linker" as used herein is a carbon chain that covalently attaches two chemical groups together and optionally can self-cleave or if covalently bonded to a substrate for an enzyme, may be cleaved by that enzyme or another molecule. The carbon chain of the linker can be optionally interrupted by one or more nitrogen atoms, oxygen atoms, carbonyl groups, (optionally substituted)aromatic rings, or peptide bonds.

The term "luciferase," unless specified otherwise, refers to a naturally occurring or mutant luciferase. The luciferase, if naturally occurring, may be obtained easily by the skilled from an organism. If the luciferase is one that occurs naturally or is a mutant that retains activity in the luciferase-luciferin reaction of a naturally occurring luciferase, it can be obtained readily from a culture of bacteria, yeast, mammalian cells, insect cells, plant cells, or the like, transformed to express a cDNA encoding the luciferase or from an in vitro cell-free system for making the luciferase from a nucleic acid encoding same. Luciferases are available from Promega Corporation, Madison, Wis.

As used herein, a "bioluminogenic assay" or "bioluminogenic reaction" includes a reaction in which a product of a reaction between a nonluciferase enzyme and a derivative of luciferin or aminoluciferin is a substrate for luciferase or a product of a nonenzymatic reaction having a derivative of luciferin or aminoluciferin is a substrate for luciferase, or a reaction between a luciferase and a derivative of luciferin or aminoluciferin is bioluminogenic, i.e., produces a measurable amount of light.

As used herein, "bioluminescence" is light produced as a result of a reaction between an enzyme and a substrate that generates light. Examples of such enzymes (bioluminescent enzymes) include firefly luciferase, click beetle luciferase, *Renilla* luciferase, cypridina luciferase, Aequorin photoprotein, obelin photoprotein and the like.

As used herein, a "bioluminogenic assay reagent" may include a substrate as well as a cofactor(s) or other molecule(s) such as a protein, e.g., an enzyme, for a bioluminogenic reaction.

A "reaction mixture" may contain all reagents for a particular reaction or may lack at least one of the reagents for the reaction. For example, a luciferase reaction mixture may contain reagents for the reaction except for a substrate for the luciferase, e.g., a reaction mixture useful to determine whether a test sample has a luciferase substrate. A reaction mixture for a nonluciferase enzyme may include all reagents for that reaction except for a molecule to be detected, e.g., the mixture contains all reagents except for a cofactor for the nonluciferase enzyme; therefore the mixture can be useful to detect the presence of the cofactor in a test sample.

As used herein, a "derivative of luciferin" or a "derivative of aminoluciferin" is a molecule that is a substrate for a nonluciferase enzyme and a prosubstrate of a luciferase, a substrate for a luciferase, a substrate for a nonluciferase enzyme and a substrate for a luciferase or is useful to detect molecules generated in nonenzymatic reactions. The derivatives of the invention have one or more modifications to one or more of the three rings and/or substituents attached to one or more of the rings of the D-luciferin or aminoluciferin backbone (see FIG. 1). An acetal derivative of luciferin or aminoluciferin refers to luciferin or aminoluciferin wherein the C4 carboxy moiety is modified to form an acetal moiety. Such derivatives may also include modifications to one or more of the rings, modifications to the C6' hydroxyl or amino group, substitutions on the C6' hydroxyl or amino group, and/or substitutions at one or more of the 5, 4', 5', or 7' positions. When the B ring is modified to form a six-membered ring, any position on the resulting A ring or B ring may include a substitutent, to provide an acetal derivative of the invention. All such derivatives than include an acetal moiety at C4 of the C ring are considered acetal derivative of luciferin or aminoluciferin.

An enzyme that is "native" to cells or tissue refers to an enzyme that is naturally occurring in the cells or tissue.

II. Methods of the Invention

The invention provides a bioluminogenic method which employs an acetal derivative of luciferin or aminoluciferin to detect one or more molecules, e.g., an enzyme, a cofactor for an enzymatic reaction, an enzyme substrate, an enzyme inhibitor, or an enzyme activator. The invention thus provides for bioluminogenic assays to detect the amount, activity or presence of a molecule in a sample.

The methods may be used, for example, to determine the presence or amount of at least one molecule, e.g., a nonluciferase enzyme, a regulator of a nonluciferase enzyme, a nonluciferase enzyme substrate, and/or cofactors of the reaction, or a condition in a sample including but not limited to an animal, e.g., vertebrate, physiological fluid, e.g., blood, plasma, urine, mucous secretions and the like, a cell, cell lysate, cell supernatant, or purified fraction of a cell (e.g., a subcellular fraction). In one embodiment, the methods according to the present invention provide a rapid method for detecting one or more molecules in a single sample such as an aliquot of cells or a lysate thereof. In one embodiment, the method includes quantifying the presence, amount or specific activity of a molecule such as an enzyme, substrate or cofactor in a bioluminogenic assay. The intensity of the bioluminogenic signal is a function of the presence or amount of the respective molecule. In addition, the reaction may contain one or more test agents, e.g., enzyme inhibitors or activators, and/or different concentrations of inhibitors or activators. In one embodiment, the method employs at least two different reactions where the first reaction is a nonluciferase enzyme-mediated reaction and the second reaction is a beetle luciferase-mediated reaction.

Thus, a bioluminogenic assay may directly or indirectly detect, e.g., measure the amount, presence or specific activity of, for example, a cofactor for an enzyme-mediated reaction, an enzyme, an enzyme substrate, an inhibitor of the enzyme, or an activator of the enzyme. For instance, in one embodiment, an acetal derivative of luciferin that is a substrate for a nonluciferase enzyme, for instance, a derivative that is a substrate of a CYP3A, yields a product that is a substrate for a beetle luciferase and may be employed in a bioluminogenic assay to detect the CYP3A. In one embodiment, the derivative is a prosubstrate of a beetle luciferase that yields a product that is a substrate of luciferase but does not itself yield a substantial amount of light in a reaction with the beetle luciferase.

In one embodiment, the invention provides a bioluminescent assay method to detect one or more nonluciferase enzymes. The method includes contacting a sample suspected of having one or more nonluciferase enzymes and a substrate or a co-factor for the nonluciferase-mediated reaction with a corresponding reaction mixture that includes a derivative of luciferin or a derivative of aminoluciferin that is a substrate for the nonluciferase enzyme. In one embodiment, the derivative is one having a modification in the C ring of D-luciferin that includes a recognition site for the nonluciferase enzyme, e.g., for CYP3A, and also optionally includes a modification in the B ring of D-luciferin, which derivative is a prosubstrate for luciferase. Thus, the derivative may have a modification in one of the rings that includes a recognition site for the enzyme of interest as well as a further modification in that ring or one or more of the other rings that may or may not have a recognition site for another enzyme or molecule of interest.

If the derivative is a prosubstrate for luciferase, i.e., the product of a reaction between the derivative and the nonluciferase enzyme is a substrate for luciferase, sequential or concurrent reactions for the nonluciferase enzyme and the luciferase may be conducted. For instance, a reaction for a nonluciferase enzyme that contains the prosubstrate may be conducted in a single well, and a beetle luciferase reaction mixture can be added to that well. In another embodiment, a reaction mixture for a nonluciferase enzyme that contains the prosubstrate is conducted in a single well and a portion of that reaction added to a different well having a beetle luciferase reaction mixture. Alternatively, reactions may be conducted simultaneously in the same well.

The invention thus provides a method to detect or determine the presence or amount of a molecule for a nonluciferase enzyme-mediated reaction in a sample. The method includes contacting a sample, a first reaction mixture for a nonluciferase enzyme-mediated reaction, and a derivative of luciferin that is a substrate for the nonluciferase enzyme to yield a first mixture or providing such a first mixture comprising a luminogenic product that is a substrate for a luciferase or providing such a first mixture. In one embodiment, the derivative is a compound of formula I. At least a portion of the first mixture is contacted with a second reaction mixture for a beetle luciferase-mediated reaction to yield a second mixture. Then, luminescence in the second mixture is detected or determined, thereby detecting or determining the presence or amount of a molecule for the nonluciferase enzyme-mediated reaction in the sample. In some embodiments, the sample, the nonluciferase reaction mixture or luciferase reaction mixture may include an esterase, e.g., if the product of the reaction between the derivative and the nonluciferase enzyme has an ester group and that product is a proluciferase substrate. The esterase may be included with the first reaction mixture, added prior to initiation of the luciferase reaction mixture, or included in the luciferase reaction mixture.

Further provided is a method to detect or determine the presence or amount of a molecule for a nonluciferase enzyme-mediated reaction in a sample. The method includes contacting a sample, a reaction mixture for a nonluciferase-mediated enzyme reaction and for a luciferase-mediated reaction, and a derivative of luciferin that is a substrate for the nonluciferase enzyme to yield a mixture. A reaction between the nonluciferase enzyme and the derivative yields a luminogenic product that is a substrate for the luciferase. In one embodiment, the derivative is a compound of formula I. Luminescence in the mixture is detected or determined, thereby detecting or determining the presence or amount of a molecule for the nonluciferase-mediated reaction in the sample.

For the bioluminogenic assays described herein which employ luciferin derivatives with a lower background, those assays can use lower (or higher) amounts of the derivative, and those derivatives may have improved reactivity, e.g., with a nonluciferase enzyme. In addition, for any of the bioluminogenic assays described herein, other reagents may be added to reaction mixtures, including but not limited to those that inhibit or prevent inactivation of luciferase or otherwise extend or enhance luminescent signal.

Also provided is a method to identify or measure the potency of a modulator of a nonluciferase enzyme-mediated reaction. The method includes contacting one or more agents, a first reaction mixture for a nonluciferase enzyme-mediated reaction, and a derivative of luciferin that is a substrate for the nonluciferase enzyme, so as to yield a first mixture, or providing such a mixture. The first mixture in the absence of the one or more agents includes a luminogenic product that is a substrate for a beetle luciferase. At least a portion of the first mixture and a second reaction mixture for a beetle luciferase-mediated reaction are mixed to yield a second mixture. Luminescence in the second mixture is compared with a control mixture, thereby identifying whether one or more of the agents modulates the nonluciferase enzyme-mediated reaction and/or to what extent and potency.

In one embodiment of the invention, test compounds can be screened and evaluated for their activities as substrates or cofactors of, or regulators, either inhibitors or activators, of an enzymatic reaction by using the luciferin derivatives of the present invention. A candidate compound may be determined to be a regulator or a substrate of a reaction by contacting a reaction mixture with a derivative and the test compound under conditions that would, in the absence of the test compound, yield bioluminescence or a bioluminogenic product.

In one aspect of the invention, a method is provided to distinguish between a substrate and an inhibitor of a reaction. For example, the compound is incubated with at least one enzyme under conditions which allow for metabolism of the compound prior to providing a luciferin derivative under conditions that, in the absence of an inhibitor or substrate of the enzyme, would be suitable for interaction between the luciferin derivative and the enzyme. In one embodiment, the product of that reaction is a substrate of luciferase and in the presence of luciferase yields a light emitting second reaction. The resulting light emitting reaction is compared to the one obtained from contacting the enzyme with the compound and the derivative under conditions that would, in the absence of an inhibitor of the enzyme, be suitable for interaction between the luciferin derivative and the enzyme. Metabolism of the compound by the enzyme reduces its concentration in the assay medium and may lead to an apparent loss of inhibitory activity compared to conditions without metabolism of the compound which would indicate it was a substrate for the enzyme. An inhibitory compound that was not metabolized would show equal potency, irrespective of the time of addition of the substrate.

In one aspect of the invention, the compound is preferably contacted first with the enzyme for a first predetermined time period. Thereafter, the mixture is contacted with a luciferin derivative and bioluminescent enzyme, e.g., luciferase, simultaneously or contemporaneously, and the mixture is allowed to incubate for a second predetermined time period.

In another aspect of the invention, the compound is incubated with the enzyme for a first predetermined time period to form a first mixture. Thereafter, the first mixture is contacted with the luciferin derivative to form a second mixture that is allowed to incubate for a second predetermined time period. The second mixture is then contacted with a bioluminescent enzyme, e.g., luciferase, to form a third mixture that is allowed to incubate for a third predetermined time period. Thereafter, the activity resulting from the interaction of the enzyme with the compound is determined by measuring luminescence during and/or after the third predetermined time period relative to a control (e.g., no compound) reaction. In this way, for example, mechanism based inhibitors of the first enzyme can be identified and distinguished from non-mechanism based inhibitors because the first incubation with the test compound but without the luciferin derivative will lead to a more profound inhibition by a mechanism based inhibitor than would be observed without the first incubation or substrates of the first reaction will show reduced inhibition.

In another embodiment of the invention, a cell-based method is provided for screening a compound to determine its effect on enzyme activity of the cell. The test compound is contacted with a cell having the enzyme, either naturally or via recombinant expression, the luciferin derivative, and bioluminescent enzyme, e.g., luciferase, or contacted with a cell having the enzyme and luciferase, and the derivative for a predetermined period of time. Thus, in one embodiment, a cell that either transiently or stably expresses a recombinant enzyme such as a bioluminescent enzyme, e.g., luciferase, may be employed. Any conventional method for creating transient or stable transfected cells may be used. In one embodiment, a luciferin derivative is contacted with and enters a cell and, if the appropriate molecule is present, yields a product that is a substrate for luciferase. If a luciferase is present in the cell, luminescence can be detected. Alternatively, in a cell which lacks luciferase, the product passes out of the cell into the medium and the medium is added to a luciferase reaction mixture. Thereafter, the activity resulting from the interaction of the cell with the compound is determined by measuring luminescence of the reaction mixture relative to a control (minus test compound) reaction mixture.

In one aspect of the invention, the compound is preferably contacted first with the cell for a time period. Thereafter, the cell is contacted with the luciferin derivative and luciferase simultaneously or contemporaneously, and the mixture allowed to incubate for a second time period. Enzyme activity is determined by measuring the amount of luminescence generated from the reaction mixture relative to a control reaction mixture (e.g., minus test compound). In another aspect of the invention, the test compound is preferably contacted first with the cell for a time period. Thereafter, the exposed cell is then contacted with the luciferin derivative and incubated for a second time period. The cell is then contacted with luciferase to form a third mixture which is allowed to incubate for a third time period. Thereafter, the activity of the cell resulting from the interaction of the cell with the test compound(s) is determined by measuring luminescence of the reaction mixture relative to a control reaction mixture (e.g., minus test compound).

A cell-based luminescence detection assay for molecules present in the cell medium, e.g., molecules which actively or via inactive mechanisms are present in the cell medium, can include adding a reaction mixture with the luciferin derivative to the cell medium or adding the cell medium to a reaction mixture with the luciferin derivative and detecting luminescence.

In yet another embodiment of the cell-based assay of the invention, the cells may be lysed in an appropriate lysis buffer. For example, detergent addition can rupture the cells and release cell content. For animal cells, a buffer with 0.1-1.0% non-ionic detergents such as Triton X 100 or Tergitol is typically sufficient. Bacteria, plant, fungal or yeast cells are usually more difficult to lyse. Detergents, freeze/thaw cycles, hypotonic buffers, sonication, cavitation or combinations of these methods may be used. The method of lysis that produces a lysate is compatible with luciferase or other enzyme activity or the detection of other molecules or conditions.

The presence or activity of nonluciferase enzymes may be measured in cells grown in culture medium or in cells within animals, e.g., living animals. For measurements in cells in animals, a luciferin derivative may be administered to the animal, e.g., injected into the animal or added to an aqueous solution, e.g., water, or food consumed by the animal. Conversion of the derivative to a product that is a luciferase substrate may be detected by luminescence mediated by luciferase expressed in cells in the animal, e.g., transgenic cells, by luciferase administered to the animal, e.g., injected into the animal, or by collecting physiological fluids, e.g., blood, plasma, urine, and the like, or tissue samples, and combining those with a luciferase reagent.

Assays which employ two reactions may be conducted simultaneously (one step) or sequentially (two step) to detect one or more moieties including proteins (peptides or polypeptides), e.g., enzymes, substrates, cofactors, inhibitors or activators for enzymatic reactions, or conditions, e.g., redox conditions. A sequential reaction may be conducted in the same vessel, e.g., a well of a multiwell plate. For a two step assay, the first reaction mixture may contain all of the reagents or less than all of the reagents for a nonluciferase enzyme-mediated reaction where one of the reagents that is absent is the one to be detected in a sample, e.g., a cell lysate. For instance, a nonluciferase enzyme-mediated reaction is performed under conditions effective to convert a luciferin derivative that is a substrate for the nonluciferase and a pro-substrate of luciferase to a product that is a substrate of luciferase. The first reaction may be quenched at the time or prior to addition of a luciferase reaction mixture. For instance, a quencher of the first reaction may be present in the luciferase reaction mixture. The luciferase reaction mixture preferably substantially lacks a substrate for the luciferase, e.g., the only source of substrate for the luciferase is provided by a reaction between the nonluciferase enzyme and the derivative. When all the reagents for the first reaction are present in the first reaction mixture, the assay may be employed to identify moieties that alter the reaction, e.g., inhibitors or enhancers of the reaction. After performing the reactions, either simultaneously or sequentially, the presence or amount of one or more molecules or one or more inhibitors or activators of the reaction(s) is/are detected or determined and/or to what extent and/or potency.

For a one step assay, a reaction mixture may contain reagents for two reactions, such as reagents for a nonluciferase enzyme-mediated reaction and a luciferase-mediated reaction or for a nonenzymatic reaction and a luciferase-mediated reaction.

For assays which employ two reactions, the order of adding the molecules for the assays can vary. If initiated and conducted sequentially (whether in the same vessel or not), adjustments to reaction conditions, e.g., reagent concentration, temperatures or additional reagents, may be performed. For instance, a quenching agent or enhancing agent may be added between reactions (see, e.g., U.S. Pat. Nos. 5,744,320 (Sherf et al.) and 6,586,196 (Bronstein et al.), the disclosures of which are specifically incorporated by reference herein). In one embodiment, the two or more reactions are carried out simultaneously in a single reaction mixture. Optionally, the assays are a homogeneous assay, e.g., the components are mixed prior to adding the mixture to the sample. Results may be read without additional transfer of reagents.

The assays of the present invention thus allow the detection of one or more molecules or conditions in a sample, e.g., a sample which includes eukaryotic cells, e.g., yeast, avian, plant, insect or mammalian cells, including but not limited to human, simian, murine, canine, bovine, equine, feline, ovine, caprine or swine cells, prokaryotic cells, cells from two or more different organisms, cell lysates or supernatants thereof, or a sample that includes a purified form of the molecule, e.g., a purified nonluciferase enzyme that is useful to prepare a standard curve. The cells may not have been genetically modified via recombinant techniques (nonrecombinant cells) or may be recombinant cells that are transiently transfected with recombinant DNA and/or the genome of which is stably augmented with a recombinant DNA or which genome has been modified to disrupt a gene, e.g., disrupt a promoter, intron or open reading frame, or replace one DNA fragment with another. The recombinant DNA or replacement DNA fragment may encode a molecule to be detected by the methods of the invention, a moiety which alters the level or activity of the molecule to be detected, and/or a gene product unrelated to the molecule or moiety that alters the level or activity of the molecule.

The derivatives of the invention include compounds that can be employed to detect other reactions. For instance, molecules or conditions to be detected by the method include but are not limited to enzymes, e.g., demethylases, oxidases (e.g., a MAO), deacetylases, deformylases, proteases (proteosome, calpain, beta-secretase, cathepsin, calpain, thrombin, granzyme B), phosphatases, kinases, peroxidases, transferases, e.g., GST, sulfotases, beta-lactamases, cytochrome P450 enzymes, esterase, e.g., acetylcholinesterase, dehydrogenase, luciferase, substrates, inhibitors, co-factors, activators of enzyme mediated reactions, reactive oxygen species, reducing conditions and transcriptional regulators or regulators of gene transcription.

The enzymes employed in the methods, either enzymes to be detected or enzymes that are useful to detect a substrate or cofactor, can be selected from any combination of enzymes including recombinant and endogenous (native) enzymes. In one embodiment, the enzyme to be detected is an endogenous enzyme. In another embodiment, the enzyme is a recombinant enzyme. Other combinations apparent to one of ordinary skill in the art can be used in the present assays and methods according to the teachings herein. The enzymes include but are not limited to proteases, phosphatases, peroxidases, sulfatases, peptidases, oxidases, dealkylases, deformylases and glycosidases. The enzyme may be a hydrolase, oxidoreductase, lyase, transferase, e.g., glutathione S transferase, isomerase, ligase, synthase, alkaline or acid phosphatase, decarboxylase, phospholipase D, P-xylosidase, β-D-fucosidase, thioglucosidase, β-D-galactosidase, α-D-galactosidase, α-D-glucosidase, β-D-glucosidase, β-D-glucuronidase, α-D-mannosidase, β-D-mannosidase, β-D-fructofuranosidase, or β-D-glucosiduronase. Of particular interest are classes of enzymes that have physiological significance. These enzymes include protein peptidases, esterases, protein phosphatases, glycosylases, proteases, dehydrogenases, oxidases, oxygenases, reductases, methylases, lipases, phospholipases, sulphatases, ureases, including acid phosphatases, glucosidases, glucuronidases, galactosidases, and carboxylesterases, and the like. Enzymes of interest include those involved in making or hydrolyzing esters, both organic and inorganic, glycosylating, and hydrolyzing amides. In any class, there may be further subdivisions.

III. Luciferin Derivatives

Bioluminescent substrates according to the present invention include acetal derivatives of luciferin or aminoluciferin. Such compound include compounds having the general formulas described below.

In one embodiment, the invention provides a compound of formula I:

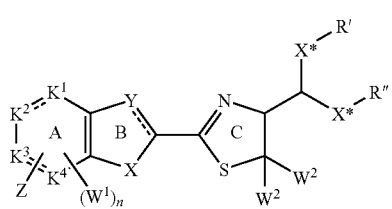

wherein
Y is N, N-oxide, N—($C_1$-$C_6$)alkyl, or CH;
X is S, O, CH=CH, N=CH, or CH=N;
each X* is independently O or S;
R' and R" are independently ($C_1$-$C_{20}$)alkyl, ($C_2$-$C_{20}$)alkenyl, ($C_2$-$C_{20}$)alkynyl, ($C_3$-$C_{20}$)cycloalkyl, ($C_6$-$C_{30}$)aryl, heteroaryl, heterocycle, and may be optionally substituted with hydroxyl, ($C_1$-$C_{12}$)alkoxy, oxy, amino, halo, carboxyl, thio, ($C_6$-$C_{30}$)aryl, heteroaryl, or heterocycle, or R' and R" together form a cyclic species;
Z is H, OR, OH, $NH_2$, NHR, or NRR;
$W^1$ is H, halo, ($C_1$-$C_6$)alkyl, ($C_2$-$C_{20}$)alkenyl, hydroxyl, or ($C_1$-$C_6$)alkoxy; and n is 1, 2, or 3; or
a $W^1$ and Z together form a keto group on ring A, and at least one of the dotted lines denoting optional bonds in ring A is absent;
each $W^2$ is independently H, halo, ($C_1$-$C_6$)alkyl, ($C_2$-$C_4$)alkenyl, hydroxyl, or ($C_1$-$C_6$)alkoxy;
each of $K^1$, $K^2$, $K^3$, and $K^4$ is independently CH, N,N-oxide, or N—($C_1$-$C_6$)alkyl, and the dotted lines between $K^1$ and $K^2$, and $K^3$ and $K^4$, denote optional bonds; and when the carbon of any CH is substituted, the H is absent;
the dotted line in ring B is an optional double bond;
each R is independently H, ($C_1$-$C_{20}$)alkyl, ($C_2$-$C_{20}$)alkenyl, ($C_2$-$C_{20}$)alkynyl, ($C_3$-$C_{20}$)cycloalkyl, ($C_1$-$C_{12}$)alkoxy, ($C_6$-$C_{30}$)aryl, aryl($C_1$-$C_{20}$)alkyl, heteroaryl, heterocycle, ($C_1$-$C_{20}$)alkylsulfonyl, ($C_6$-$C_{30}$)arylsulfonyl, heteroarylsulfonyl, ($C_1$-$C_{20}$)alkylsulfinyl, ($C_6$-$C_{30}$)arylsulfinyl, heteroarylsulfinyl, ($C_1$-$C_{20}$)alkoxycarbonyl, amino, NH($C_1$-$C_6$)alkyl, N(($C_1$-$C_6$)alkyl)$_2$, tri($C_1$-$C_{20}$)ammonium($C_1$-$C_{20}$)alkyl, heteroaryl($C_1$-$C_{20}$)alkyl, heteroaryl having quaternary nitrogen, heteroarylcarbonyl having quaternary nitrogen, ($C_6$-$C_{30}$)arylthio, ($C_1$-$C_{20}$)alkylphosphate, ($C_1$-$C_{20}$)alkylphosphonate, ($C_6$-$C_{30}$)arylphosphate, ($C_6$-$C_{30}$)arylphosphonate, phosphate, sulfate, or saccharide;

or when Z is NRR, RR together with the N to which they are attached optionally form a heteroaryl or heterocycle group;

wherein any alkyl, alkenyl, alkynyl, cycloalkyl, alkoxy, amino, aryl, heteroaryl, or heterocycle group is optionally substituted with 1, 2, 3, 4, or 5 substituents selected from ($C_1$-$C_{20}$)alkyl, ($C_2$-$C_{20}$)alkenyl, ($C_2$-$C_{20}$)alkynyl, ($C_3$-$C_{20}$)cycloalkyl, ($C_1$-$C_{20}$)alkoxyl, ($C_1$-$C_{20}$)alkylcarbonyl, ($C_1$-$C_{20}$)alkylcarboxyl, halo, hydroxyl, —COOR$^x$, —S(O)R$^x$, —SO$_2$R$^x$, —SO$_3$R$^x$, nitro, amino, phosphate, ($C_1$-$C_{20}$)alkylphosphate, ($C_1$-$C_{20}$)alkylphosphonate, NH($C_1$-$C_6$)alkyl, NH($C_1$-$C_6$)alkynyl, N(($C_1$-$C_6$)alkyl)$_2$, N(($C_1$-$C_6$)alkynyl)$_2$, mercapto, ($C_1$-$C_{20}$)alkylthio, ($C_6$-$C_{14}$)aryl, ($C_6$-$C_{14}$)arylthio, trifluoromethyl, =O, heteroaryl, or heterocycle, and each substituent is optionally substituted with one to three R groups; wherein R$^x$ is H, ($C_1$-$C_6$)alkyl, ($C_6$-$C_{14}$)aryl, heterocycle, or heteroaryl;

or a salt thereof;

when Z comprises a nitrogen moiety, one or both of the hydrogens of the Z nitrogen moiety may be replaced by ($C_1$-$C_{20}$)alkyl or the group L, wherein L is an amino acid radical, a peptide radical having up to 20 amino acid moieties, or any other small molecule that is a substrate for a nonluciferase;

when Z is a hydroxyl group or a nitrogen moiety, H of the hydroxyl or nitrogen moiety may be replaced by (HO)$_2$P(O)—OCH$_2$—, sulfo, —PO$_3$H$_2$, or by a cephalosporanic acid attached to the group Z via a carbon chain of one to about 12 carbon atoms;

when Z is a hydroxyl group or a nitrogen moiety, one H of the hydroxyl or nitrogen moiety may be replaced by the group L'-linker, wherein L' is a group removable by an enzyme to free the linker, and linker is a carbon chain that can self-cleave, optionally interrupted by one or more nitrogen atoms, oxygen atoms, carbonyl groups, optionally substituted aromatic rings, or peptide bonds;

linker is attached to L' via an oxygen atom or an NH group at one terminus of the linker and the other terminus of the linker forms an ether, ester, or amide linkage with a group Z; and when Z is OR. formula I is optionally a dimer connected at the two A rings via a linker comprising a ($C_1$-$C_{12}$)alkyl diradical that is optionally interrupted by one to four O atoms, N atoms, or an optionally substituted aryl, heteroaryl, or heterocycle group to form a bridge between the dimer of formula I, and the R group of each Z group connecting the dimer of formula I is replaced by the bridge. When a quaternary nitrogen or other cationic species is present in formula I, an anion such as $A^-$ can be present. The anion $A^-$ can be any suitable counter ion, such as a halogen, a nitrate, a sulfate, a phosphate, or an organic anion such as a carbonate.

In some embodiments, the compounds and methods of the invention can include luminescent substrates such as luciferin or aminoluciferin. In other embodiments, formula I excludes luciferin or aminoluciferin, and/or can exclude any one or more substituents, for example, one or more specific substituents recited for the definition of the group R.

As illustrated by formula I, the core structure of rings A and B can be a number of different ring systems. Modification of ring B allows the core structure to include benzofuran, benzothiophene, benzoxazole, naphthalene, quinoline, isoquinoline, quinazoline, and quinoxyline ring systems, including the corresponding N-oxide and N-alkyl derivatives. Ring B modification also allows for access to N-oxide and N-alkyl derivatives of benzo[d]thiazole. Furthermore, by substituting a carbon atom of ring A in formula I with N,N-oxide, or N-alkyl (e.g., substituting one value of $K^1$, $K^2$, $K^3$, or $K^4$ for another value), other ring systems can be obtained, such as 1,8-naphthyridine, 1,7-naphthyridine, 1,6-naphthyridine, and 1,5-naphthyridine ring systems; pyrido[3,2-b]pyrazine, pyrido[4,3-b]pyrazine, pyrido[3,4-b]pyrazine, and pyrido[2,3-b]pyrazine ring systems; pyrido[2,3-d]pyrimidine, pyrido[3,4-d]pyrimidine, pyrido[4,3-d]pyrimidine, and pyrido[3,2-d]pyrimidine ring systems; benzo[d]oxazole, oxazolo[4,5-b]pyridine, oxazolo[4,5-c]pyridine, oxazolo[5,4-c]pyridine, and oxazolo[5,4-b]pyridine ring systems; and thiazolo[4,5-b]pyridine, thiazolo[4,5-c]pyridine, thiazolo[5,4-c]pyridine, and thiazolo[5,4-b]pyridine ring systems.

Formula I also illustrates that by substituting a second carbon atom of ring A with N,N-oxide, or N-alkyl, the corresponding pyrazine, pyrimidine, and pyridazine ring A analogs can be obtained for each of the above described ring systems. The substitution of a third carbon atom in ring A of formula I with N,N-oxide, or N-alkyl provides access to the corresponding 1,2,4-triazine ring system derivatives.

Formula I further includes the various dihydro, tetrahydro, and hexahydro derivatives of each of its ring systems.

Formula I also includes various acetal, thioacetal, and mixed acetal species. Accordingly, in some embodiments, each X* is O. The variables X* can also both be S. In some embodiments, on X* is O and the other is S.

Additional examples of the compounds of formula I include the compounds of formulas II-IV. In one embodiment, the compounds of the invention include compounds of formula II:

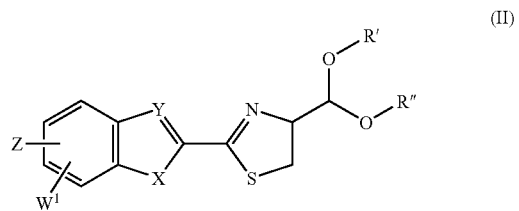

wherein Y is N or CH; X is S or —CH═CH—; $W^1$ is H or halo and up to four $W^1$ substituents may be present, and Z, R' and R" are as defined for formula I. In some embodiments, $W^1$ is F and 1, 2, 3, or 4 F groups may be present on the A ring.

The compounds of the invention also include compounds of formula III:

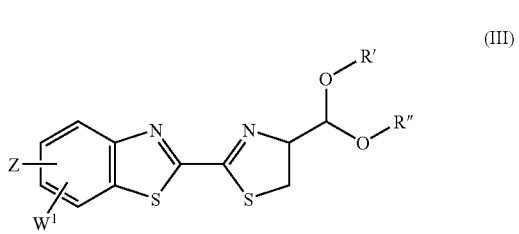

wherein $W^1$ is H or halo and up to four $W^1$ substituents may be present, and Z, R' and R" are as defined for formula I.

The compounds of the invention also include compounds of formula IV:

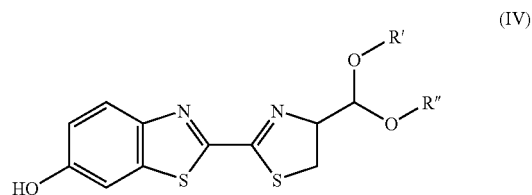

wherein R' and R" are as defined for formula I. Examples of R' and R", or R' and R" taken together, for each of formulas I-IV include optionally substituted $(C_1-C_{20})$alkyl or $(C_1-C_{12})$alkyl$(C_6-C_{10})$aryl. For example, the $(C_1-C_{20})$alkyl can be a straight, branched, or cyclic $(C_1-C_{12})$alkyl group, such as methyl, ethyl, propyl, or isopropyl. The $(C_1-C_{12})$alkyl$(C_6-C_{10})$aryl group can be, for example, benzyl or phenylethyl. Any R' or R" group can be substituted with one or more (e.g., one to about five) substituents as described above in the definition of substitutents. Examples include halo or amino groups, including alkyl-amino and dialkyl-amino groups, and/or aryl groups including phenyl and naphthyl, among others. R' and R" taken together can form cyclic acetals, such as those formed from a $(C_1-C_{12})$diol or dialkoxy aryl compound, such as 1,2-dimethoxybenzene (veratrole). The cyclic acetals can include (other than the acetal heteroatoms) one to about three heteroatoms in the ring, such as O, S, or N, and the ring can be substituted, for example, with various substituents such as methyl or phenyl groups.

Representative compounds of formulas I-IV include any of the following:

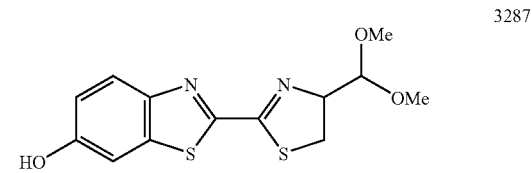

3287

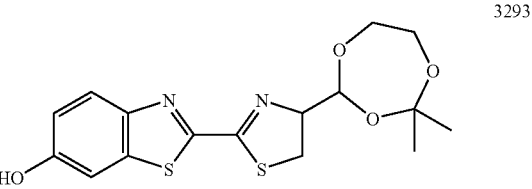

3293

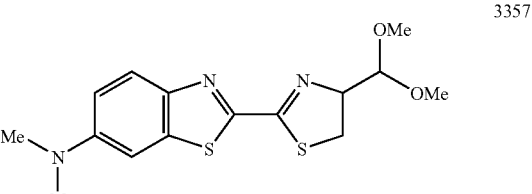

3357

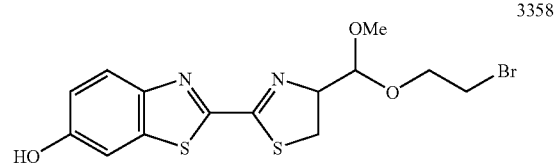

3358

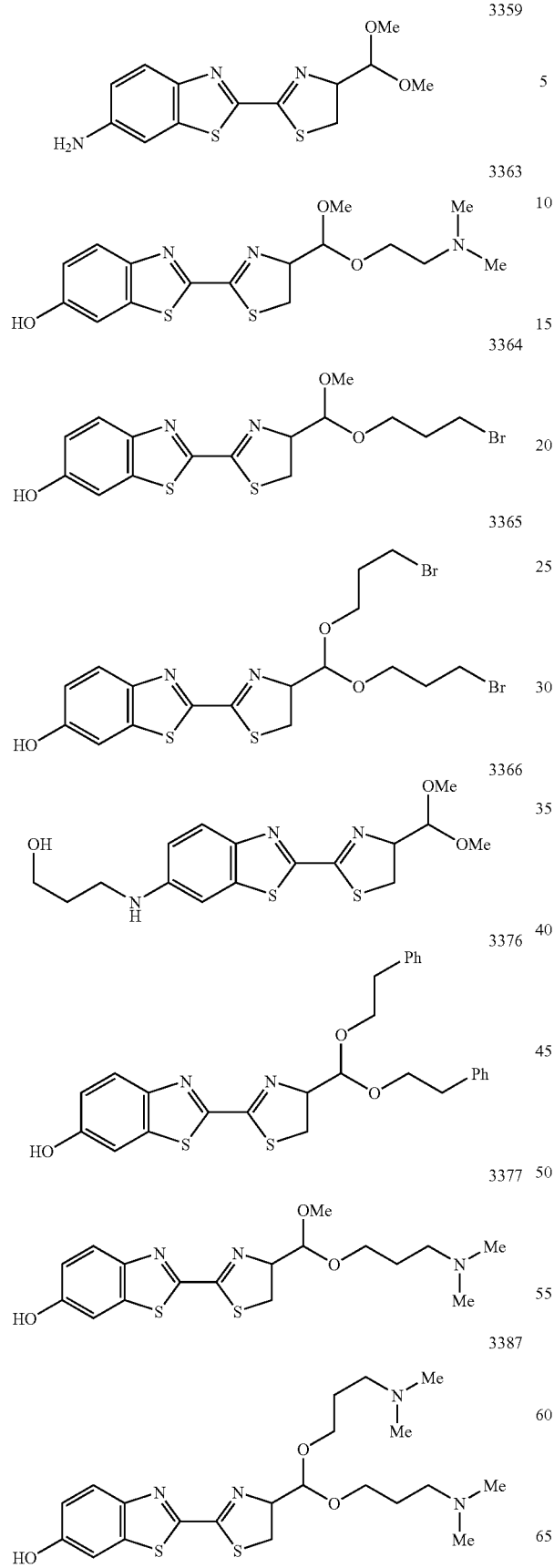
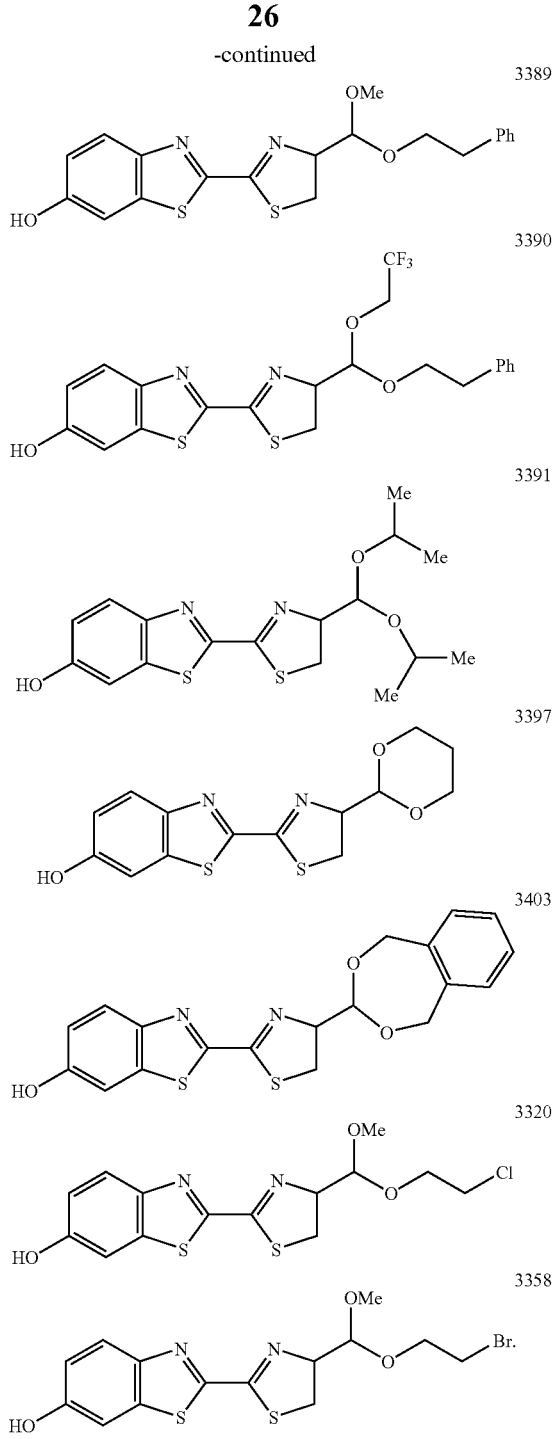

Other derivatives and their use in luminogenic assays are described herein below.

Use of the luciferin derivatives described herein results in an assay that produces a measurable change in optical properties upon interaction with a nonluciferase molecule. The interaction can alter the structure of the luciferin derivative. As described herein, the product of a reaction between a luciferin derivative and a nonluciferase enzyme or other molecule of interest need not be D-luciferin or aminoluciferin. For example, a luciferin derivative may include a substrate that includes a reactive chemical group for a nonluciferase enzyme linked to luciferin or aminoluciferin via a chemical linker. Transformation of the reactive chemical group of the derivative by the nonluciferase enzyme may yield a product that contains (retains) a portion of the substrate, a portion of the chemical linker, the chemical linker, or a portion of the substrate and the chemical linker, and that product is a substrate for luciferase. Luciferin derivatives in which the backbone of luciferin is further modified in its ring structure, e.g., a quinolyl or naphthyl luciferin, are provided, as well as advantageously providing modifications at the carboxy position of the thiazole ring, to provide improved characteristics to the luciferin derivative. Derivatives with certain modifications provide for or improve assays for certain nonluciferase enzymes or molecules. Thus, bioluminescent methods that employ a luciferin derivative of the invention may be used to detect one or more molecules, e.g., an enzyme, a cofactor for an enzymatic reaction, an enzyme substrate, an enzyme inhibitor, or an enzyme activator.

Derivatives of the invention include certain luciferins, quinolinyl luciferins, aminoquinolinyl luciferins, naphthyl luciferins, and fluorinated derivatives thereof. For instance, the optical properties of fluorinated derivatives of aminoquinolinyl luciferin may be altered due to the electron withdrawing power of fluorine. Fluorinated derivatives include a compound of formula V and VI:

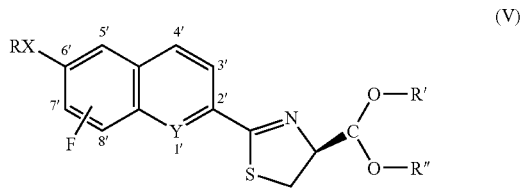
(V)

wherein X=O or NH; Y=N or CH; and F may be at 3', 4', 5', 7', or 8';

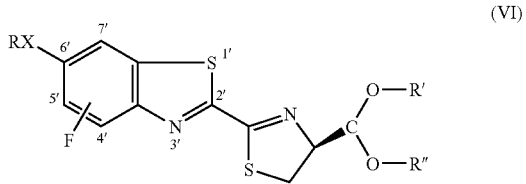
(VI)

wherein X=O or NH; and F may be at 4', 5', or 7'; and R can be as defined for formula I.

In one embodiment, the invention provides for quinolinyl derivatives (compounds of formula VII-XI):

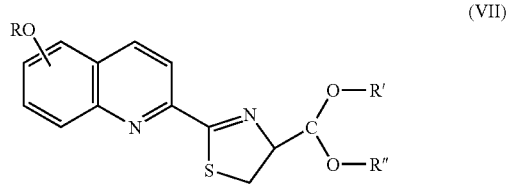
(VII)

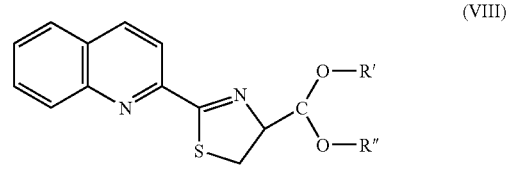
(VIII)

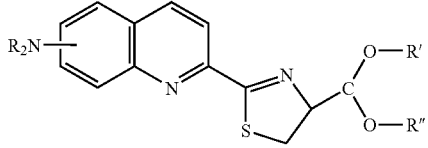
(IX)

wherein OR or $NR_2$ can replace any H on a quinolinyl ring, in some embodiments, at positions 6' and/or 8', and R, R', and R" can be as defined for formula I.

In one embodiment, each of $K^1$-$K^4$ is CH or C (e.g., C when substituted and CH when unsubstituted). In some embodiments, one of $K^1$, $K^2$, $K^3$, or $K^4$ is N-oxide, and Z is H, OH, or amino. Z can also be OR or optionally substituted amino. In some embodiments, 1, 2, 3, or 4 $W^1$ groups are present. Each $W^1$ can independently be, for example, F, Cl, Br, or I.

In one embodiment, each X* is O. In another embodiment, at least one X* is S. In one embodiment, R' and R" are each independently optionally substituted ($C_1$-$C_{12}$)alkyl. In one embodiment, R' and R" together with —X*—CH—X*— to which they are attached form a 5-12 membered optionally substituted heterocycle group. One or more members of the 5-12 membered optionally substituted heterocycle group, in addition to X*, can be O, S, or NR wherein R is H or ($C_1$-$C_{12}$)alkyl. In one embodiment, R' and R" form a cyclic acetal optionally substituted with an ortho-fused benzo group.

In one embodiment, Y is N or CH; X is S or O; and the dotted line in ring B is present to form a double bond. In some embodiments, ring B is a 6-membered ring; Y is N or CH; X is CH=CH, N=CH, or CH=N; and the dotted line in ring B is present to form a double bond.

In one embodiment, Z is OH or OR, wherein R is an optionally substituted ($C_1$-$C_{20}$)alkyl, ($C_6$-$C_{30}$)aryl, or ($C_1$-$C_{12}$)alkyl-($C_6$-$C_{14}$)aryl group. In some embodiments, Z is OR and R is phenyl or benzyl, optionally substituted with one to five halo, nitro, trifluoromethyl, amino, alkylamino, dialkylamino, phosphate, alkyl, alkylcarboxyl, or alkoxycarbonyl groups.

In one embodiment, Z is NRR wherein each R is H, an optionally substituted ($C_1$-$C_{12}$)alkyl, or a nitrogen protecting group.

In one embodiment, each X* is O, Z is OR, and R' and R" are each optionally substituted ($C_1$-$C_{12}$)alkyl.

In one embodiment, each X* is O, Z is NRR, and R' and R" are each optionally substituted ($C_1$-$C_2$)alkyl.

In one embodiment, Y is N; X is S or —CH=CH—; $W^1$ is H, F, or Cl, and up to three $W^1$ substituents are be present; $W^2$ is H; $K^1$, $K^2$, $K^3$, and $K^4$ are all C or CH; and Z', A', and B' are each absent.

In one embodiment, Y is N; X is S; X* is O.

In one embodiment, Z is located at the 6' position of the A ring, Z is OH, $NH_2$, $NMe_2$ or $NHCH_7CH_2CH_2OH$; and $W^1$ is H, F, or Cl, located at the 5' position of the A ring.

In some embodiments, R can be a hydroxy($C_2$-$C_{12}$)alkyl group such as 2-hydroxyethyl, 3-hydroxypropyl, 4-hydroxybutyl, 5-hydroxypentyl, 6-hydroxyhexyl, 8-hydroxyoctyl, or 10-hydroxydecyl, and the like.

In some embodiments, R can be ($C_1$-$C_{12}$)alkyl, ($C_1$-$C_{10}$) alkyl, ($C_1$-$C_8$)alkyl, ($C_1$-$C_6$)alkyl, ($C_1$-$C_4$)alkyl, ($C_4$-$C_{12}$) alkyl, ($C_6$-$C_{12}$)alkyl, or ($C_8$-$C_{12}$)alkyl. Specific examples are recited in the definition of alkyl above. The alkyl groups can be substituted with various groups, including other or additional R groups. For example, the terminal carbon of an alkyl group can be substituted by a hydroxy or alkoxy and/or an oxo group. Accordingly, the R group can be an alkyl carboxylate, such as methoxy ethanoate or ethanolic acid (e.g. wherein the alkyl group is oxidized at the terminal carbon). Other terminal carboxylic acid R groups include $C_4$ and $C_6$ derivatives. Other R groups can be alkyl groups that terminate in amino groups, ammonium groups, azide groups, or acetyl amino groups.

suitable substituent. Thus, the R group of the Z group connecting the formula I moieties of the dimer of formula I is replaced by the linker, which can also be referred to as a bridge. Examples of acetal dimers of the invention include the following compounds:

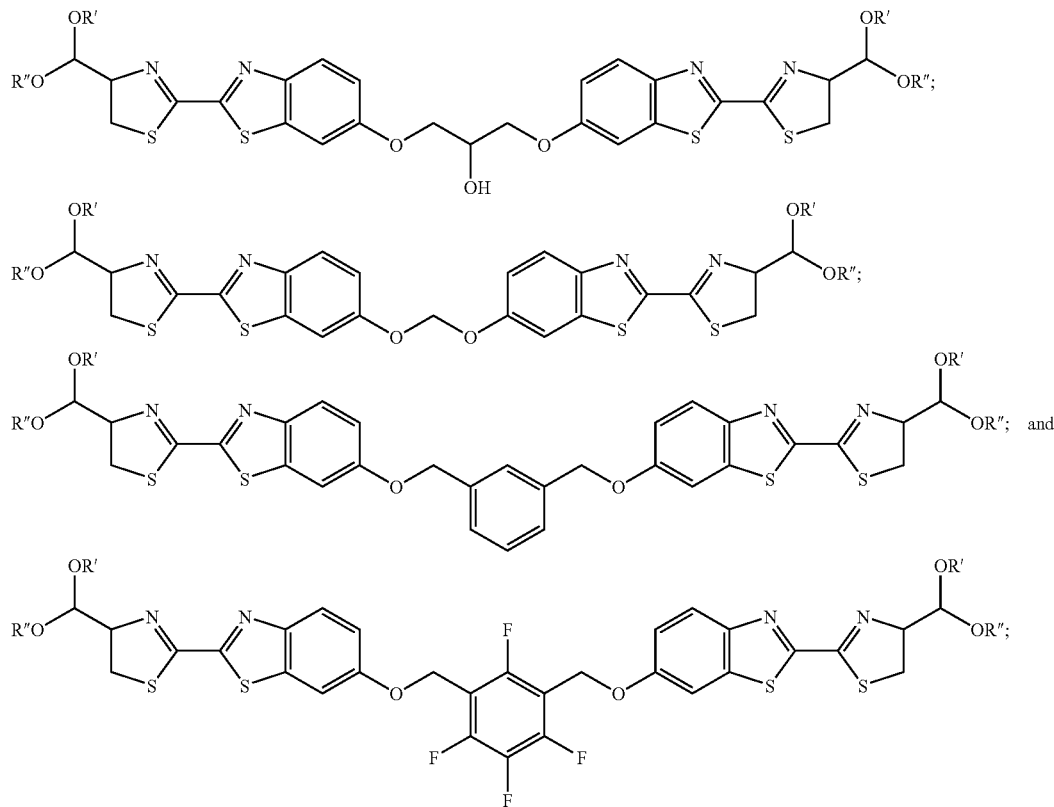

wherein R' and R" are as defined for formula I. These dimers can be prepared by techniques analogous to the monomeric formula I compounds, using an acetal aminothiol in place of the D-cysteine in the cyclization step. In some embodiments, one or more (e.g., one, two, three, or four) of the acetal oxygen atoms may be individually replaced with a sulfur atom.

IV. Agents Useful to Stabilize Light Production in Luciferase-Mediated Reactions Organic agents can be useful to stabilize light production in certain reactions described herein, including luciferase-mediated reactions. The organic agents include certain organic compounds (i.e., compounds that comprise one or more carbon atoms). Such an agent may be added prior to, at the initiation of and/or during a nonluciferase enzyme-mediated reaction or a luciferase-mediated reaction. Suitable organic compounds and methods of their use include those described in U.S. Pat. No. 7,118,878 (Hawkins et al.), the disclosure of which is incorporated herein by reference.

In another aspect of the invention, a reagent, method, and kit for stabilizing luminescence-based reactions is provided. The use of certain luciferase stabilizing molecules, such as reversible inhibitors of luciferase, may provide a protective effect against the known self-catalyzed auto-degradation of the luciferase enzyme, thus prolonging the luminescence sig- In some embodiments, R can be an aralkyl group, for example, a aryl-$(C_1-C_{12})$alkyl. Examples include benzyl, phenethyl, phenylpropyl, phenylbutyl, phenylpentyl, phenylhexyl, phenyloctyl, phenyldecyl, and the like. The phenyl group and/or the alkyl group can be substituted, for example, by one or more substitutents. The substituents can be other or additional R groups. Examples of aryl or phenyl substituents include one, two, or three —$NR^aR^b$ groups, wherein $R^a$ and $R^b$ are each independently H, $(C_1-C_{10})$alkyl, aryl$(C_1-C_{10})$alkyl, $(C_1-C_{10})$alkyl-carbonyl, $(C_1-C_{10})$alkoxycarbonyl, or a nitrogen protecting group, such as benzyl, benzoyl, or carbonylbenzyloxy. A phenyl group can be substituted ortho, meta, or para to the phenyl group's point of attachment to the rest of the formula.

In some embodiments, formula I can be linked to a second formula I to provide a dimer. The dimer can be linked together, for example, by the Z group attached to the A rings of each acetal derivative. The group Z can be a linker between the two acetal derivatives. For example, Z can be OR wherein R is a divalent linker, such as an optionally substituted $(C_1-C_{12})$alkyl diradical that is optionally interrupted by one to four O atoms, N atoms, or an optionally substituted aryl, heteroaryl, or heterocycle group to form a bridge between the formula I moieties. In some embodiments, the linker, such as the $(C_1-C_{12})$alkyl, can be substituted by one to four oxo groups and/or one to four hydroxyl groups, or any other nal and facilitating batch processing of reaction mixtures. Suitable reagents, methods, and kits for stabilizing luminescence-based reactions are described in U.S. Patent Publication No. 2004/0171099 (Cali et al.), the disclosure of which is incorporated herein by reference.

V. Kits

The present invention also provides kits for detecting the presence or activity of one or more molecules which are reagents for a reaction, enhance or inhibit a reaction, or for detecting a condition in a sample such as a sample including intact cells, a cell lysate, e.g., a lysate which is at least partially purified, or a cellular supernatant. In one embodiment, the kit includes a compound of the invention. For kits of the invention that include two or more of the following, a derivative of luciferin or aminoluciferin (e.g., an acetal compound as described herein), another substrate, an enzyme, e.g., an esterase, or a reaction mixture, each can be contained in a separate container. Some components may be combined in some containers, or they can be contained in a single container.

The kit can optionally include a buffer solution suitable for use in an assay, and the compound or enzyme, and the buffer solution can optionally be contained in a single container. The derivative and the buffer solution can optionally be contained in a single container. The kits can also optionally include a quenching agent for a nonbioluminescent reaction. The kits can further optionally contain a non-luciferase enzyme to be assayed with some or all of its necessary or optional cofactors. The kits can also contain a luciferase reaction mixture for detecting the product of a first reaction with a compound described herein. Additionally, the kit can include a protocol or instructions for use.

The invention will be described by the following non-limiting examples.

EXAMPLES

Material and Methods

The following materials and methods were used in the experiments described in Examples 1 and 2.

Materials

Compounds were prepared that are proluciferin acetals. The compounds examined in Examples 1 and 2 were given the arbitrary numeric designations 3320, 3357, 3358, 3359, 3363, 3364, 3365, 3366, 3377, 3387, 3391, 3397 and 3403, and their structures are shown in FIG. 2 and FIGS. 8-20. Luciferin-PPXE: (S)-2-(6-(3-((4-phenylpiperazin-1-yl)methyl)benzyloxy)benzo[d]thiazol-2-yl)-4,5-dihydrothiazole-4-carboxylic acid, luciferin-PFBE: (S)-2-(6-(perfluorobenzyloxy)-benzo[d]thiazol-2-yl)-4,5-dihydrothiazole-4-carboxylic acid, and Luciferin-BE: (S)-2-(6-(benzyloxy)benzo[d]thiazol-2-yl)-4,5-dihydrothiazole-4-carboxylic acid were obtained from Promega Corporation. P450 enzymes are provided as membrane fractions from an insect cell expression system in which the P450 enzyme has been co-expressed with P450 reductase (Supersomes™; Discovery Labware). CYP2A6, 2B6, 2C8, 2C9, 2C19, 2E1, 2J2, 3A4, 3A5, 3A7, 4F2, 4F3A, 4F3B and 4F12 membrane fractions also contain co-expressed cytochrome b5. Control samples are membrane preparations which do not express a P450 enzyme and are prepared from the same insect cell expression system as the P450 enzymes (control Supersomes™; Discovery Labware).

Luciferin Detection Reagent (LDR) consisting of two components is commercially available from Promega Corporation. Briefly, the first component consists of a lyophilized preparation of a recombinant firefly luciferase. The first component is reconstituted with the second component, a luciferase reaction buffer containing ATP, an active esterase enzyme for processing luciferin ester P450 reaction products, and a detergent for stopping the P450 enzyme activity. LDR is used to detect the P450-dependent conversion of proluciferin to luciferin.

Human hepatocytes, harvested from a 16 year old human donor, were purchased from Lonza.

Methods

For assays using recombinant P450 enzymes, a two-step scheme was followed whereby a luciferin derivative is oxidized by a P450 enzyme in a first step. In the second step, LDR is added to the P450 reaction mixture to stop the P450 activity and initiate a glow-style luciferase reaction whereby the luminescent signal strength is dependent on the amount of luciferin derivative oxidized by a P450 enzyme in the first step.

Reaction buffers for the P450 enzyme reaction of the first step varied depending on the P450 enzyme used. Buffers were used according to the enzyme manufacturer's suggestion. Unless otherwise indicated, the following buffer/enzyme combinations were used: 100 mM $KPO_4$, pH 7.4 for CYP1A1, 1A2, 1B1, 2D6, 2E1, 3A5, 3A7, 2J2, 4F12, 19, and control samples; 50 mM $KPO_4$, pH 7.4 for CYP2B6, 2C8, 2C19, 4F2, 4F3A, 4F3B; 25 mM $KPO_4$, pH 7.4 for CYP2C9; 200 mM $KPO_4$, pH 7.4 for CYP3A4; 100 mM TrisHCl, pH 7.5 for CYP2A6, 2C18, 4A11.

In FIG. 2 and FIGS. 8-19, luciferin derivatives were screened against a panel of recombinant human cytochrome P450 enzyme and control microsomes (Supersomes™). Concentrated stock solutions of the proluciferin acetal compounds were prepared as follows: 50 mM 3320, 3357, 3364, 3366 and 3391 in acetonitrile; 50 mM 3359, 3365, 3397 and 3403 in dimethyl sulfoxide (DMSO); 50 mM 3377 in $H_2O$; 10 mM 3363 in $H_2O$. Luciferin-PPXE, luciferin-PFBE and luciferin-BE were provided as a 50 mM solution in DMSO, 2 mM solution in 25 mM Tris, pH 8 and a 5 mM solution in 100 mM $KPO_4$, pH 7.4, respectively. Assays were performed in opaque, white, polystyrene, flat-bottom 96-well plates. Each compound was diluted to 50 µM in 50 µl of the appropriate P450 reaction buffer with 1 pmole P450 enzyme or an equivalent volume of control membranes and an NADPH regenerating system (1.3 mM NADP+, 3.3 mM glucose-6-phosphate, 3.3 mM $MgCl_2$ and 0.4 U/mL glucose-6-phosphate dehydrogenase). The reactions were initiated by addition of the NADPH regenerating system and incubated for 30 minutes at 37° C. After incubation, an equal volume (50 µl) of LDR is added and luminescence read 20 minutes later at room temperature on a Veritas™ luminometer.

Figure 20:
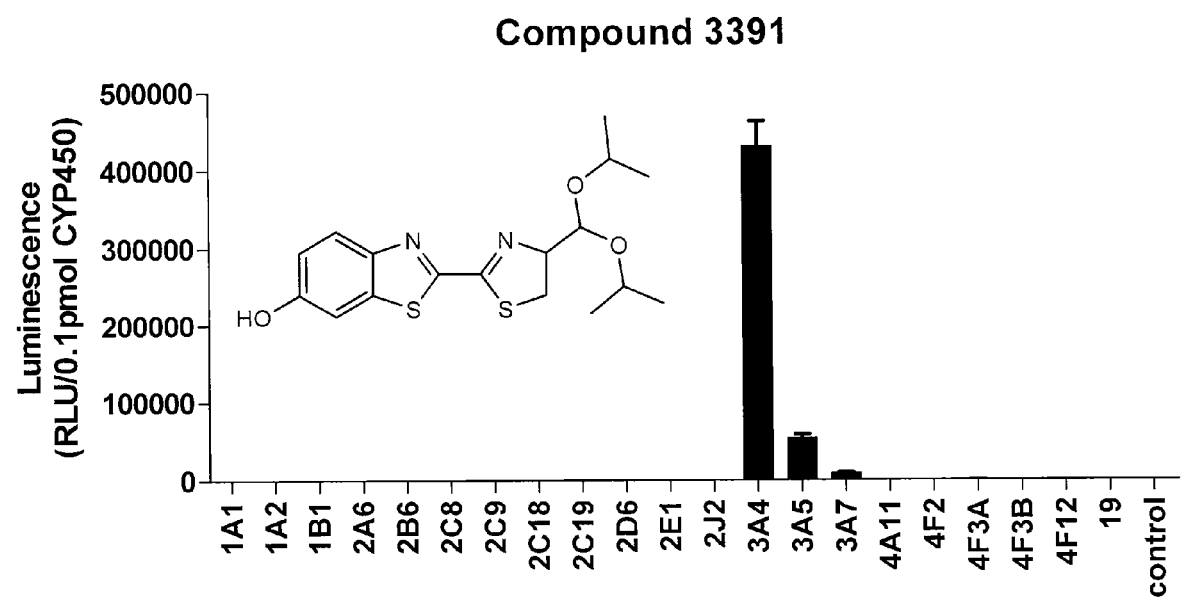
FIG. 20. P450 enzyme selectivity of compound 3391. A graphical representation of luminescence given in relative light units (RLU) for reactions containing acetal proluciferin derivative compound 3391 screened against a panel of recombinant cytochrome P450 enzymes. The mean and standard deviation of measurements from three replicate reactions with each P450 enzyme are shown. This figure differs from FIG. 2 as described in Example 1 and in its Materials and Methods section.

In FIG. 20 using compound 3391, the method used in FIGS. 2 and 8-19 was used with the following changes: 0.1 picomole of each P450 enzyme or an equivalent volume of control membranes was used per reaction; for all reactions, 2 µM compound 3391 was used, 100 mM $KPO_4$, pH 7.4 was used as the P450 reaction buffer, and the reaction was incubated for 10 minutes at 37° C.

In FIGS. 3-6, CYP3A4 enzyme was co-expressed with cytochrome b5 and cytochrome P450 reductase in membrane fractions (Supersomes™). For each 50 µl reaction, 0.1 pmol of CYP3A4 enzyme was combined in 200 mM $KPO_4$ buffer, pH 7.4 with 2.0 µM compound 3391, an NADPH regenerating system (1.3 mM NADP+, 3.3 mM glucose-6-phosphate, 3.3 mM $MgCl_2$ and 0.4 U/mL glucose-6-phosphate dehydrogenase), and amounts of each inhibitor (Nifedipine, Ketoconazole, Testosterone or Midazolam) as indicated in FIGS.

3-6. The reactions were initiated by addition of the NADPH regenerating system and incubated for 10 minutes at 37° C. After incubation, an equal volume (50 µl) of LDR was added and luminescence read 20 minutes later at room temperature on a Veritas™ luminometer. Signals are expressed as "% activity" where 100% represents luminescence observed in the absence of an inhibitor. $IC_{50}$ is the concentration of inhibitor that causes 50% inhibition of the reaction. Curve fits and $IC_{50}$ calculations were performed with the program Graph-Pad Prism™.

Figure 7:
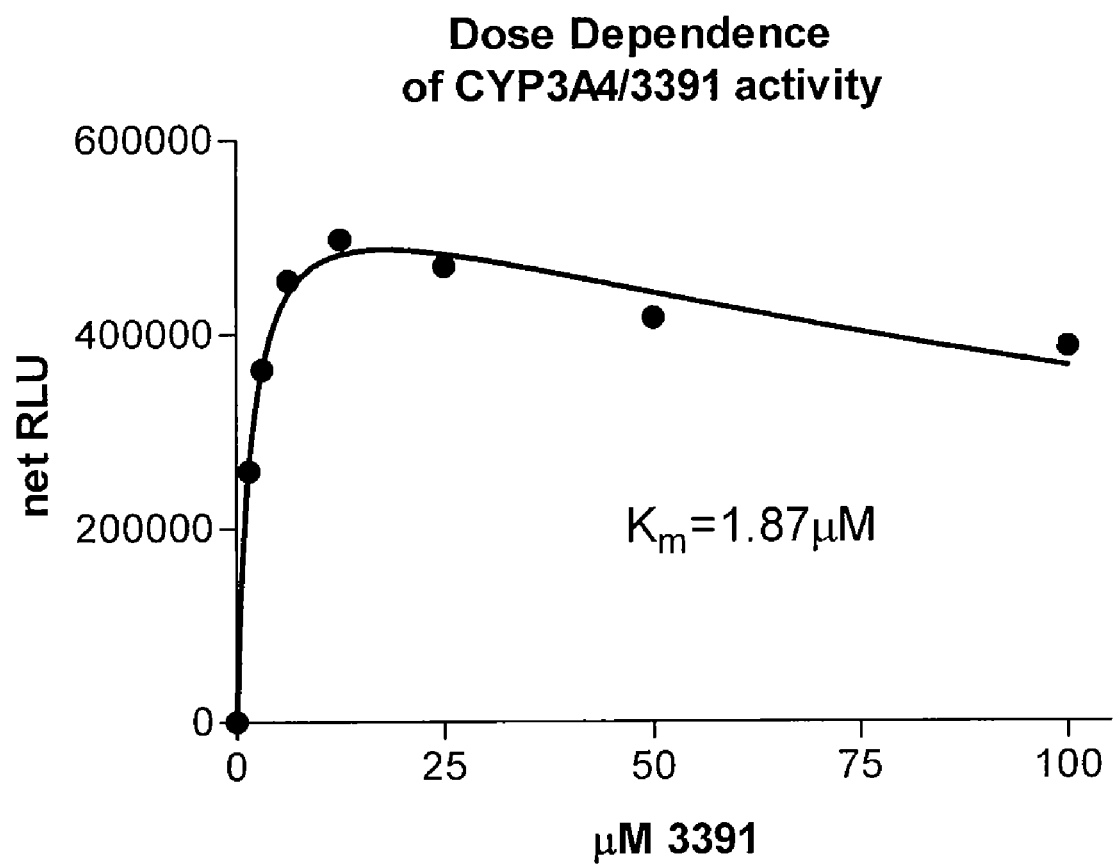
FIG. 7. Dose dependence of CYP3A4/3391 activity.
Figure 8:
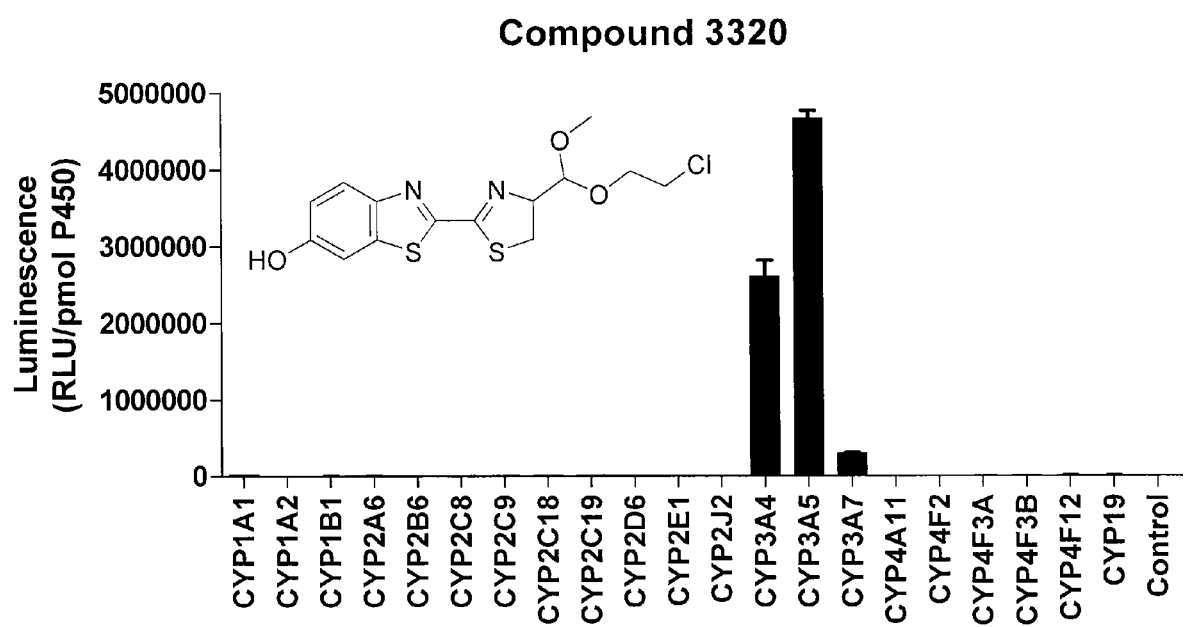
FIG. 8. P450 enzyme selectivity of compound 3320. A graphical representation of luminescence given in relative light units (RLU) for reactions containing acetal proluciferin derivative compound 3320 screened against a panel of recombinant cytochrome P450 enzymes. The mean and standard deviation of measurements from three replicate reactions with each P450 enzyme are shown.
Figure 9:
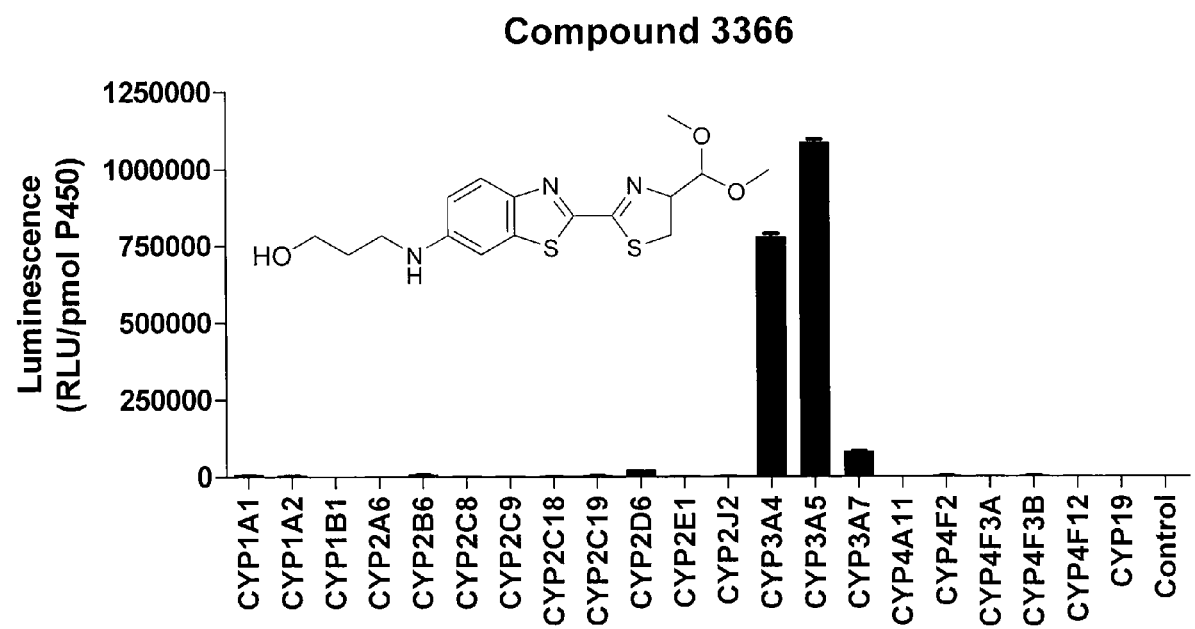
FIG. 9. P450 enzyme selectivity of compound 3366. A graphical representation of luminescence given in relative light units (RLU) for reactions containing acetal proluciferin derivative compound 3366 screened against a panel of recombinant cytochrome P450 enzymes. The mean and standard deviation of measurements from three replicate reactions with each P450 enzyme are shown.
Figure 10:
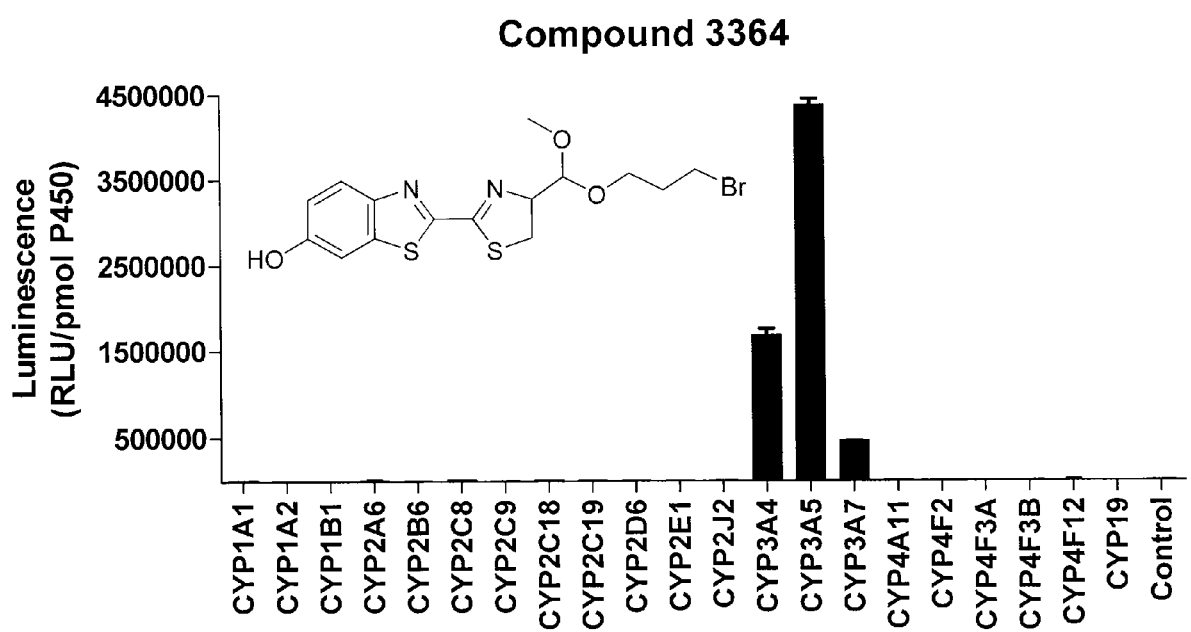
FIG. 10. P450 enzyme selectivity of compound 3364. A graphical representation of luminescence given in relative light units (RLU) for reactions containing acetal proluciferin derivative compound 3364 screened against a panel of recombinant cytochrome P450 enzymes. The mean and standard deviation of measurements from three replicate reactions with each P450 enzyme are shown.
Figure 11:
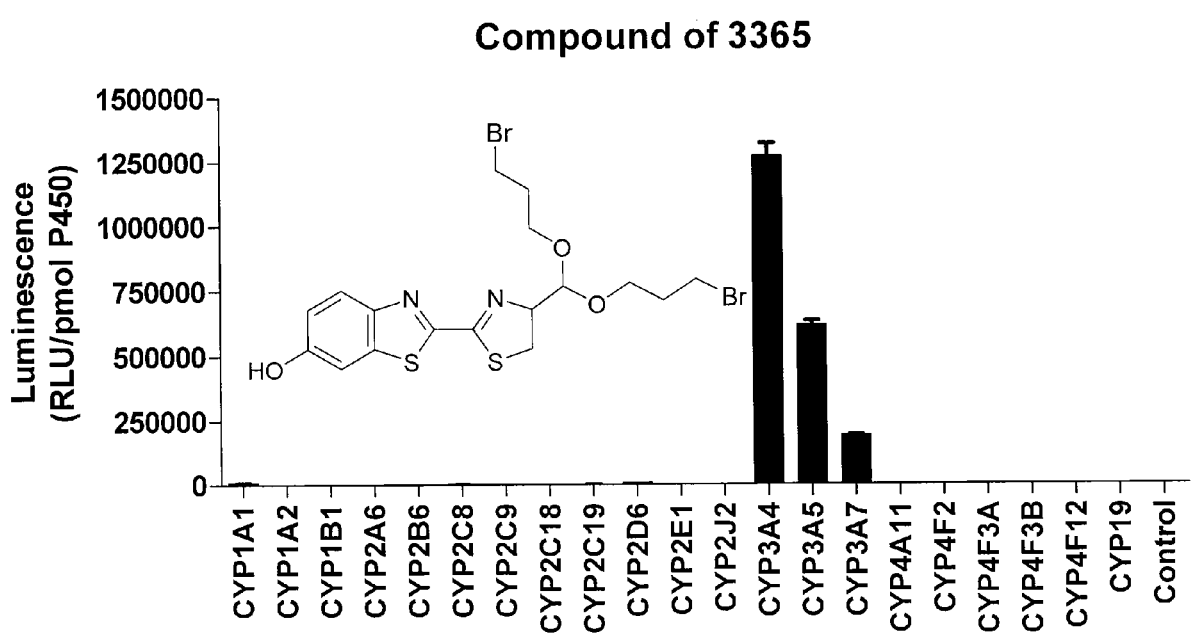
FIG. 11. P450 enzyme selectivity of compound 3365. A graphical representation of luminescence given in relative light units (RLU) for reactions containing acetal proluciferin derivative compound 3365 screened against a panel of recombinant cytochrome P450 enzymes. The mean and standard deviation of measurements from three replicate reactions with each P450 enzyme are shown.
Figure 12:
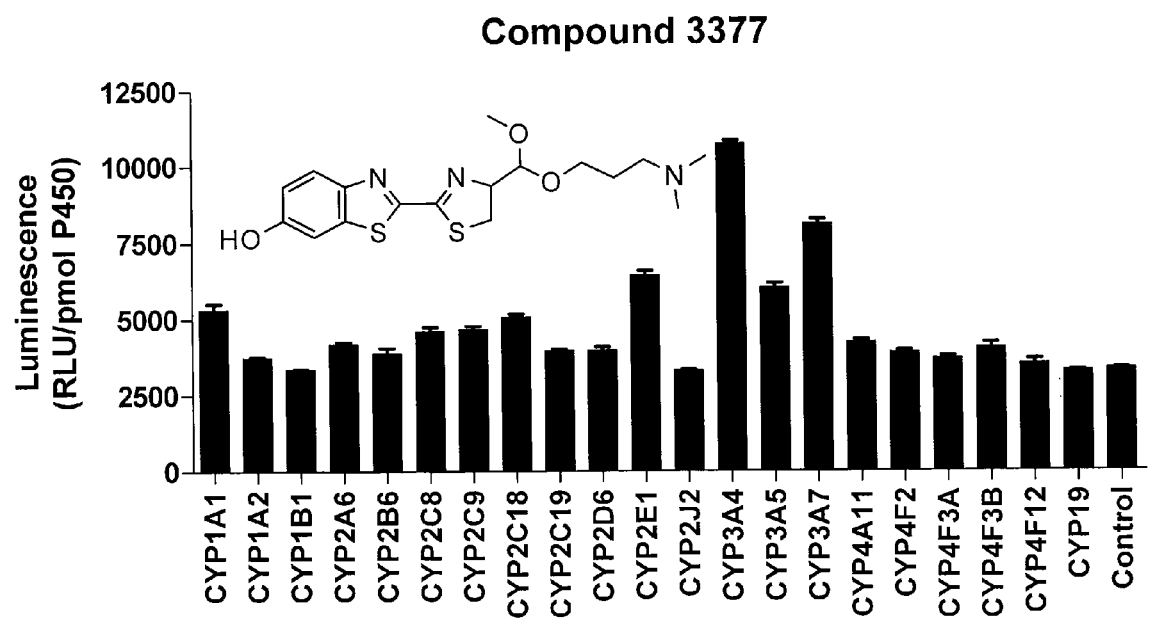
FIG. 12. P450 enzyme selectivity of compound 3377. A graphical representation of luminescence given in relative light units (RLU) for reactions containing acetal proluciferin derivative compound 3377 screened against a panel of recombinant cytochrome P450 enzymes. The mean and standard deviation of measurements from three replicate reactions with each P450 enzyme are shown.
Figure 13:
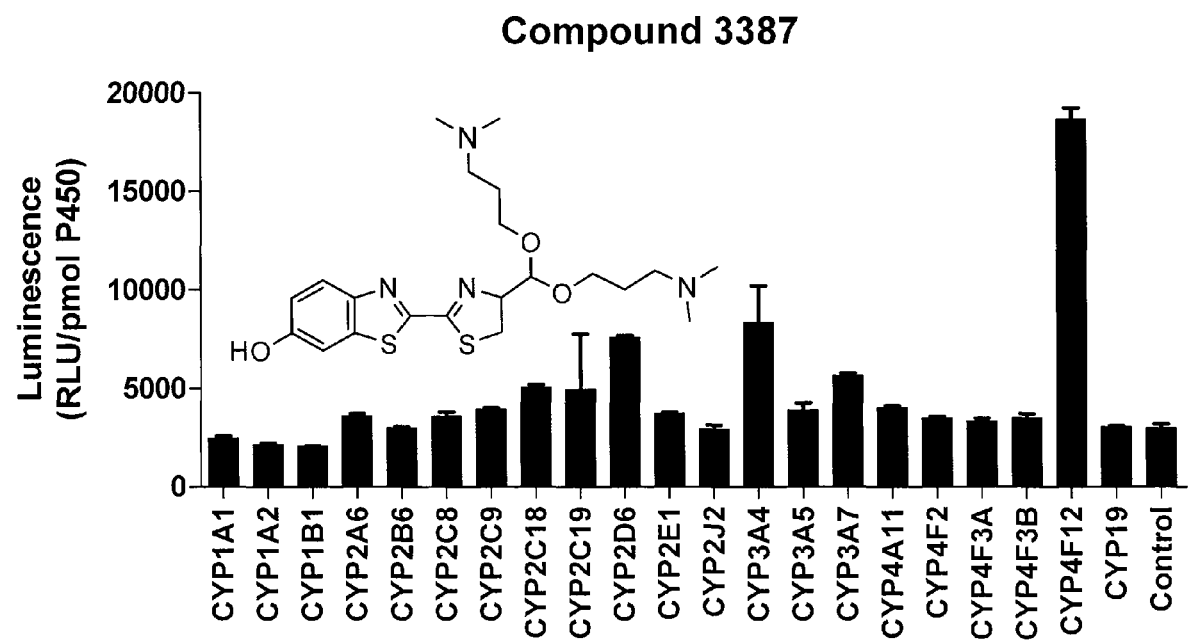
FIG. 13. P450 enzyme selectivity of compound 3387. A graphical representation of luminescence given in relative light units (RLU) for reactions containing acetal proluciferin derivative compound 3387 screened against a panel of recombinant cytochrome P450 enzymes. The mean and standard deviation of measurements from three replicate reactions with each P450 enzyme are shown.
Figure 14:
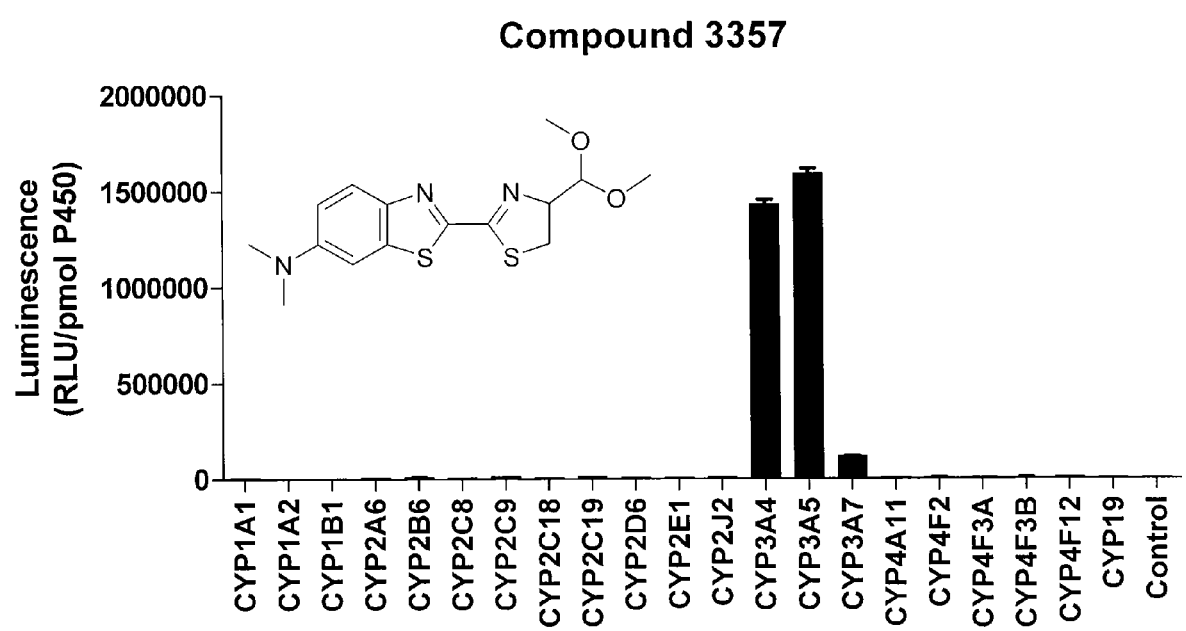
FIG. 14. P450 enzyme selectivity of compound 3357. A graphical representation of luminescence given in relative light units (RLU) for reactions containing acetal proluciferin derivative compound 3357 screened against a panel of recombinant cytochrome P450 enzymes. The mean and standard deviation of measurements from three replicate reactions with each P450 enzyme are shown.
Figure 15:
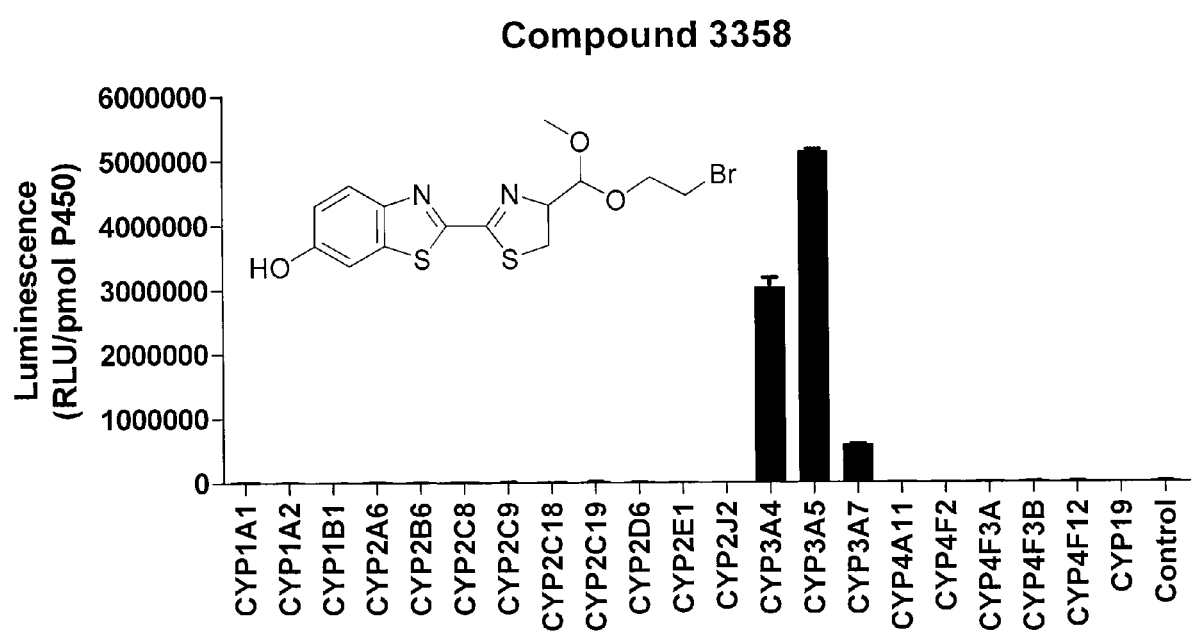
FIG. 15. P450 enzyme selectivity of compound 3358. A graphical representation of luminescence given in relative light units (RLU) for reactions containing acetal proluciferin derivative compound 3358 screened against a panel of recombinant cytochrome P450 enzymes. The mean and standard deviation of measurements from three replicate reactions with each P450 enzyme are shown.
Figure 16:
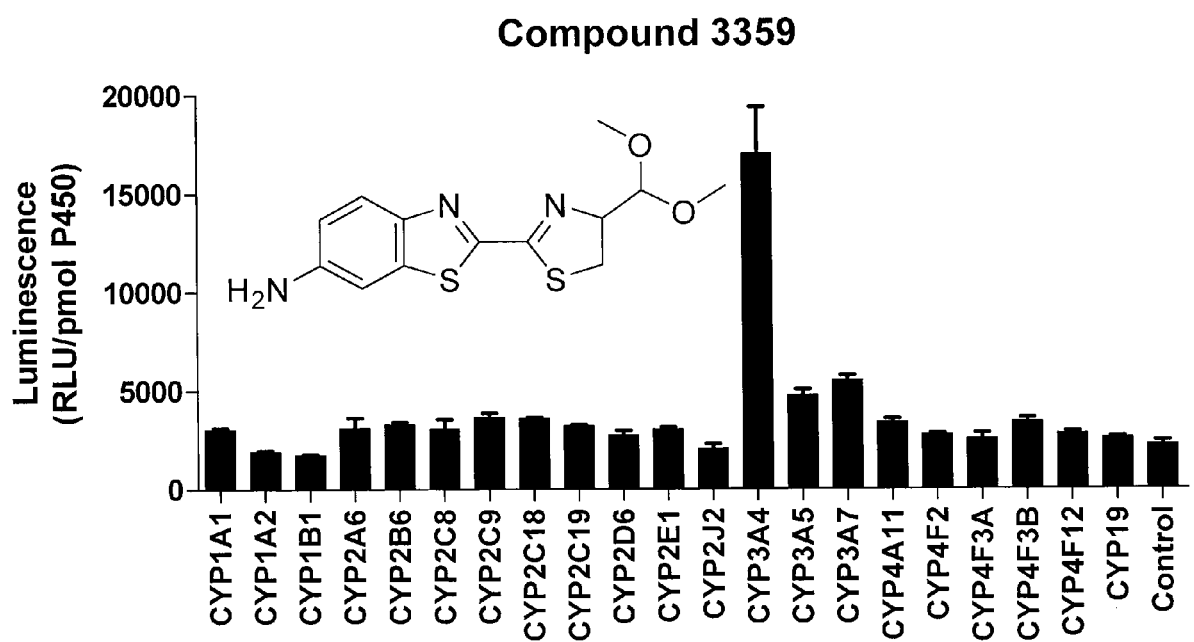
FIG. 16. P450 enzyme selectivity of compound 3359. A graphical representation of luminescence given in relative light units (RLU) for reactions containing acetal proluciferin derivative compound 3359 screened against a panel of recombinant cytochrome P450 enzymes. The mean and standard deviation of measurements from three replicate reactions with each P450 enzyme are shown.
Figure 17:
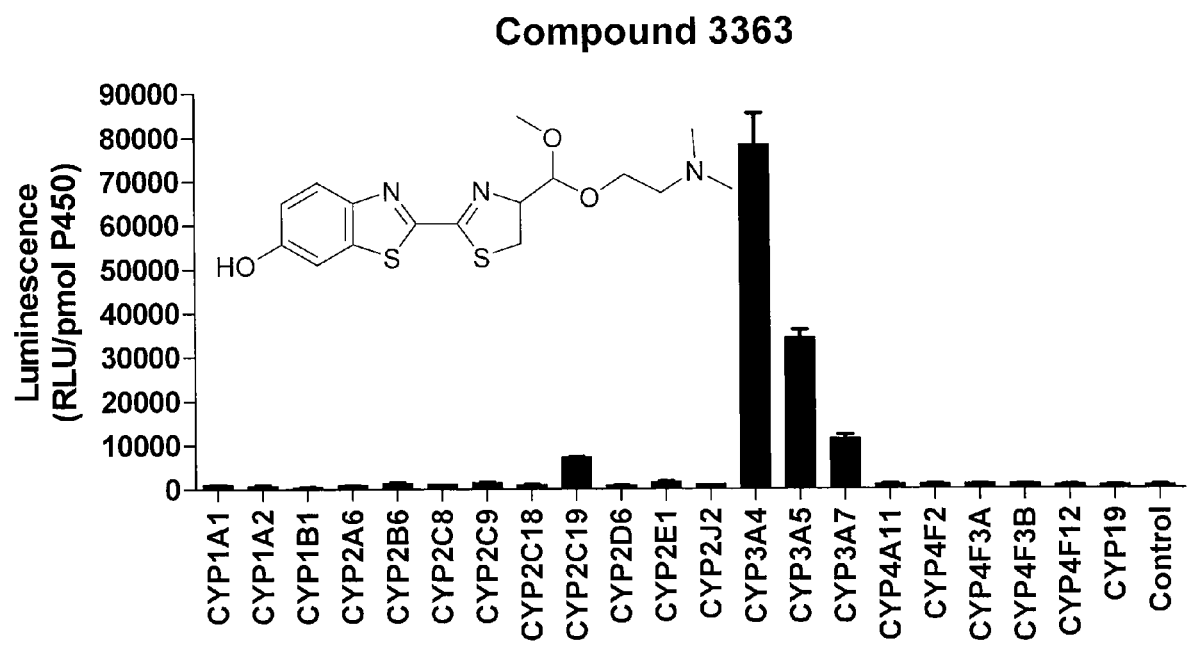
FIG. 17. P450 enzyme selectivity of compound 3363. A graphical representation of luminescence given in relative light units (RLU) for reactions containing acetal proluciferin derivative compound 3363 screened against a panel of recombinant cytochrome P450 enzymes. The mean and standard deviation of measurements from three replicate reactions with each P450 enzyme are shown.
Figure 18:
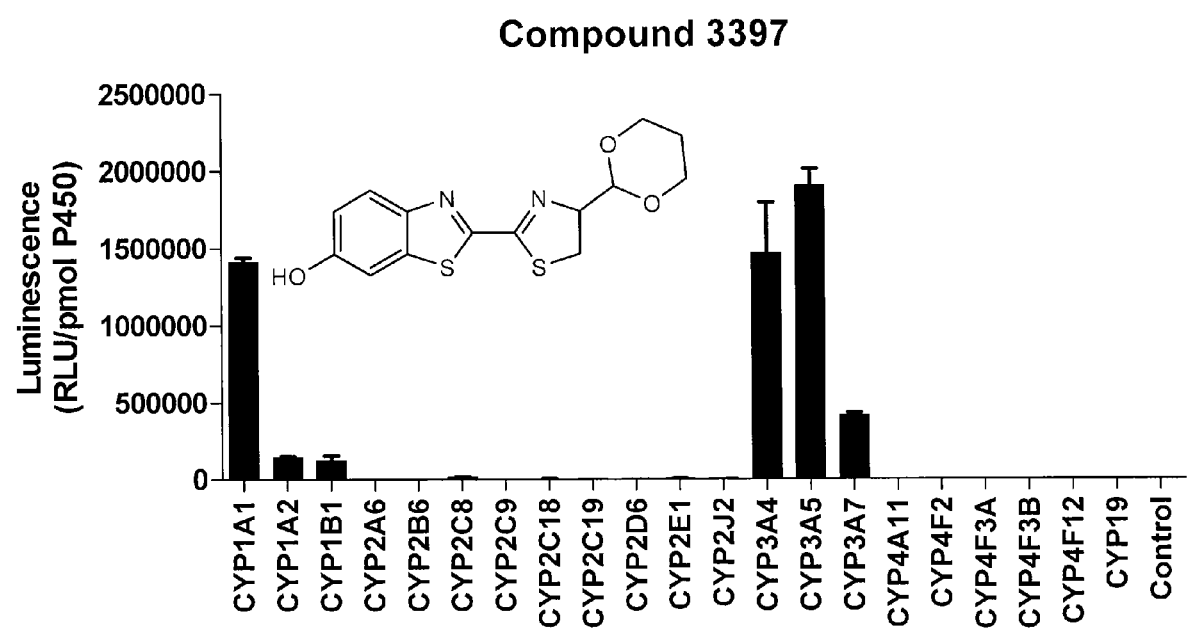
FIG. 18. P450 enzyme selectivity of compound 3397. A graphical representation of luminescence given in relative light units (RLU) for reactions containing acetal proluciferin derivative compound 3397 screened against a panel of recombinant cytochrome P450 enzymes. The mean and standard deviation of measurements from three replicate reactions with each P450 enzyme are shown.
Figure 19:
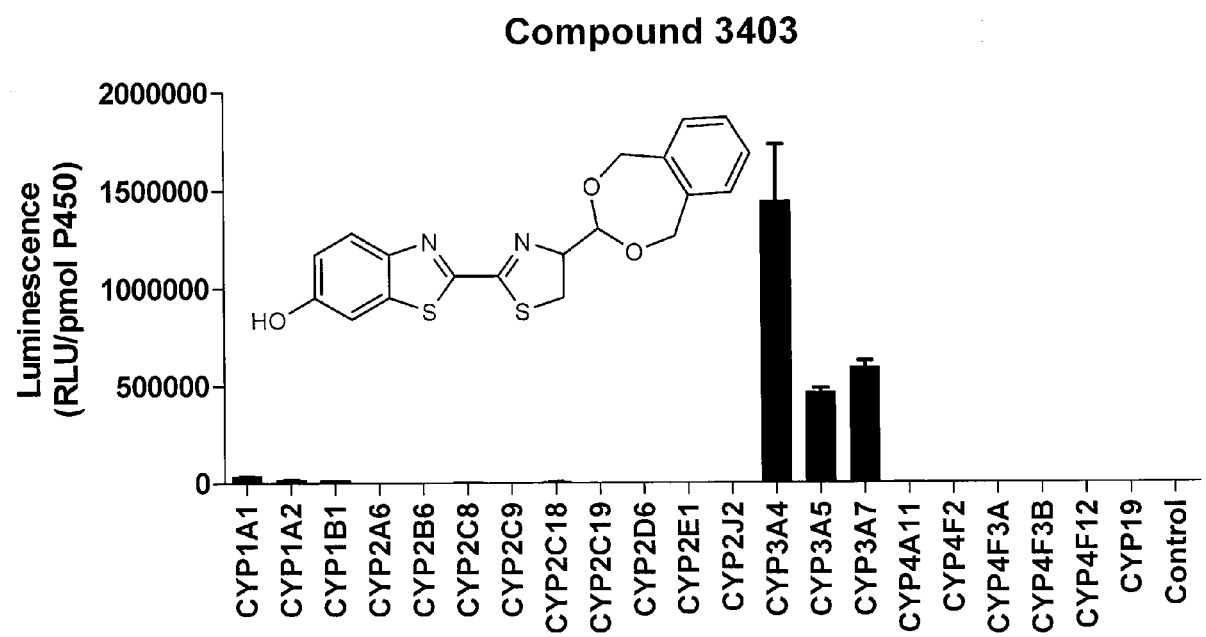
FIG. 19. P450 enzyme selectivity of compound 3403. A graphical representation of luminescence given in relative light units (RLU) for reactions containing acetal proluciferin derivative compound 3403 screened against a panel of recombinant cytochrome P450 enzymes. The mean and standard deviation of measurements from three replicate reactions with each P450 enzyme are shown.

In FIG. 7, the dose dependence of the CYP3A4 reaction with 3391 was demonstrated. The reactions were performed as described for FIGS. 3-6 except no inhibitors were present in the reactions, and the concentration of compound 3391 varied as indicated in FIG. 7. Signals are expressed as net relative luminescent units (RLU) calculated by subtracting the background RLU values of control reaction mixtures that lack CYP3A4 enzyme from the RLU values of the CYP3A4 reactions. The curve fit was performed with the program GraphPad Prism™.

Figure 21:
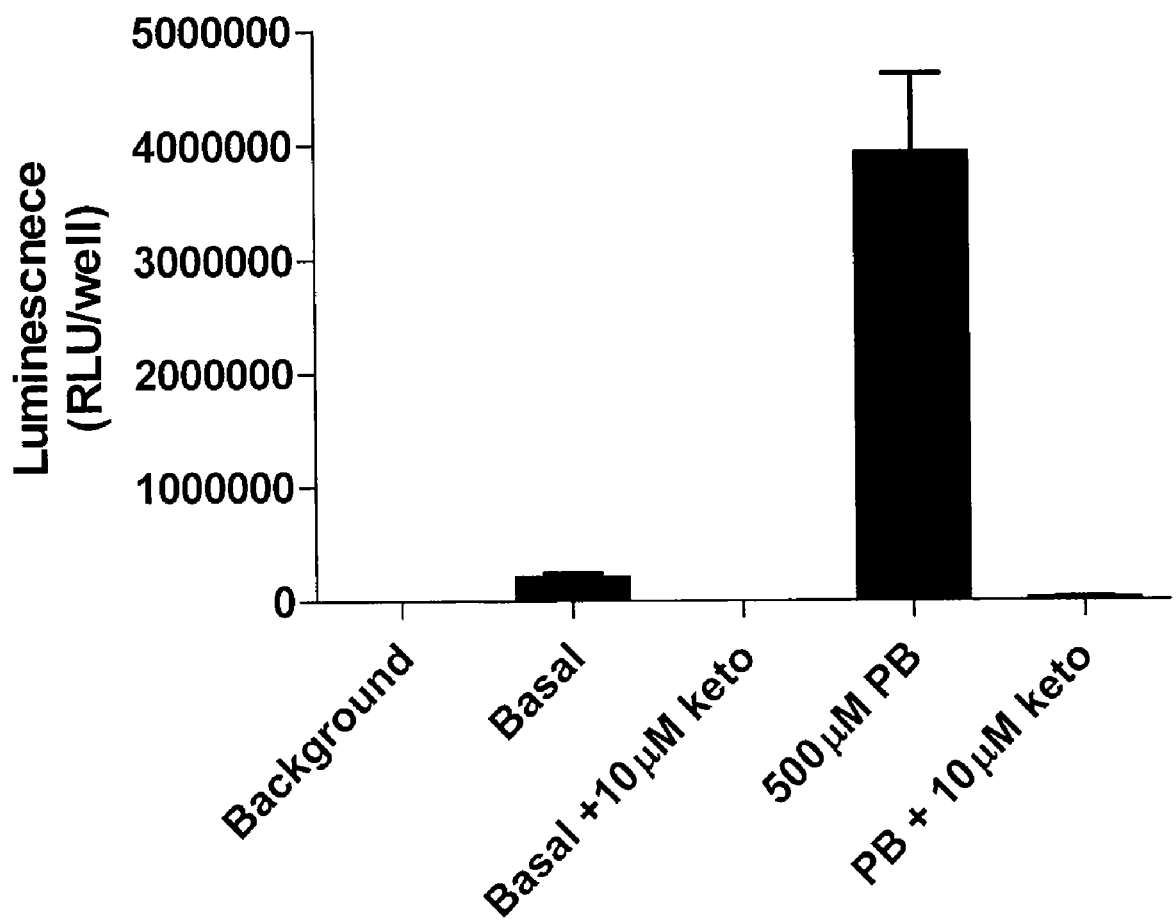
FIG. 21. CYP3A4 Induction in Human Hepatocytes. Compound 3391 was used as a bioluminescent probe to detect CYP3A4 activity in cultured hepatocytes after treatment with 500 µM Phenobarbital (PB) or the PB vehicle, 0.1% dimethylsulfoxide (DMSO), with or without 10 µM ketoconazole (keto). The mean and standard deviation of measurements from four replicate wells are shown. Background is the signal from wells containing medium and compound 3391 but no cells. Basal is the signal from wells containing medium, 0.1% DMSO and cells. The background value (not visible as a bar on the graph) is 990±71 RLU. The Basal+keto value (also not visible as a bar on the graph) is 3613±244 RLU.

In FIG. 21, human hepatocytes were purchased from Lonza. Briefly, the cells were harvested from the liver of a 16 year old female donor, seeded at near confluence on a collagen-coated 96-well tissue culture plate and overlayed with a solubilized basement membrane matrix preparation (Matrigel™, BD Bioscience). The cells were shipped from the vendor in a sealed plate at ambient temperature and maintained in a 37° C. incubator with 5% $CO_2$. Upon receipt of cells, the shipping medium was replaced with 100 µL/well InVitroGRO™ Hepatocyte Plating medium (Celsis). One day after receipt of the cells, the cells were treated with 100 µL/well InVitroGRO™ Hepatocyte Incubation medium containing 500 µM Phenobarbital or its vehicle, 0.1% DMSO.

Treatments were refreshed after 24 hours and maintained for a total of 48 hours. At the conclusion of the 48 hour treatment period, the treatment were removed and replaced with 60 µL/well incubation medium containing 4 µM compound 3391 or 4 µM compound 3391 plus 10 µM ketoconazole and incubated for 1 hour in a 37° C. incubator. For background measurement, 60 µL incubation medium containing 4 µM compound 3391 was applied to wells without cells of a separate 96-well tissue culture plate and incubated for 1 hour at 37° C. in parallel with the plates containing treated cells. After incubation, 50 µL of the medium from each well was transferred to a 96-well opaque, white, polystyrene plate, combined with 50 µL of LDR, and luminescence read after 20 minutes on a Veritas™ luminometer.

Example 1

A. Measuring Human Cytochrome P450 Enzyme Activity with Luciferin Derivatives

A two-step luminescent approach was used to measure P450 activity (Cali et al., *Exp. Op. Drug Metab. Toxicol.* (2006) vol. 2(4), 629-645; Cali, *Cell Notes.* 7:2 (2003); Cali et al., *Cell Notes,* 13:8 (2005a); and Cali, *Bioluminescent P450 assays that use D-luciferin derivatives as substrates for CYP1A1, 1A2, 1B1, 2C8, 2C9, 2J2, 3A4, 3A7, 4A11, 4F3B, 4F12 and 19, Proc. 14th Int. Conf. Cytochromes P450,* Medimond Int. Proc. (2005b)) with proluciferin acetals. Briefly, in a first step a proluciferin acetal of the present invention is oxidized initially by a P450 enzyme. The oxidized product is then thought to undergo a non-enzymatic conversion to a proluciferin ester. In a second step, the proluciferin ester is detected by adding a luciferase reaction mixture containing an esterase enzyme that converts the proluciferin ester to luciferin. The luciferin reacts with luciferase to produce an amount of light that is proportional to the amount of luciferin, and therefore to the amount of P450 enzyme activity. A sample that contains active P450 enzyme is typically compared to a control that is devoid of P450 activity. A P450-containing sample that gives a luminescent signal in significant excess over the control is scored as active without being bound to the suggested reaction mechanism.

Figure 2:
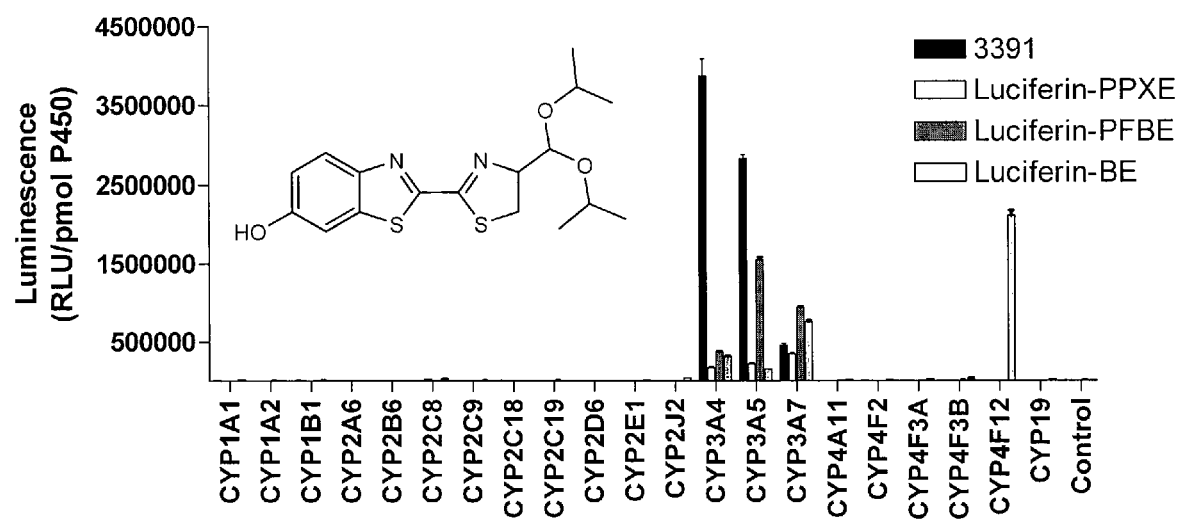
FIG. 2. P450 enzyme selectivity of compound 3391. A graphical representation of luminescence given in relative light units (RLU) for reactions containing acetal proluciferin derivative compound 3391 or a non-acetal proluciferin derivative (Luciferin-BE, Luciferin-PFBE or Luciferin-PPXE) screened against a panel of recombinant cytochrome P450 enzymes. The mean and standard deviation of measurements from three replicate reactions with each P450 enzyme are shown.
Figure 3:
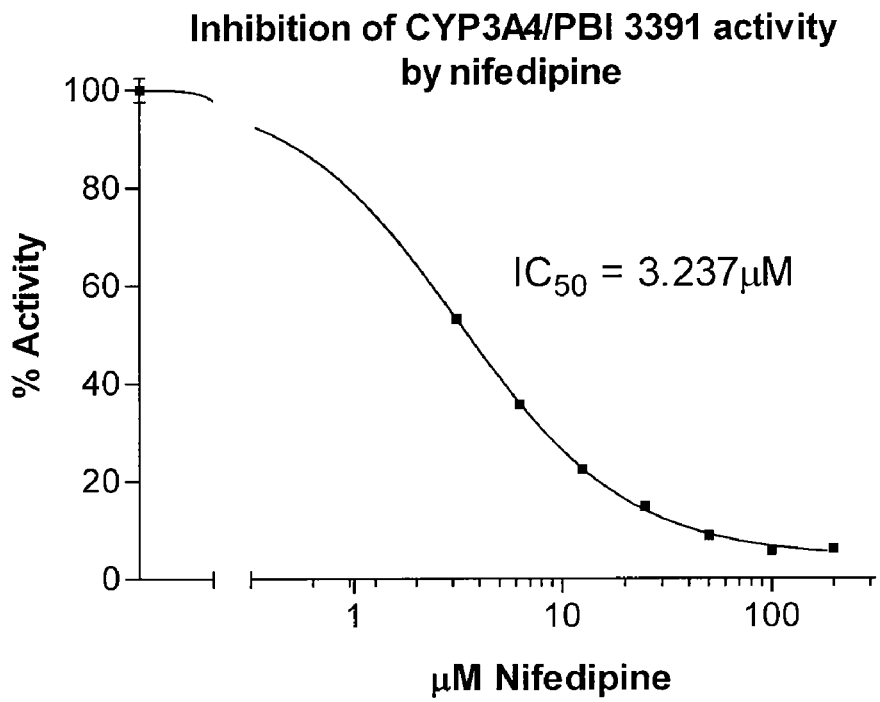
FIG. 3. Inhibition of CYP3A4 activity by nifedipine.
Figure 4:
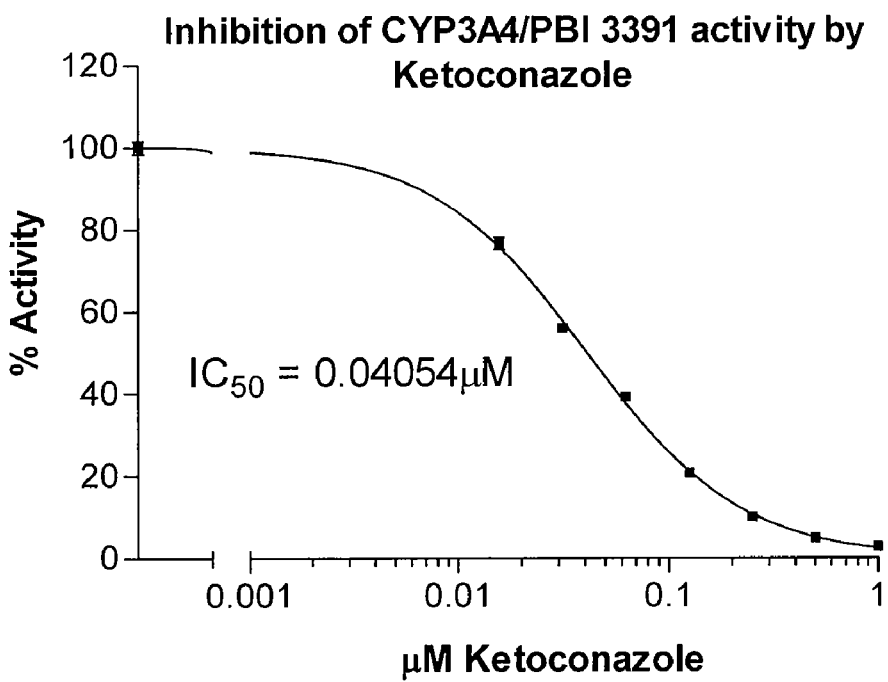
FIG. 4. Inhibition of CYP3A4 activity by ketoconazole.
Figure 5:
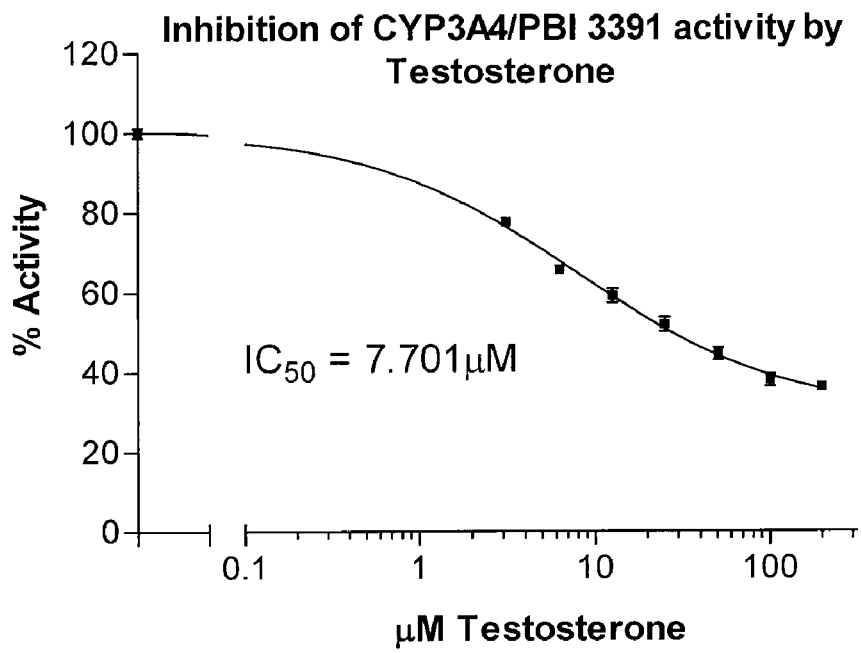
FIG. 5. Inhibition of CYP3A4 activity by testosterone.
Figure 6:
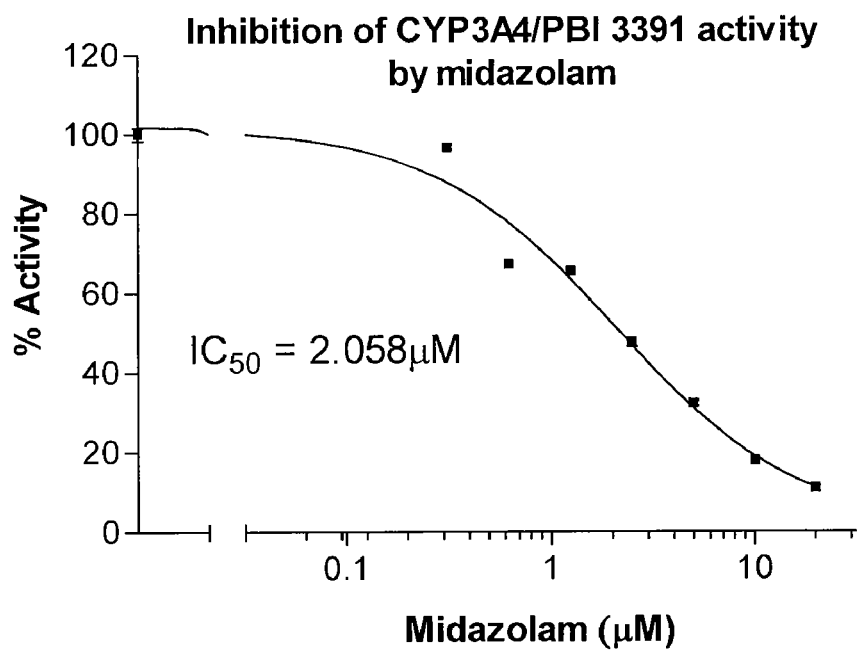
FIG. 6. Inhibition of CYP3A4 activity by midazolam.

The results in FIG. 2 demonstrate that a subset of a panel of 21 recombinant human cytochrome P450 enzymes do indeed mediate the conversion of the proluciferin acetal compound 3391 such that a luminescent signal is produced with luciferase that is in significant excess over control samples that lacked P450 enzyme activity. Furthermore, a brighter CYP3A4 signal against a lower minus P450 control reaction signal (background signal) was observed with compound 3391 compared to the non-acetal luciferin derivatives that are also CYP3A4 substrates (luciferin-PPXE: (S)-2-(6-(3-((4-phenylpiperazin-1-yl)methyl)-benzyloxy)benzo[d]thiazol-2-yl)-4,5-dihydrothiazole-4-carboxylic acid, luciferin-PFBE: (S)-2-(6-(perfluorobenzyloxy)benzo[d]thiazol-2-yl)-4,5-dihydrothiazole-4-carboxylic acid, and luciferin-BE: (S)-2-(6-(benzyloxy)benzo[d]thiazol-2-yl)-4,5-dihydrothiazole-4-carboxylic acid). Therefore, a substantially higher signal/background (S/B) ratio and greater assay sensitivity is observed with compound 3391.

For example, S/B for luciferin-BE, luciferin-PPXE and luciferin-PFBE was 55, 56 and 92, respectively, compared to a S/B of 1699 for compound 3391. A more sensitive assay makes it possible to use less P450 enzyme per reaction and to detect smaller amounts of P450 enzyme in a sample. This is particularly relevant to cell-based assays where basal CYP3A4 activity may be very low. Further, compound 3391 has better selectivity for CYP3A4 over the other CYP3A subfamily members, CYP3A5 and CYP3A7, as compared to the non-acetal luciferin substrates in FIG. 2. This improved selectivity is demonstrated more definitively in FIG. 20 where the panel of recombinant P450 enzymes was screened under conditions optimal for CYP3A4 to react with compound 3391. A more selective substrate is an advantage to differentiate CYP3A4 activity from the other CYP3A4 enzymes in samples such as liver microsomes, cultured hepatocytes and hepatocyte-like cell lines where multiple P450 enzymes are co-expressed.

B. Measuring CYP3A4 Activity in the Presence of Various Inhibitors

The signal generated by compound 3391 with CYP3A4 in the presence of various inhibitors was determined (FIGS. 3-6). The CYP3A4/3391 reaction was inhibited by the CYP3A4 substrates testosterone, midazolam, nifedipine, and the canonical 3A4 inhibitor ketoconazole. In contrast, CYP3A4 assays using the non-acetal luciferin derivatives luciferin-BE and luciferin-PFBE are inhibited by midazolam and stimulated by nifedipine and testosterone. The CYP3A4 assays using the non-acetal luciferin derivative luciferin-PPXE are inhibited by midazolam and nifedipine and stimulated by testosterone (Sobol, M. et al. Promega Notes, 2007, vol. 96, pages 15-18). Compound 3391 is therefore more versatile than the non-acetal luminogenic substrates as a probe for detecting CYP3A4 inhibitors, some of which may be CYP3A4 substrates acting as competitive inhibitors.

C. Measuring Concentration Dependence of CYP3A4

FIG. 7 illustrates the concentration dependence of the CYP3A4 reaction with compound 3391. The data displays a concentration-dependent increase in activity up to a maximal rate at 12.5 µM of compound 3391 and a slight decrease from that maximal observed rate at higher compound 3391 concentrations. The data fit well to a substrate inhibition model ($R^2=0.99$) described by the equation $Y=(V_{max} \cdot X)/(K_m+X+(X \cdot X/K_i))$, where X=substrate concentration, Y=activity in relative light units (RLU), $K_m$=the half maximal rate and $K_i$ = the substrate inhibition constant. The calculated $K_m$ and $K_i$ values for compound 3391 are 2 μM and 171 μM, respectively. This $K_m$ value is lower than the non-acetal luciferin derivative CYP3A4 substrates used in FIG. 2 (Luciferin-BE: $K_m$=50 μM, luciferin-PFBE: $K_m$=50 μM, luciferin-PPXE: $K_m$=25 μM) (Cali et al Exp. Op. Drug Metab. Toxicol (2006) vol. 2(4), 629-645).

D. Measuring Human CYP450 Enzyme Activity with Other Proluciferin Acetals

FIGS. 8-19 show the screening of several proluciferin acetals using a two-step assay scheme against a panel of 21 recombinant P450 enzymes and a control devoid of P450 enzyme activity. One picomole of each enzyme with the requisite co-factors and buffer were incubated for 30 minutes at 37° C. with the proluciferin acetal present at 50 μM. These conditions allowed for detection of even modest activities. Each proluciferin acetal showed activity, measured as an increase in luminescence compared to the minus P450 control, with various subsets of the 21 enzymes. The proluciferin acetals showed a strong preference for the CYP3A subfamily of P450 enzymes including CYP3A4, CYP3A5 and CYP3A7.

E. Demonstrating Compound 3391 Selectivity for CYP3A4

In FIG. 20, a refinement of the experiment shown in FIG. 2 using compound 3391 was performed to demonstrate the compound's selectivity for CYP3A4. An assay selective for CYP3A4 is of particular interest because of the enzyme's prominent role in drug metabolism. Designing an assay that is selective for CYP3A4 over the other CYP3A subfamily members, CYP3A5 and CYP3A7, is particularly challenging. Conditions used in FIG. 2 were designed to detect activity using compound 3391 with any of the P450 enzymes screened without a bias in favor a particular enzyme(s). Under those conditions, compound 3391 showed excellent selectivity for CYP3A, but only modest selectivity for CYP3A4 over CYP3A5 and CYP3A7 (1.4-fold selectivity for CYP3A4 over CYP3A5 and 8.5 fold selectivity for CYP3A4 over CYP3A7). In FIG. 20, the enzyme panel was re-screened under conditions that were optimal for compound 3391 to react with CYP3A4: compound 3391 was present at 2 μM with 0.1 picomole of each P450 enzyme in a reaction buffer of 100 mM KPO4 buffer at pH 7.4 for an incubation of 10 minutes at 37° C. The $K_m$ concentration of the CYP3A4 reaction is 2 μM, and 100 mM $KPO_4$ is the optimal buffer for CYP3A4 activity with compound 3391. Product accumulation with CYP3A4 is linear for at least 10 minutes, and when using 0.1 picomoles of CYP3A4, less than 10% of compound 3391 is oxidized during the 10 minute incubation. These conditions are ideal for an assay that will ultimately be used to screen for P450 inhibitors. Under these conditions, compound 3391 reactivity is highly selective for CYP3A4 showing an 8.0 fold preference for CYP3A4 over CYP3A5, a 48.5 fold preference for CYP3A4 over CYP3A7, and negligible activities with the other P450 enzymes screened.

The difference seen in FIGS. 2 and 20 regarding CYP3A4 selectivity over CYP3A5 and CYP3A7 can be explained in the fact that the conditions in FIG. 20 allow for steady state reaction kinetics throughout the incubation while in FIG. 2, the conditions allow for declining reaction rates over time due to substrate depletion. The bar heights of FIG. 20 represent the different reaction rates, whereas the bar heights of FIG. 2, resulting from a longer incubation and 10 times more enzyme, represent the extent of substrate utilization.

Example 2

An experiment using compound 3391 applied to cultured human hepatocytes was performed to measure CYP3A4 enzyme activity in the intact cells. FIG. 21 shows the background, basal and phenobarbitol-induced luminescent activities, and the inhibition by ketoconazole of basal and phenobarbitol-induced activity in human hepatocytes. The assay was performed as previously described for bioluminescent P450 enzyme assay using non-acetal luciferin derivatives (Sobol, M. et al. *Promega Notes,* 2007, vol. 96, pages 15-18; Cali et al., *Exp. Op. Drug Metab. Toxicol* (2006) vol. 2 (4), 629-645). Briefly, compound 3391 was dissolved in hepatocyte culture medium and applied to the cells after a 48 hour treatment with the known CYP3A4 inducer phenobarbitol or its vehicle, DMSO. Ketoconazole, a known CYP3A4 inhibitor was also applied to some of the wells in combination with compound 3391. After a brief exposure to the compounds, a sample of the medium from the cells was removed, combined in a separate plate with a Luciferin Detection Reagent (LDR), and luminescence read. An expectation of CYP3A4 selectivity is based on the recombinant enzyme panel screen shown in FIG. 20.

It was anticipated that compound 3391 and ketoconazole are taken up by the cells. Inside the cells, the CYP3A4 enzyme present in the cells oxidizes some of the 3391 to facilitate its conversion to a luciferin ester that is then converted to luciferin by esterase enzymes present in the cells. The amount of compound 3391 oxidized by CYP3A4 is dependent on the amount of CYP3A4 enzyme present, and the reaction rate with or without ketoconazole. The luciferin and/or luciferin ester may then diffuse back into the culture medium. Any luciferin ester remaining would be converted to luciferin by the esterase present in the LDR.

The data in FIG. 21 demonstrates that when using the method described herein, it was possible to detect basal activity as a luminescent signal in substantial excess over the assay background, and the activity was sensitive to inhibition by the CYP3A4 inhibitor ketoconazole. Furthermore, the basal activity was induced 18-fold by the known CYP3A4 inducer phenobarbitol, and this induced activity was also sensitive to inhibition by ketoconazole. Therefore, compound 3391 is an effective probe for measuring CYP3A4 activity in hepatocytes given that a basal activity was induced by a CYP3A4 inducer and inhibited by a CYP3A4 inhibitor. Furthermore, the data is consistent with the expectation of CYP3A4 selectivity indicated by FIG. 20.

Example 3

Preparation of 2-(4-(Diisopropoxymethyl)-4,5-dihydrothiazol-2-yl)benzo[d]thiazol-6-ol

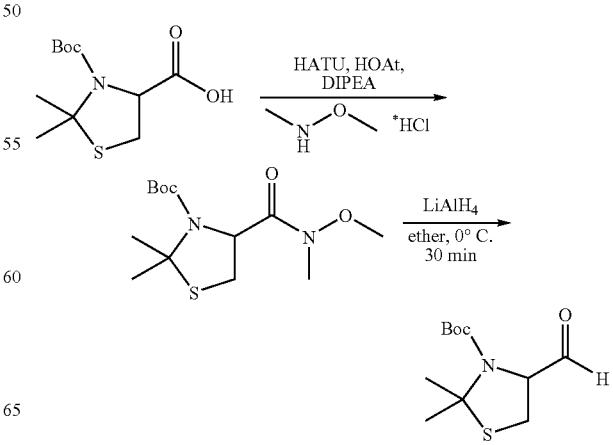

-continued

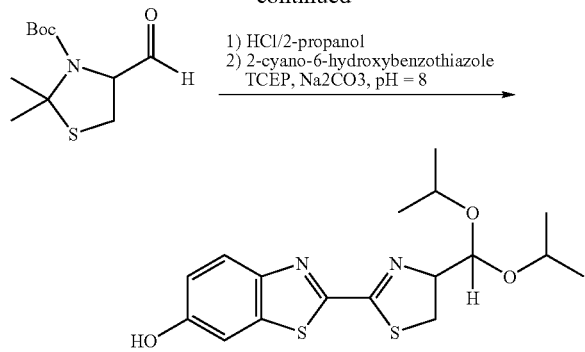

1) HCl/2-propanol
2) 2-cyano-6-hydroxybenzothiazole
TCEP, Na2CO3, pH = 8

A. tert-Butyl 4-(methoxy(methyl)carbamoyl)-2,2-dimethylthiazolidine-3-carboxylate A flask containing 3-(tert-butoxycarbonyl)-2,2-dimethylthiazolidine-4-carboxylic acid (see Suaifan et al., Tetrahedron 62, 11245-11266 (2006); Kemp and Carey, J. Org. Chem. 54, 3640 (1989)) (4 g, 0.015 mol), HATU (7.3 g, 0.019 mol), HOAt (28 ml of 0.6M, 0.017 mol), N,O-dimethylhydroxylamine-HCl (2.92 g, 0.03 mol), diethylisopropylamine (5.1 L, 0.03 mol), and DMF (20 mL) was stirred at room temp for 17 h. Solvent was evaporated, and the residue was portioned between EtOAc (200 mL) and water (300 mL). The aqueous layer was extracted with EtOAc (50 mL), and the combined organic layers washed with 30% citric acid solution (2×100 mL), saturated bicarbonate (2×100 mL), and brine (1×50 mL). After evaporation, the crude residue was chromatographed on normal phase silica—eluting with heptane/EtOAc (2/1) to yield 3.84 g (84%) solid.

B. tert-Butyl 4-formyl-2,2-dimethylthiazolidine-3-carboxylate

A flask containing tert-butyl 4-(methoxy(methyl)carbamoyl)-2,2-dimethylthiazolidine-3-carboxylate (2), 0.918 g, 3 mmol and diethyl ether (20 mL) was cooled in an ice bath. To the cooled solution, lithium aluminum hydride (160 mg, 4.2 mmol) was added. After 1 h additional ether (20 mL) was added. After an additional 1 h, a solution of potassium bisulfate (315 mg) in water (1 mL) was added carefully to the reaction. Celite was added, the mixture was filtered, and the solids were rinsed with additional ether. The collected ether was washed with 0.1 N HCl(aq) (15 mL), saturated sodium bicarbonate (15 mL), and brine (15 ml). The ether was dried over Na2SO4, evaporated and used without further purification. Yield 684 mg (92%)

C. 2-(4-(Diisopropoxymethyl)-4,5-dihydrothiazol-2-yl)benzo[d]thiazol-6-ol tert-Butyl 4-formyl-2,2-dimethylthiazolidine-3-carboxylate (750 mg, 3.06 mmol) was suspended in isopropanol (20 mL) and stirred under nitrogen at room temperature. HCl (2.3 mL, 4.0 M dioxane solution) was added dropwise and the reaction was stirred for 16 h. To the reaction mixture a solution of TCEP (1.49 g, 5.2 mmol) in 5 mL water was added. The pH of the reaction was adjusted to ca. 8 with a solution of saturated sodium carbonate. A solution of 6-hydroxy-benzo[d]thiazole-2-carbonitrile (590 mg, 3.35 mmol) in THF (5 mL) was added dropwise and the reaction was stirred for 20 hours. The reaction was stopped when HPLC analysis showed no more progress. The solvent was evaporated in vacuo and the resulting yellow residue was taken up in acetonitrile:water (1:1) and purified by reverse phase chromatography using a 50 mM TEAA/ACN gradient from 90/10 to 100% ACN over 30 minutes. Evaporation of the solvent afforded 300 mgs of the desired product. $^1$H-NMR (300 MHz, CD$_2$C$_{12}$)□: 7.94 (d, 1H, J=9 Hz), 7.32 (d, 1H, J=2.4 Hz), 7.05 (dd, 1H, J=8.7 Hz, 2.4 Hz), 4.95 (d, 1H, J=4.5 Hz), 4.79 (1H, m), 3.90 (2H, m), 3.48 (2H, m), 1.2 (12H, m); mass spectrum, calculated for C$_{17}$H$_{23}$N$_2$O$_3$S$_2$ (MH$^+$) 367.1. Found 367.2.

Example 4

Preparation of Dimethoxymethyl Thiazolylbenzothiazol Derivatives

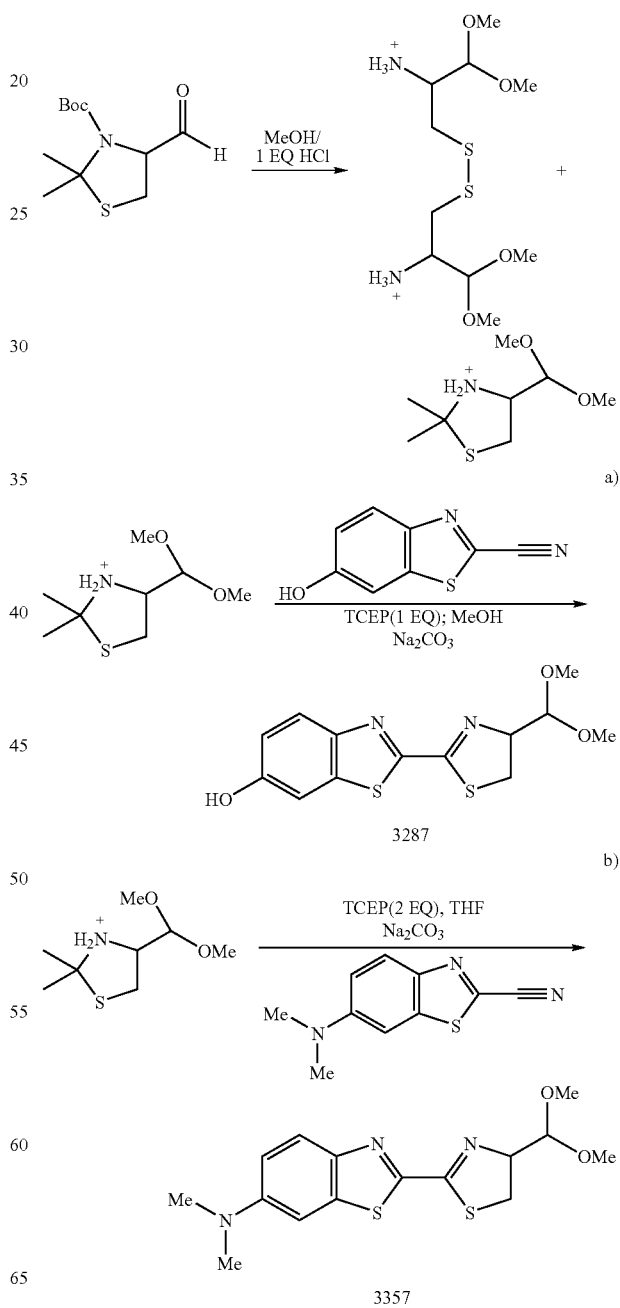

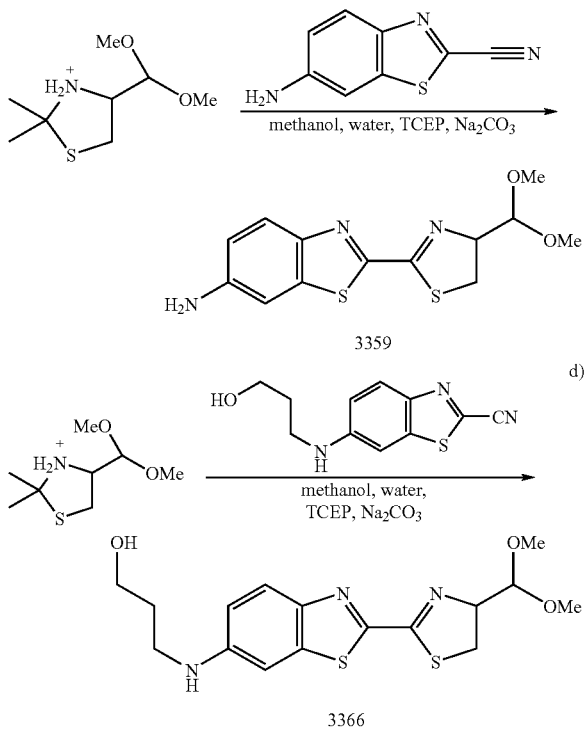

A. 4-(Dimethoxymethyl)-2,2-dimethylthiazolidine

To a flask containing tert-butyl 4-formyl-2,2-dimethylthiazolidine-3-carboxylate (684 mg, 2.8 mmol) and methanol (4 mL) 4M HCl in dioxane (500 µL) was added. After 48 hours of stirring at room temperature, diethyl ether (20 mL) was added. The solution was placed in a freezer. After filtration, two addition crystallization crops were recovered to yield 145 mg of solid product (21% yield).

B. 2-(4-(dimethoxymethyl)-4,5-dihydrothiazol-2-yl)benzo[d]thiazol-6-ol (Method A) (compound 3287)

To a vial containing 4-(dimethoxymethyl)-2,2-dimethylthiazolidine (40 mg, 0.17 mmol) in methanol (1 mL), enough saturated sodium bicarbonate solution was added to adjust the pH to 7.5. A solution of 2-cyano-6-hydroxybenzothiazole (31 mg, 0.17 mmol) in methanol (1 mL) was added to the reaction. Additionally, a aqueous solution of TCEP (43 mg, 0.17 mmol, adjusted pH=8 w/sat $Na_2CO_3$) was added to the reaction. After 2 hours, 3 drops of saturated $Na_2CO_3$ (aq) was added to the reaction. After 72 hours, reaction was partitioned between water (20 mL) and EtOAc (20 mL); extracted EtOAc (20 mL); combined org washed 1×10 mL water, 1×10 mL sat citric acid solution, 1×10 mL brine, and dried over sodium sulfate. After evaporation, the residue was purified on preparative RP-HPLC to ultimately yield 31 mg solid. $^1$H NMR (300 MHz, DMSO) δ 10.13 (s, 1H), 7.91 (dd, J=2.7, 8.8, 1H), 7.39 (d, J=2.4, 1H), 7.01 (dd, J=2.5, 8.9, 1H), 4.84 (td, J=5.5, 9.3, 1H), 4.60 (d, J=5.0, 1H), 3.54-3.20 (m, 11H (includes water peak)).

C. 2-(4-(dimethoxymethyl)-4,5-dihydrothiazol-2-yl)-N,N-dimethylbenzo[d]thiazol-6-amine (compound 3357)

Synthesized using method A substituting 6-(N,N-dimethylamino)-2-cyanobenzolthiazole (synthesized from the exhaustive methylation with methyl iodide of 6-amino-2-cyanobenzothiazole) for the 2-cyano-6-hydroxybenzothiazole. ($^1$H NMR (300 MHz, CDCl3) δ 7.97 (d, J=9.1, 1H), 7.25 (s, 1H), 7.02 (d, J=9.0, 1H), 4.86 (dd, J=5.2, 9.3, 1H), 4.63 (d, J=4.8, 1H), 3.50 (dd, J=2.8, 14.8, 8H), 3.08 (t, J=4.6, 7H); mass spectrum, calculated (MH$^+$) 338. found 338.

D. 2-(4-(dimethoxymethyl)-4,5-dihydrothiazol-2-yl)benzo[d]thiazol-6-amine (compound 3359)

Synthesized using method A substituting 6-amino-2-cyanobenzolthiazole (O'Brien et al., U.S. Pat. No. 7,148,030) for the 2-cyano-6-hydroxybenzothiazole. $^1$H NMR (300 MHz, CDCl3) δ 7.85 (d, J=8.8, 1H), 7.04 (d, J=2.3, 1H), 6.82 (dd, J=2.3, 8.8, 1H), 4.84 (td, J=5.1, 9.0, 1H), 4.59 (d, J=5.1, 1H), 3.55-3.33 (m, 9H), 1.97 (d, J=0.6, 2H). mass spectrum, calculated (MH$^+$) 310. found 310.

E. 3-(2-(4-(dimethoxymethyl)-4,5-dihydrothiazol-2-yl)benzo[d]thiazol-6-ylamino)propan-1-ol (compound 3366)

Synthesized using method A substituting 6-(3-hydroxypropylamino)-2-cyanobenzolthiazole (Daily, Hawkins, et al., WO 2006/130551) for the 2-cyano-6-hydroxybenzothiazole. $^1$H NMR (300 MHz, CDCl3) δ 7.85 (dd, J=2.4, 8.9, 1H), 6.97 (d, J=2.3, 1H), 6.80 (dd, J=2.4, 8.9, 1H), 4.86 (dt, J=6.9, 13.9, 1H), 4.61 (dd, J=2.5, 5.0, 1H), 3.91-3.75 (m, 2H), 3.59-3.38 (m, 9H), 3.36-3.25 (m, 2H), 2.16 (d, J=2.6, 1H), 2.02-1.82 (m, 2H). mass spectrum, calculated (MH$^+$) 368. found 368.

Example 5

Preparation of Mixed Acetal Derivatives

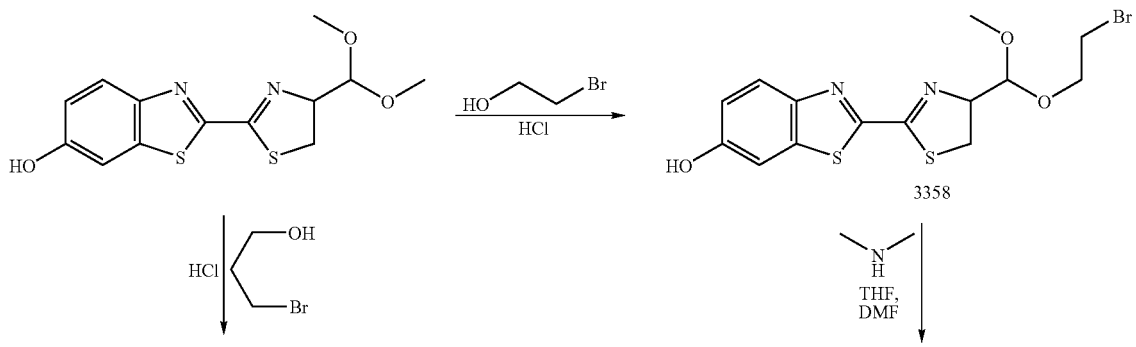

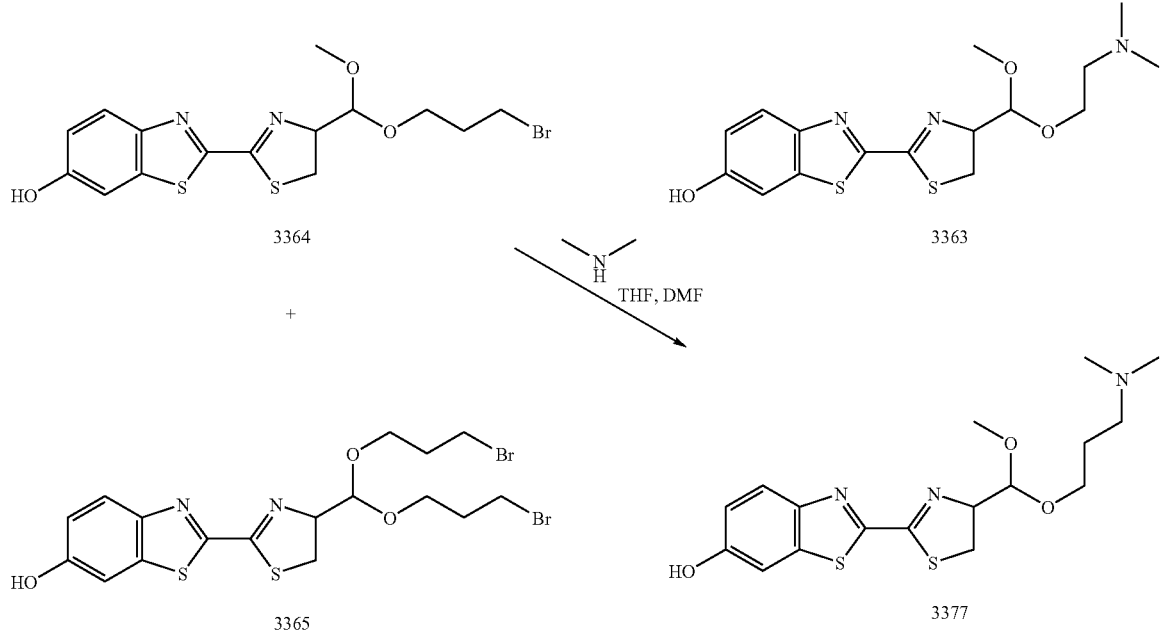

A. 2-(4-((2-bromoethoxy)(methoxy)methyl)-4,5-dihydrothiazol-2-yl)benzo[d]thiazol-6-ol (Method B) (compound 3358)

To a vial containing 2-(4-(dimethoxymethyl)-4,5-dihydrothiazol-2-yl)benzo[d]thiazol-6-ol (50 mg), 2-bromoethanol (1 mL) and a solution of HCl in dioxane (125 uL of 4M) was added. After 4 hours at room temperature, an aqueous solution of triethylammonium acetate (TEAA) (1 mL of 1M) was added to the reaction. After filtration, the solution was purified by preparative RP-HPLC by eluting with 50 mM TEAA ramping to acetonitrile over 30 min. Yield 26 mg. $^1$H NMR (300 MHz, CDCl3) δ 7.96 (d, J=8.9, 1H), 7.33 (d, J=2.4, 1H), 7.06 (dd, J=2.3, 8.9, 1H), 4.88 (dt, J=6.8, 13.2, 1H), 4.79-4.67 (m, 1H), 4.16-3.73 (m, 3H), 3.64-3.38 (m, 8H), 1.36 (dd, J=2.4, 5.3, 1H). mass spectrum, calculated (MH$^+$) 304/306. found 304/306

B. 2-(4-((3-bromopropoxy)(methoxy)methyl)-4,5-dihydrothiazol-2-yl)benzo[d]thiazol-6-ol (compound 3364) and 2-(4-(bis(3-bromopropoxy)methyl)-4,5-dihydrothiazol-2-yl)benzo[d]thiazol-6-ol (compound 3365)

Synthesized using method B starting with 2-(4-(dimethoxymethyl)-4,5-dihydrothiazol-2-yl)benzo[d]thiazol-6-ol (200 mg), 3-bromopropanol (2 mL), and a solution of HCl in dioxane (480 uL of 4M). Products were separated on preparative RP-HPLC. Mixed acetal yielded 70 mg $^1$H NMR (300 MHz, CDCl3) δ 7.97 (d, J=8.9, 1H), 7.29 (d, J=2.2, 1H), 7.05 (dd, J=2.2, 8.9, 1H), 5.00-4.64 (m, 2H), 3.99-3.64 (m, 2H), 3.62-3.40 (m, 7H), 2.26-1.99 (m, 2H). mass (MH$^+$) calc and found 416/418; Symmetric acetal yielded 20 mg. $^1$H NMR (300 MHz, CDCl3) δ 7.96 (d, J=8.9, 1H), 7.33 (d, J=2.4, 1H), 7.06 (dd, J=2.5, 8.9, 1H), 4.90 (ddd, J=4.7, 11.2, 18.2, 2H), 3.91 (td, J=5.5, 9.1, 2H), 3.72 (ddd, J=5.7, 9.6, 20.4, 2H), 3.60-3.41 (m, 6H), 2.13 (ddd, J=6.1, 12.2, 19.4, 4H). mass (MH$^+$) calc and found 523/525/527.

C. 2-(4-((2-(dimethylamino)ethoxy)(methoxy)methyl)-4,5-dihydrothiazol-2-yl)benzo[d]thiazol-6-ol (compound 3363)

To a vial containing 2-(4-((2-bromoethoxy)(methoxy)methyl)-4,5-dihydrothiazol-2-yl)benzo[d]thiazol-6-ol (16 mg) in DMF (200 uL) dimethylamine (40 uL of 2M in THF) was added. After 28 hours at room temperature, the reaction was purified by preparative RP-HPLC to yield 8 mg. $^1$H NMR (300 MHz, CDCl3) δ 7.78 (d, J=9.2, 1H), 7.14 (d, J=2.2, 1H), 6.97 (d, J=8.9, 1H), 4.74-4.59 (m, 2H), 4.12-3.78 (m, 1H), 3.21 (dd, J=7.2, 14.9, 1H), 3.10 (s, 2H), 2.63 (s, 5H), 1.29 (t, J=7.3, 1H). mass (MH$^+$) calc and found 368.

Example 6

Preparation of Quinoline Acetal Derivatives of Luciferin

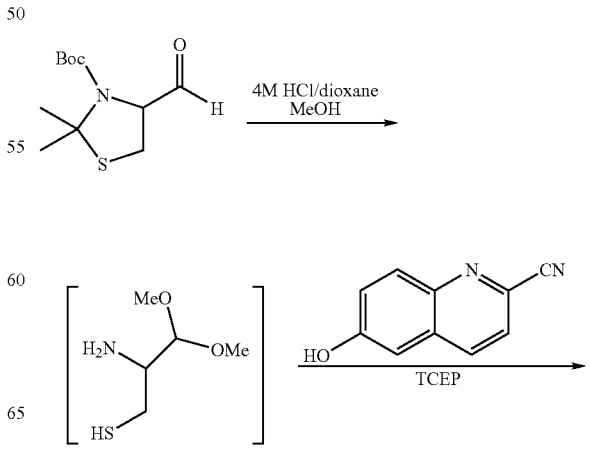

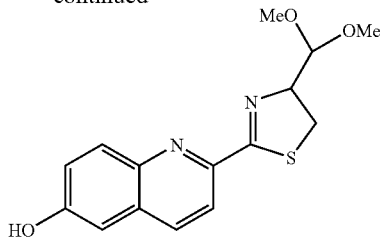

4-(Dimethoxymethyl)-2,2-dimethylthiazolidine can be prepared as described in Example 4. The quinoline derivative of luciferin 2-(2-(4-(dimethoxymethyl)-4,5-dihydrothiazol-2-yl)-6-hydroxyquinoline can then be prepared according to Method A in Example 4, substituting 2-cyano-6-hydroxyquinoline (see WO 2006/130551 (Daily, Hawkins, et al.)) for the 2-cyano-6-hydroxybenzothiazole.

Using the techniques described in Examples 3-5, various other quinoline acetals can be prepared. Appropriate quinoline nitriles can be obtained commercially or prepared by methods known to those of skill in the art. For example, quinoline derivatives may be prepared by using quinoline starting materials with various substitutions at the quinoline 6 position. Examples include quinolines with 6-O substitutions or 6-N substitutions, wherein the substituents can be, for example, those shown for the various benzothiazole and luciferin derivatives described herein. Additionally, other acetals and mixed acetals can be prepared, for example, using the techniques described in Example 5.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:
1. A compound of formula (I):

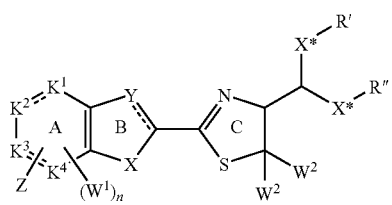

wherein
Y is N, N-oxide, N—$(C_1\text{-}C_6)$alkyl, or CH;
X is S, O, CH=CH, N=CH, or CH=N;
each X* is independently O or S;
R' and R" are independently $(C_1\text{-}C_{20})$alkyl, $(C_2\text{-}C_{20})$alkenyl, $(C_2\text{-}C_{20})$alkynyl, $(C_3\text{-}C_{20})$cycloalkyl, $(C_6\text{-}C_{30})$aryl, heteroaryl, or heterocycle, and may be optionally substituted with hydroxyl, $(C_1\text{-}C_{12})$alkoxy, oxy, amino, halo, carboxyl, thio, $(C_6\text{-}C_{30})$aryl, heteroaryl, or heterocycle, or R' and R" together form a cyclic moiety;
Z is H, OH, OR, $NH_2$, NHR, or NRR;
$W^1$ is H, halo, $(C_1\text{-}C_6)$alkyl, $(C_2\text{-}C_{20})$alkenyl, hydroxyl, or $(C_1\text{-}C_6)$alkoxy; and n is 1, 2, or 3; or a $W^1$ and Z together form a keto group on ring A, and at least one of the dotted lines denoting optional bonds in ring A is absent;
each $W^2$ is independently H, halo, $(C_1\text{-}C_6)$alkyl, $(C_2\text{-}C_4)$alkenyl, hydroxyl, or $(C_1\text{-}C_6)$alkoxy;
each of $K^1$, $K^2$, $K^3$, and $K^4$ is independently CH, N, N-oxide, or N—$(C_1\text{-}C_6)$alkyl, and the dotted lines between $K^1$ and $K^2$, and $K^3$ and $K^4$, denote optional bonds; and when the carbon of any CH is substituted, the H is absent;
the dotted line in ring B is an optional bond;
each R is independently H, $(C_1\text{-}C_{20})$alkyl, $(C_2\text{-}C_{20})$alkenyl, $(C_2\text{-}C_{20})$alkynyl, $(C_3\text{-}C_{20})$cycloalkyl, $(C_1\text{-}C_{12})$alkoxy, $(C_6\text{-}C_{30})$aryl, aryl$(C_1\text{-}C_{20})$alkyl, heteroaryl, heterocycle, $(C_1\text{-}C_{20})$alkylsulfonyl, $(C_6\text{-}C_{30})$arylsulfonyl, heteroarylsulfonyl, $(C_1\text{-}C_{20})$alkylsulfinyl, $(C_6\text{-}C_{30})$arylsulfinyl, heteroarylsulfinyl, $(C_1\text{-}C_{20})$alkoxycarbonyl, amino, $NH(C_1\text{-}C_6)$alkyl, $N((C_1\text{-}C_6)$alkyl$)_2$, tri$(C_1\text{-}C_{20})$ammonium$(C_1\text{-}C_{20})$alkyl, heteroaryl$(C_1\text{-}C_{20})$alkyl, heteroaryl having quaternary nitrogen, heteroarylcarbonyl having quaternary nitrogen, $(C_6\text{-}C_{30})$arylthio, $(C_1\text{-}C_{20})$alkylphosphate, $(C_1\text{-}C_{20})$alkylphosphonate, $(C_6\text{-}C_{30})$arylphosphate, $(C_6\text{-}C_{30})$arylphosphonate, phosphate, sulfate, or saccharide;
or when Z is NRR, RR together with the N to which they are attached optionally form a heteroaryl or heterocycle group;
wherein any alkyl, alkenyl, alkynyl, cycloalkyl, alkoxy, amino, aryl, heteroaryl, or heterocycle group is optionally substituted with 1, 2, 3, 4, or 5 substituents selected from $(C_1\text{-}C_{20})$alkyl, $(C_2\text{-}C_{20})$alkenyl, $(C_2\text{-}C_{20})$alkynyl, $(C_3\text{-}C_{20})$cycloalkyl, $(C_1\text{-}C_{20})$alkoxyl, $(C_1\text{-}C_{20})$alkylcarbonyl, $(C_1\text{-}C_{20})$alkylcarboxyl, halo, hydroxy, —$COOR^x$, —$S(O)R^x$, —$SO_2R^x$, —$SO_3R^x$, nitro, amino, phosphate, $(C_1\text{-}C_{20})$alkylphosphate, $(C_1\text{-}C_{20})$alkylphosphonate, $NH(C_1\text{-}C_6)$alkyl, $NH(C_1\text{-}C_6)$alkynyl, $N((C_1\text{-}C_6)$alkyl$)_2$, $N((C_1\text{-}C_6)$alkynyl$)_2$, mercapto, $(C_1\text{-}C_{20})$alkylthio, $(C_6\text{-}C_{14})$aryl, $(C_6\text{-}C_{14})$arylthio, trifluoromethyl, =O, heteroaryl, or heterocycle, and each substituent is optionally substituted with one to three R groups; wherein $R^x$ is H, $(C_1\text{-}C_6)$alkyl, $(C_6\text{-}C_{14})$aryl, heterocycle, or heteroaryl;
or a salt thereof;
when Z comprises a nitrogen moiety, one or both of the hydrogens of the Z nitrogen moiety may be replaced by $(C_1\text{-}C_{20})$alkyl or the group L, wherein L is an amino acid radical, a peptide radical having up to 20 amino acid moieties, or any other small molecule that is a substrate for a nonluciferase;
when Z is a hydroxyl group or a nitrogen moiety, H of the hydroxyl or nitrogen moiety may be replaced by $(HO)_2P(O)$—$OCH_2$—, sulfo, —$PO_3H_2$, or by a cephalosporanic acid attached to the group Z via a carbon chain of one to about 12 carbon atoms;
when Z is a hydroxyl group or a nitrogen moiety, one H of the hydroxyl or nitrogen moiety may be replaced by the group L'-linker, wherein L' is a group removable by an enzyme to free the linker, and linker is a carbon chain that can self-cleave, optionally interrupted by one or more nitrogen atoms, oxygen atoms, carbonyl groups, optionally substituted aromatic rings, or peptide bonds;
linker is attached to L' via an oxygen atom or an NH group at one terminus of the linker and the other terminus of the linker forms an ether, ester, or amide linkage with a group Z; and
when Z is OR, formula I is optionally a dimer connected at the two A rings via a linker comprising a $(C_1\text{-}C_{12})$alkyl diradical that is optionally interrupted by one to four O atoms, N atoms, or an optionally substituted aryl, heteroaryl, or heterocycle group to form a bridge between the dimer of formula I, and the R group of each Z group connecting the dimer of formula I is replaced by the bridge.

2. The compound of claim 1 wherein a) each of $K^1$-$K^4$ is CH or C, b) each $W^1$ is independently H, F, or Cl; n is 1 or 2 and each $W^2$ is H, c) Y is N and X is S or —CH=CH—, d) X is S, e) X* is O, f) R' and R" are each independently optionally substituted $(C_1$-$C_{12})$ alkyl, g) R' and R" together with the —X*—CH—X*- to which they are attached form a 5 12-membered optionally substituted heterocycle group, h) Z is NRR, wherein each R is independently H or an optionally substituted $(C_1$-$C_{12})$ alkyl, i) Z is OH or OR, wherein R is an optionally substituted $(C_1$-$C_{20})$ alkyl, $(C_6$-$C_{30})$ aryl, or $(C_1$-$C_{12})$ alkyl $(C_6$-$C_{14})$ aryl group, or j) a combination of a-i.

3. The compound of claim 1 wherein Y is N; X is S or —CH=CH—; each X* is O; $W^1$ is H, F, or Cl; n is 1 or 2; $W^2$ is H; and $K^1$, $K^2$, $K^3$, and $K^4$ are all C or CH.

4. The compound of claim 1 wherein Z is at the 6' position of ring A; Z is OH, $NH_2$, $NMe_2$ or $NHCH_2CH_2CH_2OH$; and $W^1$ is H, F, or Cl at the 5' position of ring A.

5. The compound of claim 1 selected from:

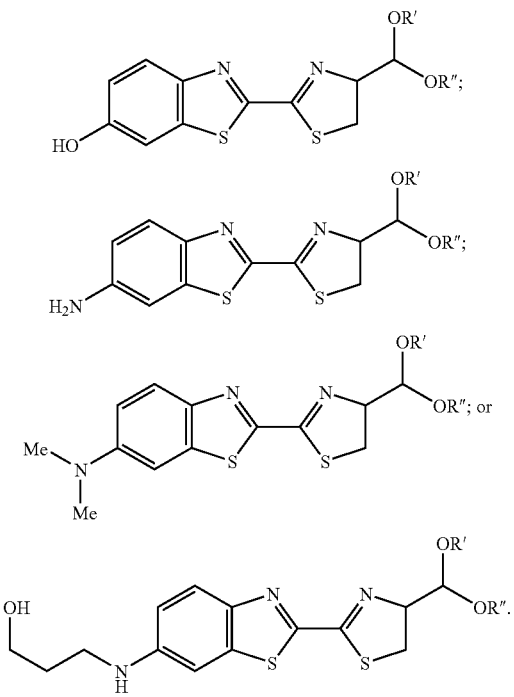

6. A compound wherein the structure is

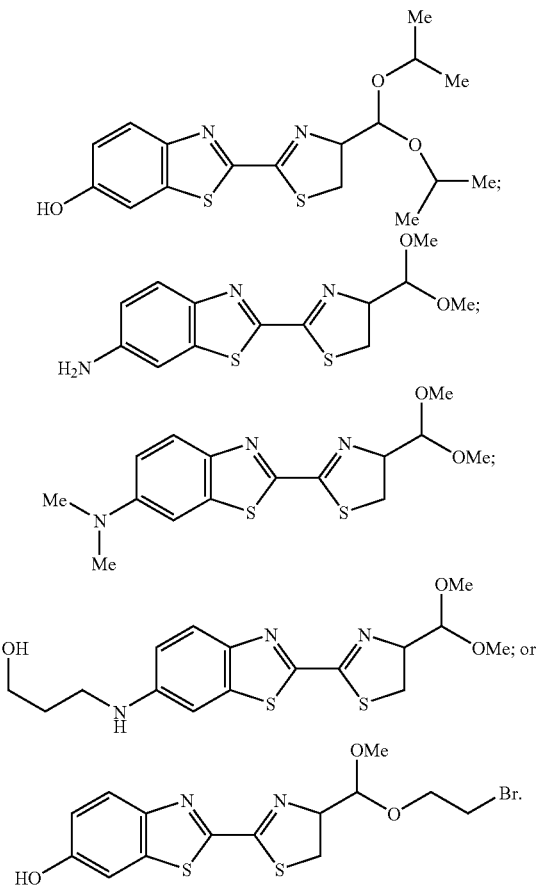

7. A method to detect or determine the presence or amount of a molecule for a nonluciferase enzyme-mediated reaction, comprising detecting or determining luminescence in a mixture thereby detecting or determining the presence or amount of the molecule, wherein the mixture comprises a sample, a reaction mixture for a nonluciferase enzyme-mediated reaction, and a compound of claim 1.

8. The method of claim 7 wherein the nonluciferase enzyme is a cytochrome P450 enzyme.

9. The method of claim 7 wherein R' and R" in the compound of formula (I) are independently $(C_1$-$C_6)$alkyl.

10. The method of claim 7 wherein the compound is a substrate for the nonluciferase enzyme and a prosubstrate for a beetle luciferase.

11. The method of claim 7 wherein the mixture further comprises a reaction mixture for a luciferase-mediated reaction.

12. The method of claim 7 wherein the molecule to be detected or determined is the nonluciferase enzyme or a cofactor for the nonluciferase enzyme.

13. The method of claim 7 wherein the sample comprises a preparation of intact cells, a cell lysate, a subcellular fraction, a tissue, a tissue fraction, or a purified or partially purified enzyme preparation.

14. A method for determining the effect of an agent(s) on nonluciferase enzyme activity comprising detecting or determining luminescence in a mixture thereby determining the effect of the agent(s) on nonluciferase enzyme activity, wherein the mixture comprises one or more agents, a reaction mixture for a nonluciferase enzyme-mediated reaction, and a compound of claim 1.

15. The method of claim 13 wherein the compound is a substrate for the nonluciferase enzyme and a prosubstrate for a beetle luciferase.

16. The method of claim 13 wherein the mixture further comprises a reaction mixture for a luciferase-mediated reaction.

17. The method of claim 13 wherein the nonluciferase enzyme is a cytochrome P450 enzyme, flavin monoxygenase, or cytochrome P450 3A enzyme.

18. A method for determining the effect of a compound on cytochrome P450 enzyme activity in an animal comprising detecting or determining luminescence in the animal thereby determining cytochrome P450 enzyme activity in the animal, wherein the animal has been exposed to a test compound and a compound of claim 1.

19. The method of claim 17 wherein the compound is a substrate for the cytochrome P450 enzyme and a prosubstrate for a beetle luciferase.

20. The method of claim 17 wherein the animal is a transgenic animal having a bioluminescent enzyme transgene.

* * * * *